US008623418B2

(12) United States Patent
Liang et al.

(10) Patent No.: US 8,623,418 B2
(45) Date of Patent: Jan. 7, 2014

(54) PHARMACEUTICAL COMPOSITION

(75) Inventors: Alfred Liang, Edison, NJ (US); Frank Matthews, Edison, NJ (US); Garth Boehm, Westfield, NJ (US); Lijuan Tang, Flemington, NJ (US); Frank Johnson, Bridgewater, NJ (US); Joseph Stauffer, Skillman, NJ (US)

(73) Assignee: Alpharma Pharmaceuticals LLC, Bridgewater, NJ (US)

( * ) Notice: Subject to any disclaimer, the term of this patent is extended or adjusted under 35 U.S.C. 154(b) by 326 days.

(21) Appl. No.: 12/336,267

(22) Filed: Dec. 16, 2008

(65) Prior Publication Data

US 2010/0152221 A1 Jun. 17, 2010

Related U.S. Application Data

(60) Provisional application No. 60/007,882, filed on Dec. 17, 2007.

(51) Int. Cl.
*A61K 9/16* (2006.01)
*A61K 9/22* (2006.01)
*A61K 9/24* (2006.01)

(52) U.S. Cl.
USPC ............................ 424/490; 424/468; 424/472

(58) Field of Classification Search
None
See application file for complete search history.

(56) References Cited

U.S. PATENT DOCUMENTS

| | | |
|---|---|---|
| 2,770,569 A | 11/1956 | Fromherz et al. |
| 2,945,049 A | 7/1960 | Chang et al. |
| 2,981,641 A | 4/1961 | O'Neill |
| 3,071,509 A | 1/1963 | O'Neil |
| 3,332,950 A | 7/1967 | Blumberg et al. |
| 3,493,657 A | 2/1970 | Lewenstein et al. |
| 3,676,557 A | 7/1972 | Lachman et al. |
| 3,689,574 A | 9/1972 | Engelhart |
| 3,773,955 A | 11/1973 | Pachter et al. |
| 3,845,770 A | 11/1974 | Theeuwes et al. |
| 3,852,058 A | 12/1974 | Huffman |
| 3,860,619 A | 1/1975 | Christensen et al. |
| 3,879,555 A | 4/1975 | Pachter et al. |
| 3,916,889 A | 11/1975 | Russell |
| 3,965,256 A | 6/1976 | Leslie |
| 3,966,940 A | 6/1976 | Pachter et al. |
| 3,971,725 A | 7/1976 | Douglass |
| 3,980,766 A | 9/1976 | Shaw et al. |
| 3,993,073 A | 11/1976 | Zaffaroni |
| 4,008,719 A | 2/1977 | Theeuwes et al. |
| 4,036,228 A | 7/1977 | Theeuwes |
| 4,063,064 A | 12/1977 | Saunders et al. |
| 4,088,864 A | 5/1978 | Theeuwes et al. |
| 4,111,201 A | 9/1978 | Theeuwes |
| 4,111,202 A | 9/1978 | Theeuwes |
| 4,122,084 A | 10/1978 | Douglass |
| 4,176,186 A | 11/1979 | Goldberg |
| 4,237,140 A | 12/1980 | Dudzinski |
| 4,293,539 A | 10/1981 | Ludwig et al. |
| 4,327,725 A | 5/1982 | Cortese et al. |
| 4,366,310 A | 12/1982 | Leslie |
| 4,401,672 A | 8/1983 | Portoghese et al. |
| 4,443,428 A | 4/1984 | Oshlack et al. |
| 4,451,470 A | 5/1984 | Ganti |
| 4,457,933 A | 7/1984 | Gordon et al. |
| 4,464,378 A | 8/1984 | Hussain et al. |
| 4,519,801 A | 5/1985 | Edgren |
| 4,573,995 A | 3/1986 | Chen et al. |
| 4,576,604 A | 3/1986 | Guittard et al. |
| 4,582,835 A | 4/1986 | Lewis et al. |
| 4,588,580 A | 5/1986 | Gale et al. |
| 4,597,961 A | 7/1986 | Etscorn |
| 4,606,909 A | 8/1986 | Bechgaard |
| 4,608,376 A | 8/1986 | Pasternak |
| 4,612,008 A | 9/1986 | Wong et al. |
| 4,626,539 A | 12/1986 | Aungst et al. |
| 4,655,766 A | 4/1987 | Theeuwes et al. |
| 4,661,492 A | 4/1987 | Lewis et al. |
| 4,719,215 A | 1/1988 | Goldberg |
| 4,730,048 A | 3/1988 | Portoghese et al. |
| 4,760,069 A | 7/1988 | Rzeszotarski et al. |
| 4,769,372 A | 9/1988 | Kreek et al. |
| 4,783,456 A | 11/1988 | Glassman |
| 4,785,000 A | 11/1988 | Kreek et al. |
| 4,795,327 A | 1/1989 | Gaylord et al. |
| 4,803,208 A | 2/1989 | Pasternak |

(Continued)

FOREIGN PATENT DOCUMENTS

| | | |
|---|---|---|
| AU | 9211180 | 9/1992 |
| CA | 2229621 | 9/1998 |

(Continued)

OTHER PUBLICATIONS

Pakkanen, Jukka. S. , University of Helsinki."Upregulation and Functionality of Neuronal Nicotinic Acetylcholine Receptors," Academic Dissertation, 2006.
Bodmeier, Roland, et al. "The influence of Buffer Species and Strength of Diltiazem HCl Release from Beads Coated with the Aqueous Cationic Polymer Dispersions, Eudragit RS, RL 30 D," Pharmaceutical Research, 13(1), 52-56, 1996.
Wagner, Karl G. et al "Influence of chloride ion exchange on the permeability and drug release of Eudragit RS 30 D films," Journal of Controlled Release, 82, (2002).
Felton, Linda A., et al. "Influence of Insoluble Excipients on Film Coating Systems," Drug Development and Industrial Pharmacy, 28(3), 225-243 (2002).
Knop, K., et al. "Influence of Surfactants of Different Charge and Concentration on Drug Release from Pellets Coated with an Aqueous Dispersion of Quaternary Acrylic Polymers," S.T.P. Pharma Sciences, 7(6), 507-512 (1997).

(Continued)

*Primary Examiner* — Susan Tran
(74) *Attorney, Agent, or Firm* — Stephanie J. Monaco

(57) ABSTRACT

Provided herein is a pharmaceutical composition comprising an antagonist, an agonist, a seal coat, and a sequestering polymer, wherein the antagonist, agonist, seal coat and at least one sequestering polymer are all components of a single unit, and wherein the seal coat forms a layer physically separating the antagonist from the agonist from one another. Methods for manufacturing such a pharmaceutical composition are also provided. Methods for treating pain using such compositions is also demonstrated.

14 Claims, 4 Drawing Sheets

(56) References Cited

U.S. PATENT DOCUMENTS

| | | |
|---|---|---|
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,846,199 A | 7/1989 | Rose |
| 4,861,598 A | 8/1989 | Oshlack et al. |
| 4,861,781 A | 8/1989 | Goldberg |
| 4,867,985 A | 9/1989 | Heafield et al. |
| 4,867,987 A | 9/1989 | Seth |
| 4,871,546 A | 10/1989 | Feltz et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,935,429 A | 6/1990 | Dackis et al. |
| 4,940,587 A | 7/1990 | Jenkins et al. |
| 4,954,298 A | 9/1990 | Yamamoto et al. |
| 4,957,681 A | 9/1990 | Klimesch et al. |
| 4,970,075 A | 11/1990 | Oshlack |
| 4,987,136 A | 1/1991 | Kreek et al. |
| 4,990,341 A | 2/1991 | Goldie et al. |
| 4,992,464 A | 2/1991 | Brooks et al. |
| 4,994,279 A | 2/1991 | Aoki et al. |
| 5,021,053 A | 6/1991 | Barclay et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A * | 9/1992 | Granger et al. ............... 424/449 |
| 5,189,064 A | 2/1993 | Blum et al. |
| 5,198,229 A | 3/1993 | Wong et al. |
| 5,202,128 A | 4/1993 | Morella et al. |
| 5,215,758 A | 6/1993 | Krishnamurthy |
| 5,219,858 A | 6/1993 | Parnell |
| 5,225,440 A | 7/1993 | London et al. |
| 5,226,331 A | 7/1993 | Thompson et al. |
| 5,236,714 A | 8/1993 | Lee et al. |
| 5,256,669 A | 10/1993 | Askanazi et al. |
| 5,266,574 A | 11/1993 | Zagon et al. |
| 5,273,760 A | 12/1993 | Oshlack et al. |
| 5,286,493 A | 2/1994 | Oshlack et al. |
| 5,312,389 A | 5/1994 | Theeuwes et al. |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,326,571 A | 7/1994 | Wright et al. |
| 5,330,766 A | 7/1994 | Morella et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,362,496 A | 11/1994 | Baker et al. |
| 5,376,384 A | 12/1994 | Eichel et al. |
| 5,376,662 A | 12/1994 | Ockert |
| 5,378,474 A | 1/1995 | Morella et al. |
| 5,385,903 A | 1/1995 | Steppuhn et al. |
| 5,403,595 A | 4/1995 | Kitchell et al. |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,451,408 A | 9/1995 | Mezei et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain et al. |
| 5,475,995 A | 12/1995 | Livingston |
| 5,478,573 A | 12/1995 | Eichel et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,507,277 A | 4/1996 | Rubsamen et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain et al. |
| 5,514,680 A | 5/1996 | Weber et al. |
| 5,521,213 A | 5/1996 | Prasit et al. |
| 5,529,787 A | 6/1996 | Merrill et al. |
| 5,529,790 A | 6/1996 | Eichel |
| 5,529,813 A | 6/1996 | Kobsa et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,565,455 A | 10/1996 | Bjork et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain et al. |
| 5,585,348 A | 12/1996 | Crain et al. |
| 5,591,452 A | 1/1997 | Miller et al. |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,629,011 A | 5/1997 | Illum |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,725,883 A | 3/1998 | Staniforth et al. |
| 5,763,452 A | 6/1998 | Miller et al. |
| 5,767,125 A | 6/1998 | Crain et al. |
| 5,780,057 A | 7/1998 | Conte |
| 5,780,479 A | 7/1998 | Kim |
| 5,800,836 A | 9/1998 | Morella et al. |
| 5,811,126 A | 9/1998 | Krishnamurthy |
| 5,834,024 A | 11/1998 | Heinichke et al. |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Demopulos et al. |
| 5,860,950 A | 1/1999 | Demopulos et al. |
| 5,866,164 A | 2/1999 | Kuczynski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,919,473 A | 7/1999 | Elkhoury |
| 5,935,975 A | 8/1999 | Rose et al. |
| 5,942,241 A | 8/1999 | Chasin et al. |
| 5,952,005 A | 9/1999 | Olssen et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,954 A | 10/1999 | Foss |
| 5,998,434 A | 12/1999 | Mitch et al. |
| 6,024,982 A | 2/2000 | Oshlack et al. |
| 6,033,687 A | 3/2000 | Heinicke et al. |

(56) References Cited

U.S. PATENT DOCUMENTS

| | | |
|---|---|---|
| 6,068,855 A | 5/2000 | Leslie et al. |
| 6,077,532 A | 6/2000 | Malkowska et al. |
| 6,077,533 A | 6/2000 | Oshlack et al. |
| 6,103,258 A | 8/2000 | Simon |
| 6,103,261 A | 8/2000 | Chasin et al. |
| 6,103,734 A | 8/2000 | Legarda Ibanez |
| 6,143,322 A | 11/2000 | Sackler et al. |
| 6,143,328 A | 11/2000 | Heafield et al. |
| 6,149,940 A | 11/2000 | Maggi et al. |
| 6,156,343 A | 12/2000 | Morita et al. |
| 6,162,467 A | 12/2000 | Miller et al. |
| 6,194,000 B1 | 2/2001 | Smith et al. |
| 6,197,348 B1 | 3/2001 | Morella et al. |
| 6,210,714 B1 | 4/2001 | Oshlack et al. |
| 6,214,385 B1 | 4/2001 | Heinicke et al. |
| 6,228,863 B1 | 5/2001 | Palermo et al. |
| 6,254,887 B1 | 7/2001 | Miller et al. |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,306,438 B1 | 10/2001 | Oshlack et al. |
| 6,316,031 B1 | 11/2001 | Oshlack |
| 6,326,027 B1 | 12/2001 | Miller et al. |
| 6,335,033 B2 | 1/2002 | Oshlack et al. |
| 6,375,957 B1 | 4/2002 | Kaiko et al. |
| 6,387,404 B2 | 5/2002 | Oshlack et al. |
| 6,399,096 B1 | 6/2002 | Miller et al. |
| 6,475,494 B2 | 11/2002 | Kaiko et al. |
| 6,495,120 B2 | 12/2002 | McCoy et al. |
| 6,627,635 B2 | 9/2003 | Palermo et al. |
| 6,635,277 B2 | 10/2003 | Sharma et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,765,010 B2 | 7/2004 | Crain et al. |
| 6,865,444 B2 | 3/2005 | Howard |
| 6,872,407 B2 | 3/2005 | Notario et al. |
| 6,878,717 B2 | 4/2005 | DeCorte et al. |
| 6,905,709 B2 | 6/2005 | Oshlack et al. |
| 7,056,532 B1 | 6/2006 | Kabanov et al. |
| 7,067,151 B1 | 6/2006 | Heinicke et al. |
| 7,070,806 B2 | 7/2006 | Oshlack et al. |
| 7,081,255 B2 | 7/2006 | Baert et al. |
| 7,101,574 B1 | 9/2006 | Criere et al. |
| 7,125,561 B2 | 10/2006 | Sackler |
| 7,144,587 B2 | 12/2006 | Oshlack et al. |
| 7,163,696 B2 | 1/2007 | Davis et al. |
| 7,172,767 B2 | 2/2007 | Kaiko et al. |
| 7,202,240 B2 | 4/2007 | Gilkerson et al. |
| 7,241,458 B1 | 7/2007 | Verreck et al. |
| 7,268,138 B2 | 9/2007 | Kalish et al. |
| 7,332,182 B2 | 2/2008 | Sackler |
| 7,338,928 B2 | 3/2008 | Lau et al. |
| 7,384,653 B2 | 6/2008 | Wright, IV et al. |
| 7,402,607 B2 | 7/2008 | Smith et al. |
| 7,419,686 B2 | 9/2008 | Kaiko et al. |
| 7,682,633 B2 | 3/2010 | Matthews et al. |
| 7,682,634 B2 | 3/2010 | Matthews et al. |
| 7,744,924 B2 | 6/2010 | Heinicke |
| 2002/0010127 A1 | 1/2002 | Oshlack et al. |
| 2002/0058673 A1 | 5/2002 | Kaiko et al. |
| 2003/0004177 A1 | 1/2003 | Kao et al. |
| 2003/0026838 A1 | 2/2003 | Farrell |
| 2003/0049317 A1 | 3/2003 | Lindsay |
| 2003/0059397 A1 | 3/2003 | Hughes |
| 2003/0064099 A1 | 4/2003 | Oshlack et al. |
| 2003/0064122 A1 | 4/2003 | Goldberg et al. |
| 2003/0065002 A1 | 4/2003 | Caruso et al. |
| 2003/0068276 A1 | 4/2003 | Hughes et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0073714 A1 | 4/2003 | Breder et al. |
| 2003/0091635 A1 | 5/2003 | Baichwal et al. |
| 2003/0124061 A1 | 7/2003 | Roberts |
| 2003/0124185 A1 | 7/2003 | Oshlack et al. |
| 2003/0143269 A1 | 7/2003 | Oshlack et al. |
| 2003/0157167 A1 | 8/2003 | Kao et al. |
| 2003/0157168 A1 | 8/2003 | Breder et al. |
| 2003/0190362 A1 | 10/2003 | Sackler et al. |
| 2004/0013716 A1* | 1/2004 | Gale et al. ............. 424/449 |
| 2004/0024004 A1 | 2/2004 | Sherman et al. |
| 2004/0024006 A1 | 2/2004 | Simon |
| 2004/0092542 A1 | 5/2004 | Oshlack et al. |
| 2004/0110781 A1 | 6/2004 | Harmon et al. |
| 2004/0131552 A1* | 7/2004 | Boehm ................. 424/10.1 |
| 2004/0176402 A1 | 9/2004 | Oshlack et al. |
| 2004/0180916 A1 | 9/2004 | Levine |
| 2004/0186121 A1 | 9/2004 | Oshlack et al. |
| 2004/0202717 A1 | 10/2004 | Mehta |
| 2004/0241218 A1 | 12/2004 | Tavares et al. |
| 2005/0095291 A1 | 5/2005 | Oshlack et al. |
| 2005/0142203 A1 | 6/2005 | Heinicke |
| 2005/0163856 A1 | 7/2005 | Maloney et al. |
| 2005/0181046 A1 | 8/2005 | Oshlack et al. |
| 2005/0191244 A1 | 9/2005 | Bartholomaus et al. |
| 2005/0192309 A1 | 9/2005 | Palermo et al. |
| 2005/0245557 A1 | 11/2005 | Schoenhard |
| 2006/0039970 A1 | 2/2006 | Oshlack et al. |
| 2006/0099258 A1 | 5/2006 | Heinicke |
| 2006/0099259 A1 | 5/2006 | Heinicke |
| 2006/0104909 A1 | 5/2006 | Vaghefi et al. |
| 2006/0110327 A1 | 5/2006 | Emigh et al. |
| 2006/0159744 A1 | 7/2006 | Alaux et al. |
| 2006/0182801 A1 | 8/2006 | Breder et al. |
| 2006/0182891 A1 | 8/2006 | Usoskin et al. |
| 2006/0198881 A1 | 9/2006 | Howard et al. |
| 2006/0204575 A1 | 9/2006 | Feng et al. |
| 2006/0257460 A1 | 11/2006 | Jansen et al. |
| 2006/0269605 A1 | 11/2006 | Lizio et al. |
| 2007/0014732 A1 | 1/2007 | Sackler |
| 2007/0020339 A1 | 1/2007 | Bear |
| 2007/0042045 A1 | 2/2007 | Lizio et al. |
| 2007/0134329 A1 | 6/2007 | Heinicke |
| 2007/0185145 A1 | 8/2007 | Royds |
| 2007/0196396 A1 | 8/2007 | Pilgaonkar et al. |
| 2007/0243245 A1 | 10/2007 | Heinicke |
| 2007/0243250 A1 | 10/2007 | Heinicke |
| 2007/0243252 A1 | 10/2007 | Heinicke |
| 2008/0069871 A1 | 3/2008 | Vaughn et al. |
| 2008/0069881 A1 | 3/2008 | Caruso et al. |
| 2008/0075768 A1 | 3/2008 | Vaughn et al. |
| 2008/0075770 A1 | 3/2008 | Vaughn et al. |
| 2008/0075771 A1 | 3/2008 | Vaughn et al. |
| 2008/0166405 A1 | 7/2008 | Mehta |
| 2008/0233156 A1 | 9/2008 | Matthews et al. |
| 2008/0233197 A1 | 9/2008 | Matthews et al. |
| 2008/0280975 A1 | 11/2008 | Badul |
| 2008/0306104 A2 | 12/2008 | Oshlack |
| 2008/0318993 A1 | 12/2008 | Ahdieh |
| 2008/0318994 A1 | 12/2008 | Ahdieh |
| 2009/0028942 A1 | 1/2009 | Kandi et al. |
| 2009/0131466 A1 | 5/2009 | Liang et al. |
| 2009/0162450 A1 | 6/2009 | Matthews et al. |
| 2009/0162451 A1 | 6/2009 | Matthews et al. |
| 2009/0238869 A1 | 9/2009 | Heinicke |
| 2010/0151014 A1 | 6/2010 | Liang et al. |
| 2010/0152221 A1 | 6/2010 | Liang et al. |
| 2010/0159018 A1 | 6/2010 | Heinicke |

FOREIGN PATENT DOCUMENTS

| | | |
|---|---|---|
| DE | 2222039 | 11/1972 |
| EP | 0074105 | 3/1983 |
| EP | 0144243 A1 | 6/1985 |
| EP | 0185472 A1 | 6/1986 |
| EP | 0193355 A2 | 9/1986 |
| EP | 0220805 A3 | 5/1987 |
| EP | 0232877 A2 | 8/1987 |
| EP | 0205282 | 12/1987 |
| EP | 0352361 | 1/1990 |
| EP | 502642 | 9/1992 |
| EP | 0502642 A1 | 9/1992 |
| EP | 1041987 B1 | 4/2006 |

(56) References Cited

FOREIGN PATENT DOCUMENTS

| | | |
|---|---|---|
| GB | 751767 | 7/1956 |
| GB | 769517 | 3/1957 |
| GB | 791644 | 3/1958 |
| GB | 808269 | 1/1959 |
| GB | 2196848 | 10/1987 |
| WO | WO 8303197 | 9/1983 |
| WO | WO 8701282 A2 | 3/1987 |
| WO | WO 9004965 A1 | 5/1990 |
| WO | WO 9406426 A1 | 3/1994 |
| WO | WO 9503804 A1 | 2/1995 |
| WO | WO 9602251 A1 | 2/1996 |
| WO | WO 9732573 | 9/1997 |
| WO | WO 9733566 A2 | 9/1997 |
| WO | WO 9825613 A2 | 6/1998 |
| WO | WO 9835679 A1 | 8/1998 |
| WO | 9930714 A1 | 6/1999 |
| WO | WO 9932119 | 7/1999 |
| WO | WO 9932120 A1 | 7/1999 |
| WO | WO 0001377 A2 | 1/2000 |
| WO | WO 0038649 A1 | 7/2000 |
| WO | WO 0132180 A2 | 5/2001 |
| WO | WO 0137785 A2 | 5/2001 |
| WO | WO 0152851 A1 | 7/2001 |
| WO | WO 0158447 A1 | 8/2001 |
| WO | WO 0158451 | 8/2001 |
| WO | WO 0168080 A2 | 9/2001 |
| WO | WO 0185257 A2 | 11/2001 |
| WO | WO 0193852 A2 | 12/2001 |
| WO | WO 02092059 | 11/2002 |
| WO | WO 2004026256 | 4/2004 |
| WO | WO 2004026283 | 4/2004 |
| WO | WO 2004/091512 | 10/2004 |
| WO | WO 2004093801 | 11/2004 |
| WO | WO 2005018616 | 3/2005 |
| WO | WO 2005055981 | 6/2005 |
| WO | WO 2005081825 | 9/2005 |
| WO | WO 2006130471 | 12/2006 |
| WO | WO 2008/011169 | 1/2008 |
| WO | WO 2009/088673 | 7/2009 |

OTHER PUBLICATIONS

Rao, et al., "Effect of Sodium Lauryl Sulfate on the Release of Rifampicin from Guar Gum Matrix", Indian J. of Pharm. Sci. pp. 404-406 (Sep.-Oct. 2000).
Abdulla, et al., "Axotomy reduces the effect of analgesic opioids yet increases the effect of nociceptin on dorsal root . . . ", J. Neuro Sci 1998, p. 9685-9694, vol. 18.
Alvarez-Fuentes, et al., "Effectiveness of Repeated Administration of a New Oral Naltrexone . . . "; J. Pharm Pharmacol (2001), p. 1201-1205, v. 53.
Alvarez-Fuentes, et al., "Preclinical Study of an Oral Controlled Release Naltrexone Complex in Mice"; J. Pharm Pharmacol (2000), p. 659-663, v. 52.
Barton et al., "Intranasal Administration of Naloxone by Paramedics"; Prehospital Emergency Care (2002), p. 54-58, vol. 6, No. 1.
Baum et al., "The Impact of the Addition of Naloxone on the Use and Abuse of Pentazocine"; Public Health Reports, (1987) p. 426-429. v. 102(4).
Blachly, M.D., "Naloxone in Opiate Addiction"; Current Psychiatric Therapies (1976) p. 209-213.
Bloom et al., Clinical Studies with Naloxone/Methadone in a Ratio of 1:20; 5.sup.th National Conference on Methadone Treatment (1973), p. 1342-1349, vol. 2.
Brennscheidt et al., Pharmacokinetics of Nortilidine and Naloxone . . . , Arzneim.-Forsch/Drug Res. (2000), p. 1015-1022, vol. 50.
Bigelow et al., "Abuse Liability Assessment . . . "; Dept. of Psychiatry and Behavioral Sciences—The Johns Hopkins University School of Medicine. p. 145-149.
Bromm, et al., "A Sensitive Method to Evaluate Effects of Analgesics in Man"; Meth and Find Exptl Clin Pharmacol, (1983) p. 545-551, v. 5 No. 8.

Bullingham, et al., "Clinical Pharmacokinetics of Narcotic Agonist-Antagonist Drugs"; Clinical Pharm. (1983) p. 332-343, v. 8.
Cherny, N.., "Opioid Analgesics"; Drugs (1996), p. 713-737, v. 51 (5).
Fraser, Albert D., et al., "Clinical Toxicology of Drugs Used in the Treatment of Opiate Dependency"; Clinical Toxicology I, (1990), p. 375-386, vol. 10, No. 2.
Caruso et al., "Methadone and Naloxone in Combination (Naldone. RTM.) for the Treatment of Heroin Addicts"; Bristol Laboratories, p. 1336-1341F.
Crabtreeet al., "Review of Naltrexone, a long-acting opiate antagonist"; Clinical Pharmacy, (1984) p. 273-280, vol. 3.
Crain et al., "Ultra-low concentrations of naloxone selectively antagonize excitatory . . . " Proc. Natl. Acad. Sci (1995), p. 10540-10544, vol. 92.
Czarnecki et al. "The Use of Photography in the Clinical Evaluation of Unequal Pupils." Canad J Ophthal 1979, p. 297-302, v. 14.
Driscoll, P. "Comparitive Toxicity for Mice . . . " Praeventimedizin, 1972, p. 211-213, v. 17 (4).
Gal et al., "Prolonged Blockade of Opioid Effect with Oral Nalmefene"; Clin Pharmacol Ther. (1986) p. 537-542.
Ghodse, et al., "Opioid analgesics and narcotic antagonists"; Side Effects of Drugs (2000), p. 96-113, Annual 23, Ch. 8.
Gonzalez et al., "Naltrexone: A Review of its Pharmacodynamic and Pharmacokinetic Properties and Therapeutic . . . " Drugs (1988), p. 192-213., v. 35.
Goodman et al., Pharmacological Basis of Therapeutics, 3rd Edition, 1965, pp. 274-279.
Gawin, FH. "Chronic Neuropharmacology of Cocaine", Jr. of Clin. Psychiatry, Feb. 1988, p. 11-16. v. 49(2).
Gan et al., "Opioid-Sparing Effects of a Low-Dose Infusion of Naloxone in Patent-Administered Morphine Sulfate," Anesthesiology (1997), 1075-1080, v. 87(5).
Glick et al "Titration of Oral nicotine Intake . . . ". Nature, 1971, p. 207-208, v. 233.
Hanson, Analgesic, Antipyretic and Anti-Inflammatory Drugs in Remington's Science and Practice of Pharmacy, 1995, p. 1207, v. 2.
Harris et al. "Protection Againts Disipropyfluorophosphate Intox." Arch. of Pharm. 1984. p. 64-69, v.327.
Harris, LS. Central Neuropunoral Systems, Fed Proceed., Jan.-Feb. 1970, p. 28-32, v. 20:1.
Hawkes et al., "Effect of an enteric-release formulation of naloxone on intestinal transit in volunteers taking codeine"; Aliment Pharm Ther (2001), p. 625-630, vol. 15.
Levine, et al."Potentiation of Pentazocine Analgesia by Low-dose Naloxone", J. Clin. Invest.,1988, p. 1574-1577, vol. 82.
Hogger et al., "Comparison of tilidine/naloxone, tramadol and bromfenac in experimental pain . . . ", International J. Clin Pharm and Ther (1999), p. 377-385, vol. 37, No. 8.
Hussain et al., "Buccal and oral bioavailability of naloxone and naltrexone in rats"; (1987), p. 127-130, vol. 36.
King et al., "Naltrexone Biotransformation and Incidence of Subjective Side Effects: A Preliminary Study"; Alcoholism: Clin and Exp Res (1997), p. 906-909, vol. 21, No. 5.
Kurland et al., "Naloxone and the Narcotic Abuser: A Controlled Study of Partial Blockade"; Inter. J. of the Addictions (1974), p. 663-672, vol. 9, No. 5.
Martin et al., "Bioavailability Investigation of a New Tilidine/Naloxone Liquid Formulation Compared . . . "; Arzneim.-Forsch./Drug Res. (1999),p. 599-607, vol. 49.
Lehmann et al., "Influence of Naloxone on the Postoperative Analgesic and Respiratory Effects of Buprenorphine"; Eur J. Clin. Pharm. (1988), 343-352, vol. 34.
Jasinski D.R., "Assessment of the Abuse Potentiality of Morhinelike Drugs (Methods Used in Man)"; Drug Addiction (1977) p. 197-258.
Johnson et al., "Buprenorphine and Naloxone for Heroin Dependence"; Substance Use Disorders(2000) p. 519-526.
Tai et al., "Naltrexone: An Antagonist Therapy for Heroin Addiction"; NIDA (1997) 5 pages.
Stine et al., "Reduction of Opiate Withdrawal-like Symptoms by Cocaine Abuse during . . . "; Am. J. Drug Alcohol Abuse (1994), p. 445-458, vol. 20, (4).

(56) References Cited

OTHER PUBLICATIONS

Stine et al., "Use of Drug Combinations in Treatment of Opioid Withdrawal"; J. of Clinical Psych. (1992), p. 203-209, vol. 12, No. 3.
Suzuki, et al., Morphine conditioned place preference after chronic treatment with naloxone . . . : Research Communications in Substances of Abuse. (1991), vol. 12(3), p. 191-131.
Tennant et al "Withdrawal From Nicotine Dependence . . . "., NIDA Research Monograph, 1985, p. 291-297, v. 55. J. Pharmacol. Exp. Ther.
Walsh et al., "Effects of Naltrexone on Response to Intravenous Cocain, Hydromorphone and their Combination in Humans," (1996). 279:524-538.
Way et al., "Responsivity to Naloxone during Morphine Dependence"; Annals New York Academy of Sciences, p. 252-261.
Wodak Alex, "Drug Treatment for Opioid Dependence"; Australian Prescriber (2001), p. 4-6, vol. 24, No. 1.
Parwartikar et al., "Naloxone-Methadone Combination for the Treatment of Opiate Dependence"; Missouri Institute of Psychiatry, p. 1350-1354.
Wikler et al., N-Allylnormorphine: Effects of single doses and precipitation of acute . . . N-Allylnormorphine During Narcotic Addiction (1953) p. 8-20.
Vaccarino et al., Pain, 1989, p. 103-109, v. 36.
Yuan et al., Clinical Trials and Therapeutics, (Apr. 1997) 467-475, v. 61.
Zaks et al., "Naloxone Treatment of Opiate Dependence"; JAMA (1971), p. 2108-2110, vol. 215, No. 13.
Alvarez-Fuentes, et al., "Study of a complexation process between naltrexone and Eudragit . . . ", Int'l Journal of Pharmaceutics 148 (1997) 219-230.
W.K. Asbeck, et al. "Critical Pigment Volume Relationships", Ind. Eng. Chem., 1949, (41), 1470-1475.
Bashaw, et al. "Relative bioavailability of controlled-release oral morphine sulfate . . . ", Int'l Journal of Clinical Pharmacology and Therapeutics, vol. 33 No. 9 1995(524-529).
Bierwagen, et al., "Studies of the Effects of Particle Size Distribution on the Packing Efficiency of Particles", Powder Tech., 10(1974) 111-119.
Bodmeier, et al., "Dry and wet strengths of polymeric films prepared from an aqueous colloidal polymer dispersion, Eudragit RS30D", Int'l Journ. of Pharma., 96(1993) 129-138.
Bodmeier, et al. "Mechanical Properties of Dry and Wet Cellulosic and Acrylic Films Prepared from Aqueous Colloidal Polymer . . . ", Pharmaceutical Research, vol. 11, No. 6, (1994), 882-888.
Childs, et al. "Crystal Engineering Approach to Forming Cocrystals of Amine Hydrochlorides With Organic Acids . . . "J.AM.Chem. SOc. 2004, 126 p. 13335-13342.
Fernandez-Arevalo, et al., "Water-Insoluble Complexes of Morphine and Carteolol-Eudragit L.A. . . . ", Supplied by The British Library, p. 158-181.
Gould, "Salt selection for basic drugs", International Journal of Pharmaceutics, 33 (1986) 201-207.
Holgado, et al., "Physical characterization of carteolol: Eudragit L binding interaction", International Journal of Pharmaceutics 114 (1995) p. 13-21.
Judson, et al., "Chapter 1. Uses of Naloxone in the Diagnosis and Treatment of Heroin Addiction", p. 1-13.
Kelly, et al., "Prevalence and characteristics of opioid use in the US adult population", Pain 138 (2008) p. 507-513.
Lang, et al., "Cardiovascular responses to injections of cholinomimetic drugs into the cerebral ventricles . . . ", Br. J. Pharmac. (1973), 47, p. 196-205.
McGinity, et al., "In Vitro Adsorption of Various Phmarmaceuticals to Montmorillonite", Journal of Pharmaceutical Sciences, vol. 65, Jun. 1976 p. 896-902.
Mendelson, et al. "Buprenorphine and naloxone interactions in opiate-dependent volunteers", Clinical Pharmacology & Therapeutics, (1996) p. 105-114.
Meyer, et al. "A Behavioral Paradigm for the Evaluation of Narcotic Antagonists", Arch. Gen Psychiatry, vol. 33 (1976), pp. 371-377.
Pakkanen, "Upregulation and Functionality of Neuronal Nicotinic Acetylcholine Receptors", Div. of Pharm. and Toxicology Faculty Pharm.Univ. Helsinki, p. 1-89.
Patel, et al. "Nanoclays for Polymer nanocomposites, paints, inks, greases and cosmetics formulations, . . . ", Bull. Mater. Sci., vol. 29, No. 2 (2006) pp. 133-145.
Peachey, et al. "Assessment of Opioid Dependence with Naloxone", British Journal of Addiction (1988) 83, pp. 193-201.
Sunshine, et al. "Analgesic Efficacy of Pentazocine Versus a Pentazocine-Naloxone Combination Following Oral Administration", The Clinical Journal of Pain (1988) pp. 35-40.
Rogers, et al., Glass Transitions of the Poly-(n-Alkyl Methacrylates), J. Phys. Chem., 1957, 61 (7), pp. 985-991.
Bierwagen et al., "Recent Studies of Particle Packing in Organic Coatings"; Progress in Organic Coatings., 35 (1999) pp. 1-9.
Okhamafe, et al., "Interaction Phenomena in Pharmaceutical Film Coating and Testing Methods" Int. J. Pharmaceutics; vol. 39 (1987) pp. 1-21.
Farris, R.J.; "Prediction of the Viscosity of Multimodal Suspensions from Unimodal Viscosity Data" Trans. Soc. Rheology, vol. 12, No. 2, (1968) pp. 281-301.
Knop, "Influence of Buffer Solution Composition on Drug Release from Pellets Coated with Neutral and Quaternary . . . ", Euro. J. Pharm Sci., vol. 4, (1996) pp. 293-300.
Ozturk, et al. "Mechanism of Release from Pellets Coated with an Ethylcellulose Based Film" J. Cont. Release, vol. 14, (1990) pp. 203-213.
Briscoe, B. et al. "Rheology of Solvent-Cast Polymer Films", Journal of Applied Polymer Science, vol. 28 (1983) No. 3, pp. 3827-3848.
Michalson, A.W, "Ion Exchange", Chem. Engineering, Mar. 18, 1963 pp. 163-182.
Hercules Inc., "Physical and Chemical Properties", pp. 1-34.
Dressman J. et al., "Dissolution Testing as a Prognostic Tool for Oral Drug Absorption: . . . " Pharm. Research, 15 (1) pp. 11-22 (1998).
Galia, et al., "Evaluation of Various Dissolution Media for Predicting In Vivo Performance of Class I and II Drugs" Pharm. Research, 15 (5) pp. 698-705 (1998).
Vertzoni, et al., "Dissolution media simulating the intralumenal composition of the small intestine: . . . " J. of Pharmacy and Pharm., vol. 56, 2004; pp. 453-462.
Pederson, et al., "Dissolution of Hydrocortisone in Human and Simulated Intestinal Fluids" Pharm. Research, vol. 17, No. 2, 2000; pp. 183-189.
Powell, et al., "Application of the critical precipitation essay to complex samples: aluminum binding . . . " Chem. Speciation and Bioavailability; vol. 16, No. 3, 2004, pp. 97-104.
Pharm. Coatings Bulletin 102-3, "Influence of Plasticizers on the Dissolution and Physical Properties of Ethyl Cellulose Films and Coated Beads" pp. 1-8 (1995).
Hjartstam, et al. "Effect of Hydroxyl Group Content in Ethyl Cellulose on Permeability in Free Films and Coated Membranes", J. Appl. Polymer Scien., V. 72, pp. 529-535 (1999).
Feller, et al. "Evaluation of Cellulose Ethers for Conservation", The Getty Conserv. Inst., (1990) pp. 1-161.
Rhom GmbH & Co. KG, Specifications and test methods for Eudragit RL 100 and Eudragit RL PO Eudragrit RS 100 and Eudragit RS PO, (Sep. 2004), pp. 1-4.
Lehmann, et al. "Practical Course in Film Coating of Pharmaceutical Dosage Forms with EUDRAGIT", Pharma Polymers (2001) pp. 1-199.
Blackie Academic and Prof. "Introduction to Surfactant Analysis", (1992) pp. 1-3.
Kaufman, et al.,"Narcotic and Narcotic Antagonist pKa's and Partition Coefficients and Their Significance in Clinical Practice", Drug and Alcohol Depend. 1 (1975-76) pp. 103-114.
van der Wel,"Moisture in Organic Coatings—a review", Progress in Organic Coatings 37 (1999) pp. 1-14.
Donbrow et al. Gradation of microcapsule wall porosity by deposition of polymer mixtures (Eudragit RL and Eurdagit RS). Phase Separation of Polymer Mixtures and Effects of External Media and Conditions on Release. J. Microencapsulation. vol. 12, No. 3, pp. 273-285 (1995).

(56) References Cited

OTHER PUBLICATIONS

Weinberg et al. Sublingual absorption of selected opioid analgesics. Clin. Pharmacol. Ther. 44:335-340 (1988).

Weinhold et al. Buprenorphine alone and in combination with naloxone in nondependent humans. Drug and Alcohol Dependence, 30:263:274 (1992).

Wells, et al. Effect of Anionic Surfactants on the Release of Clorpheniramine Malate from an Inert, Heterogeneous Matrix. Drug Development and Industrial Pharmacy, 18(2):175-186 (1992).

Heng, P.W. S., et al., Drug Dev. Ind. Pharm. (2004), 30(2); pp. 213-220.

Non-Pareil Sugar Spheres 2003 Information Sheet, JRS Pharma LP, pp. 1-4, (Mar. 2003).

Http://www.merck.com/mmpe/print/sec20/ch304/ch304b.html, Drug-Receptor Interactions: Pharmacodynamics: Merck Manual Professional, accessed May 6, 2010.

Goggins et al. "What WOMAC Pain Score Should make a Patient Eligible for a Trial in Knee Osteorarthritis?", The Journal of Rheumatology, Mar. 1, 2005, vol. 32, No. 3, pp. 540-542.

Ferrari, et al. "Serum time course of naltrexone and 6b-naltrexol levels during long term treatment in durg addits", Drug and alcohol Dependence, vol. 52, (1998) pp. 211-220.

Garner-Nix, JAMC, Oct. 28, 2003 902 and 904 (2 pages).

Mott et al., Cancer Therapy 2, 365-374 (2004) 1-10.

Heinicke, G., Drug release from cationic polymethacrylate-coating diltiazem particles, Diss. Abstr. Int., B 2007, 68(6).

Heinicke, G., et al., Drug Release from Ammonio-Methacrylate-Coated Diltiazem Particles: Influence of the Reservoir on Membrane Behavior, Pharmaceutical Development and Technology, 2007, p. 473-479, 12(5).

Heinicke, G., et al., The Influence of Surfactants and Additives on Drug Release from a Cationic Eudragit Coated Multiparticulate Diltiazem Formulation, Pharmaceutical Development and Technology, 2007, p. 381-389, 12(4).

Heinicke, G., et al., Ammonio Polymethacrylate-Coated Diltiazem: Drug Release from Single Pellets, Media Dependence, and Swelling Behavior, Pharmaceutical Development and Technology, 2007, p. 285-296, 12(3).

Heinicke, G., et al., Assessment of dynamic image analysis as a surrogate dissolution test for a coated multiparticulate product, Pharmaceutical Development and Technology, 2006, p. 403-408, 11(4).

Heinicke, G., et al., The effects of substrate size, surface area, and density on coat thickness of multi-particulate dosage forms, Pharmaceutical Development and Technology, 2005, p. 85-96, 10(1).

Heinicke, G., et al., Particle Size Distributions of Inert Spheres and Pelletized Pharmaceutical Products by Image Analysis, Pharmaceutical Development and Technology, 2004, p. 359-367, 9(4).

Fassihi, R. A., et al., Potential Use of magnesium Stearate and Talc as Dissolution Retardants in the Development of Controlled Drug Delivery Systems, Pharm Ind, 1994, p. 579-583, 56(6).

Fassihi, R., et al., Application of Response Surface Methodology to Design Optimization in Formulation of a Typical Controlled Release System, Drugs made in Germany, 1996, p. 122-126, 39(4).

Schultz, P., et al., A new multiparticulate delayed release system. Part II: Coating formulation and properties of free films, Journal of Controlled Release, 1997, p. 191-199, 47.

Kibbe, A. H. "Talc." Pharmaceutical Excipients. MedicineComplete, Feb. 3, 2009. Web. <http://www.medicinescomplete.com/mc/excipients/current/1001947358.htm?q=talc>.

Ghebre-Sellassie I, Nesbitt RU, Wang J. Eudragit aqueous dispersions as pharmaceutical controlled release coatings. In: McGinity JW, editor. Aqueous polymeric coatings for pharmaceutical dosage forms. New York: Marcel Dekker, Inc; 1997 (Re-print). p. 77-96.

Knop, K. Influence of buffer solution composition on drug release from pellets coated with neutral and quaternary acrylic polymers and on swelling of free polymer films. Eur J Pharm Sci. 1996;4:293-300.

Maejima T, et al., Influence of film additives on stabilizing drug release rates from pellets coated with acrylic polymers. Pharm Dev Technol. 2001;6(2):211-221.

Wagner, KG, et al., Influence of chloride ion exchange on the permeability and drug release of Eudragit RS 30D films. J Control Release. 2002;82:385-397.

Wagner, KG, et al. Anion-induced water flux as drug release mechanism through cationic Eudragit RS 30D film coatings. AAPS Journal. 2005;7(3):E668-E677.

Notification of Certifications of Invalidity and/or Noninfringement for US Patents Nos. 7,682,634; 7,682,634 and 7,815,934 Pursuant to §505*j)(2)(B)(iv) of the Federal Food, Drug, and cosmetic Act dated Aug. 24, 2011, Watson notice to Alpharma Pharmaceuticals, LLC.

Report on the Filing or Determination of an Action Regarding a Patent or Trademark pursuant to 35 USC 290, filed Oct. 6, 2011.

Complaint filed by Pfizer Inc, Alpharma Pharmaceuticals, LLC and King Pharmaceuticals, Inc., dated Oct. 6, 2011.

\* cited by examiner

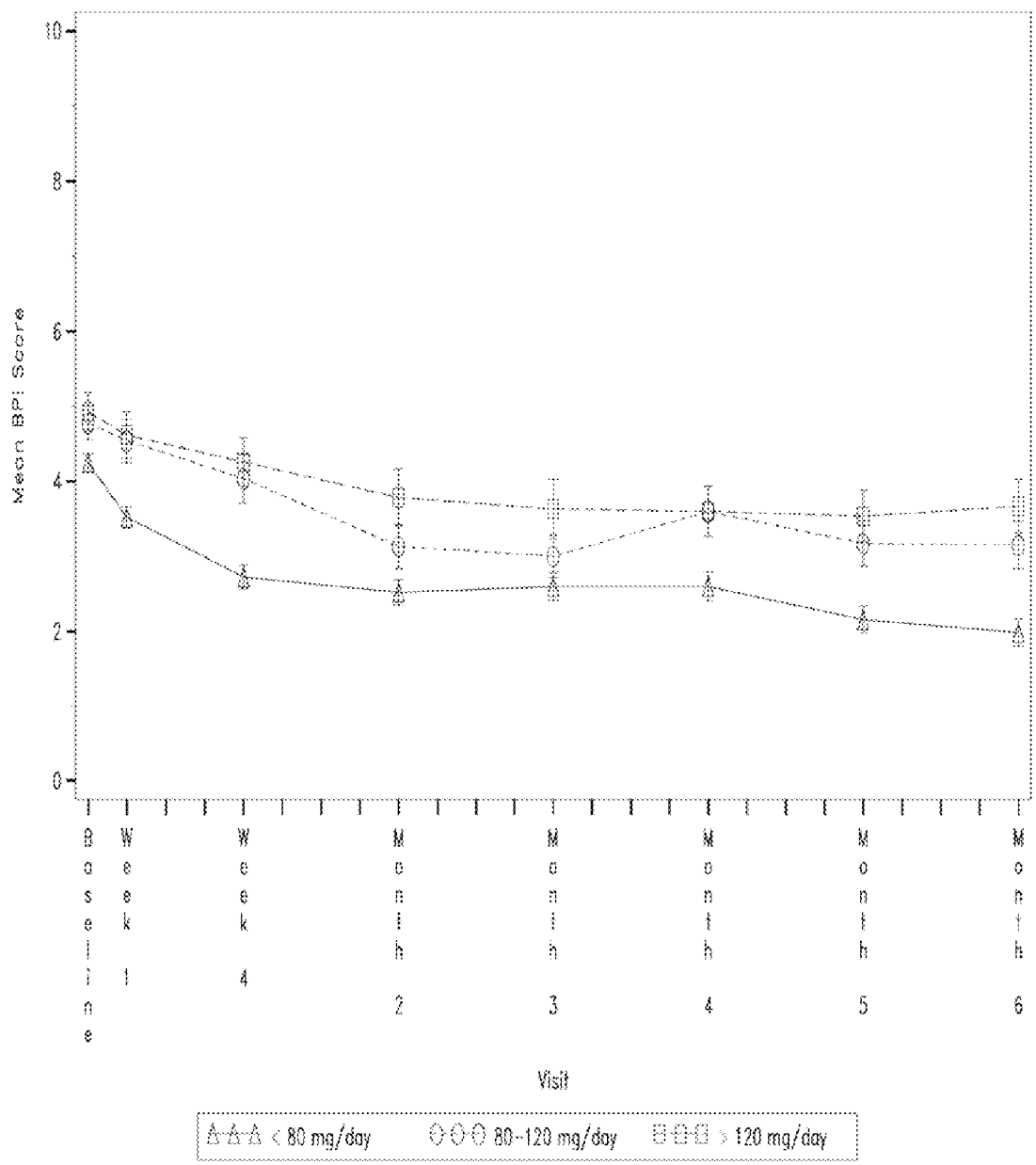

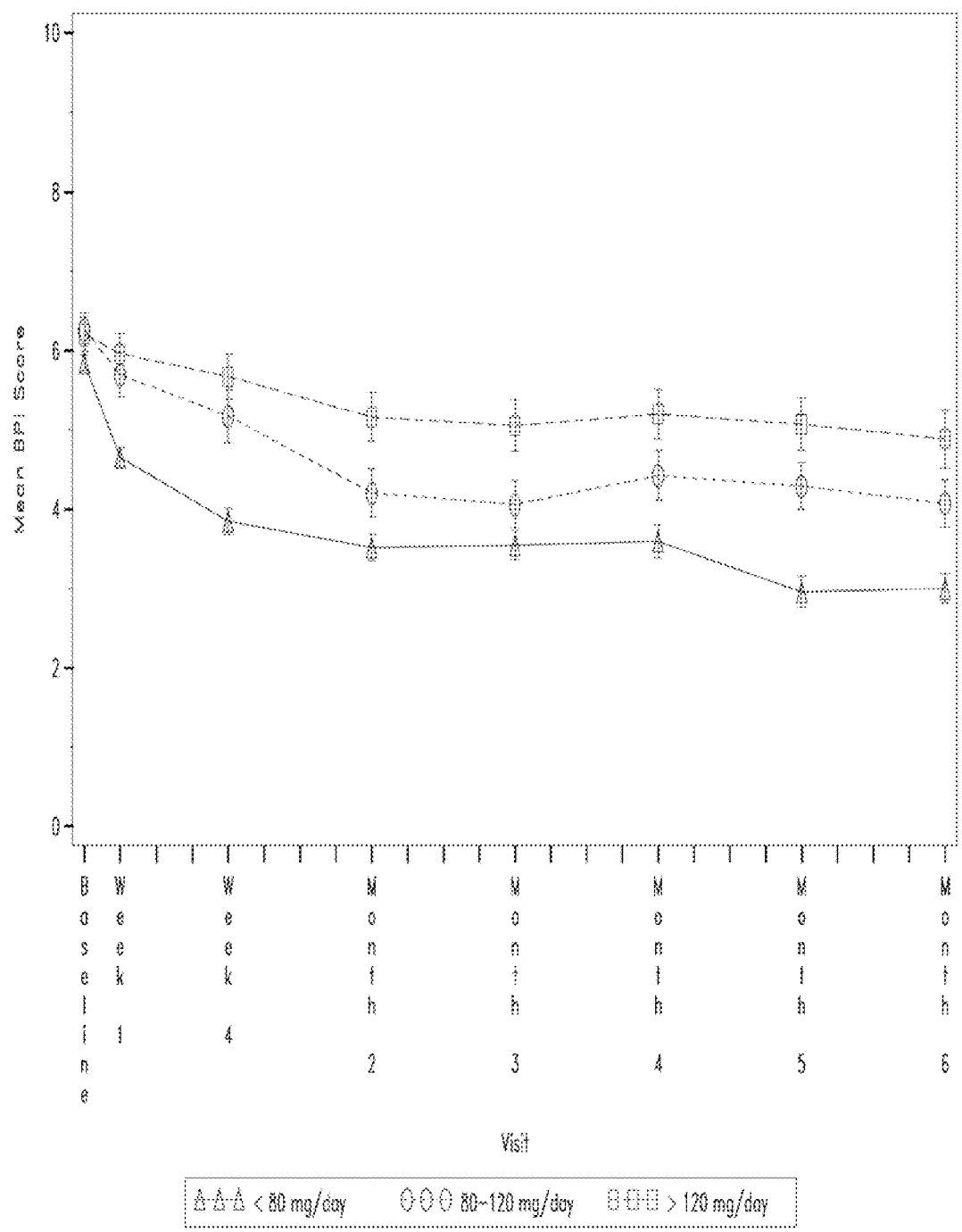

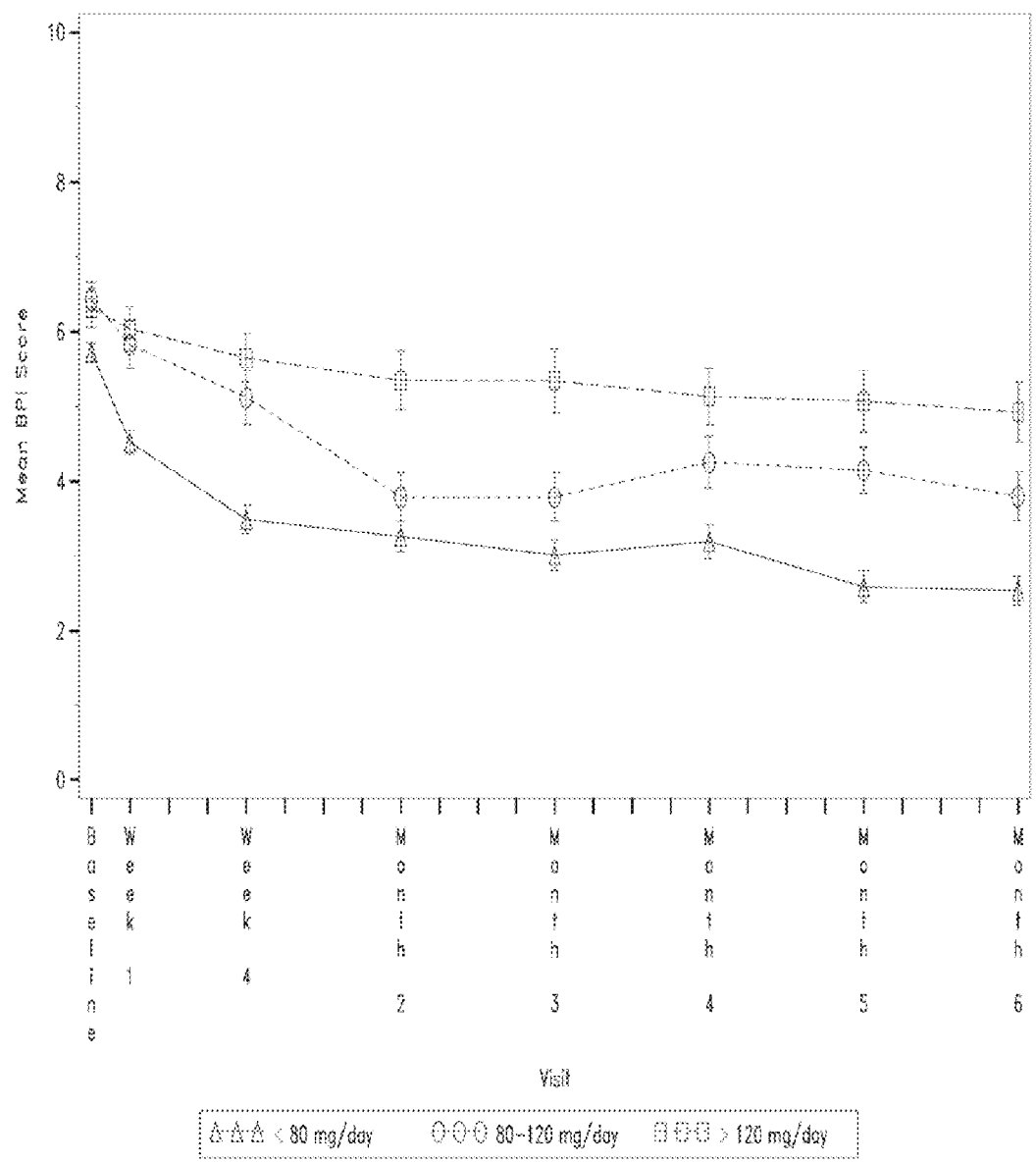

PHARMACEUTICAL COMPOSITION

RELATED APPLICATIONS

This application claims priority to U.S. Ser. No. 60/007,882 filed Dec. 17, 2007.

FIELD OF STUDY

This invention pertains to compositions and methods useful for treating pain in human patients. One such composition contains both an opioid antagonist and an opioid agonist formulated such that the agonist is released over time with minimal release of the antagonist.

BACKGROUND

Improved methods for treating pain are desired by those of skill in the art. A disease in which pain is a major symptom is osteoarthritis (OA). OA is the most common form of arthritis in the United States (Hochberg et al., 1995a), affecting more than 21 million people. It is a disease of primarily middle-aged and older adults and is a leading cause of disability (American College of Rheumatology, 2000a). OA results from degeneration of the joint cartilage, and usually involves the neck, low back, knees, hips, and fingers. The prevalence of OA of the hip and knee increases progressively with age (Peloso et al., 2000). Unlike rheumatoid arthritis and other inflammatory arthritides, inflammation, if present, is usually mild and localized to the joint. The cause of OA is unknown, but biomechanical stresses affecting the articular cartilage and subchondral bone, biochemical changes in the articular cartilage and synovial membrane, and genetic factors are significant in its pathogenesis (Hochberg et al., 1995b; American College of Rheumatology, 2000b).

OA is characterized by pain that typically worsens with activity and weight bearing and improves with rest, as well as morning stiffness, and pain and stiffness that ease after a few minutes of movement. Clinical examination often reveals tenderness to palpation, bony enlargement, crepitus, and/or limited joint motion (American College of Rheumatology, 2000b). As the disease advances, OA patients experience increasing pain and loss of function, with pain intruding at periods of rest (Peloso et al., 2000). Since no cure for OA is available, the primary goal of OA treatment is to reduce pain while maintaining or improving joint mobility and limiting functional impairment.

Nonpharmacologic and pharmacologic treatments for OA are used in conjunction to reduce pain and to improve functional status. Nonpharmacologic therapies include patient education, weight loss (if overweight), occupational therapy, physical therapy, and aerobic exercise programs to restore joint movement and increase strength and aerobic capacity (American College of Rheumatology, 2000a). The initial pharmacologic therapies for OA include nonopioid analgesics (e.g., acetaminophen) and topical analgesics, followed by treatment with nonsteroidal anti-inflammatory drugs (NSAIDs) and judicious use of intra-articular steroid injections (Hochberg et al., 1995a). Although these medications may provide temporary pain relief the beneficial effect may be offset by other factors. Use of nonopioid analgesics to treat moderate to severe OA pain is limited by a ceiling effect for analgesia (Roth et al., 2000). Additionally, NSAIDs can be toxic to the gastrointestinal tract, and NSAIDs and acetaminophen can produce renal toxicity, especially in the elderly (Peloso et al., 2000). Thus, a need exists for additional analgesic treatment options for pain associated with OA.

Recent efforts have been made to liberalize the use of opioids for the treatment of chronic nonmalignant pain (Sullivan et al., 2005). Sullivan proposes subject-centered principles to guide efforts to relieve chronic nonmalignant pain, including the acceptance of all subject pain reports as valid but negotiation of treatment goals early in care, avoidance of subject harm, and incorporation of chronic opioids as one part of the treatment plan if they improve the subject's overall health-related quality of life. Prescribing opiates in the treatment of chronic nonmalignant pain may pose a challenge to the primary care physician (Olsen et al., 2004).

Although an outright ban on opioid use in chronic nonmalignant pain is no longer ethically acceptable, ensuring that opioids provide overall benefit to subjects requires significant physician time and skill. Subjects with chronic nonmalignant pain should be assessed and treated for concurrent psychiatric disorders; those with disorders are entitled to equivalent efforts at pain relief. The essential question is not whether chronic nonmalignant pain is real or proportional to objective disease severity, but how it should be managed so that the subject's overall quality of life is optimized.

As early as the mid 1990s, naltrexone has been shown to effectively block morphine effects in humans (Kaiko et al., 1995). Morphine effects in normal volunteers were blocked by three 100-mg doses of naltrexone. The first dose of naltrexone was given 24 hours before dosing with controlled release morphine sulfate (MS Contin®), followed by a second dose at the time of MS Contin dosing and a third dose 24 hours after MS Contin administration. Single 200 mg doses of MS Contin given with the naltrexone blockade were generally well tolerated, and adverse effects were similar to those reported for naltrexone alone and for lower doses of morphine without naltrexone. Naltrexone proved safe and effective in blocking the effects of controlled release morphine, permitting bioequivalence studies of a high dose of morphine in normal volunteers.

Although well absorbed orally, naltrexone is subject to significant first-pass metabolism, with oral bioavailability estimates ranging from 5% to 40% (Naltrexone HCI Tablets, USP Package Insert). The activity of naltrexone is believed to be due to both the parent compound and the 6-β-naltrexol metabolite. Both parent drug and metabolites are excreted primarily by the kidney (53% to 79% of the dose); however, urinary excretion of unchanged naltrexone accounts for less than 2% of an oral dose and fecal excretion is a minor elimination pathway. The mean elimination terminal half-life ($t_{1/2}$) values for naltrexone and 6-β-naltrexol are 4 hours and 13 hours, respectively. Naltrexone and 6-β-naltrexol are dose-proportional in terms of area under the concentration-time curve (AUC) and maximum plasma concentration ($C_{max}$) over the range of 50 to 200 mg and do not accumulate after 100 mg daily doses.

Various formulations of opioids are in development that have a reduced risk of diversion and non-medical use and can be used to treat patients with chronic, nonmalignant conditions. Kadian® (morphine sulfate extended-release capsule) was developed for use in subjects with chronic pain who require repeated dosing with a potent opioid analgesic, and has been tested in subjects with pain due to malignant and nonmalignant conditions. Kadian contains polymer-coated extended-release pellets of morphine sulfate, to deliver up to 24 hours of continuous pain relief. This formulation lacks an immediate-release component, only providing a slow release of the analgesic. This slow-release technology serves to minimize plasma peaks and troughs, thereby providing a relatively flat pharmacokinetic (PK) curve upon multiple dosing. This delivery mechanism is ideally suited for chronic pain patients. Kadian capsules are an extended-release oral formulation of morphine sulfate indicated for the management of moderate to severe pain when a continuous, around-the-clock opioid analgesic is needed for an extended period of time.

However, persons abusing opioids are likely to tamper with controlled-release formulations in hopes of obtaining the entire dose to induce an immediate euphoria. To further deter non-medical opioid use, formulations containing opioid antagonists are being developed. As described herein, Kadian NT (morphine sulfate plus naltrexone hydrochloride extended-release capsules), is a product that is intended to be used as an opiate analgesic for moderate to severe pain. Its abuse-deterrence feature incorporates an immediate release of naltrexone upon illicit manipulation; this is intended to neutralize the euphoric potential of morphine and increase safety after ingestion of the tampered product. If Kadian NT is used as directed, a patient should receive a dose of morphine equivalent to the same mg dose of Kadian. However, if the drug product is tampered with and ingested by a patient who is opioid dependent, the patient may be exposed to a dose of naltrexone sufficient to produce withdrawal symptoms.

Abuse-resistant, sustained-release dosage forms of products intended to treat pain have been described in the art (see, for example, U.S. Application Nos. 2003/0124185 and 2003/0044458). However, it is believed that substantial amounts of the opioid antagonist or other antagonist found in these sequestered forms are released over time (usually less than 24 hours) due to the osmotic pressure that builds up in the core of the sequestered form, as water permeates through the sequestered form into the core. The high osmotic pressure inside the core of the sequestered form causes the opioid antagonist or antagonist to be pushed out of the sequestered form, thereby causing the opioid antagonist or antagonist to be released from the sequestered form. As shown below, certain embodiments described herein provide improved forms of sequestered opioid antagonists and controlled-release opioid agonists.

In view of the foregoing drawbacks of the sequestered forms of the prior art, there exists a need in the art for methods of treating pain a sequestered form of an opioid antagonist or other antagonist that is not substantially released from the sequestered form due to osmotic pressure. The invention provides such a sequestering form of an opioid antagonist or antagonist. This and other objects and advantages of the invention, as well as additional inventive features, will be apparent from the description of the invention provided herein.

BRIEF DESCRIPTION OF THE DRAWINGS

FIG. 2. Mean BPI Score Over Time by Treatment Group-Least Pain in Past 24 Hours.

FIG. 3. Mean BPI Score Over Time by Treatment Group-Average Pain in Past 24 Hours.

FIG. 4. Mean BPI Score Over Time by Treatment Group-Current Pain Level.

BRIEF SUMMARY

Figure 1:
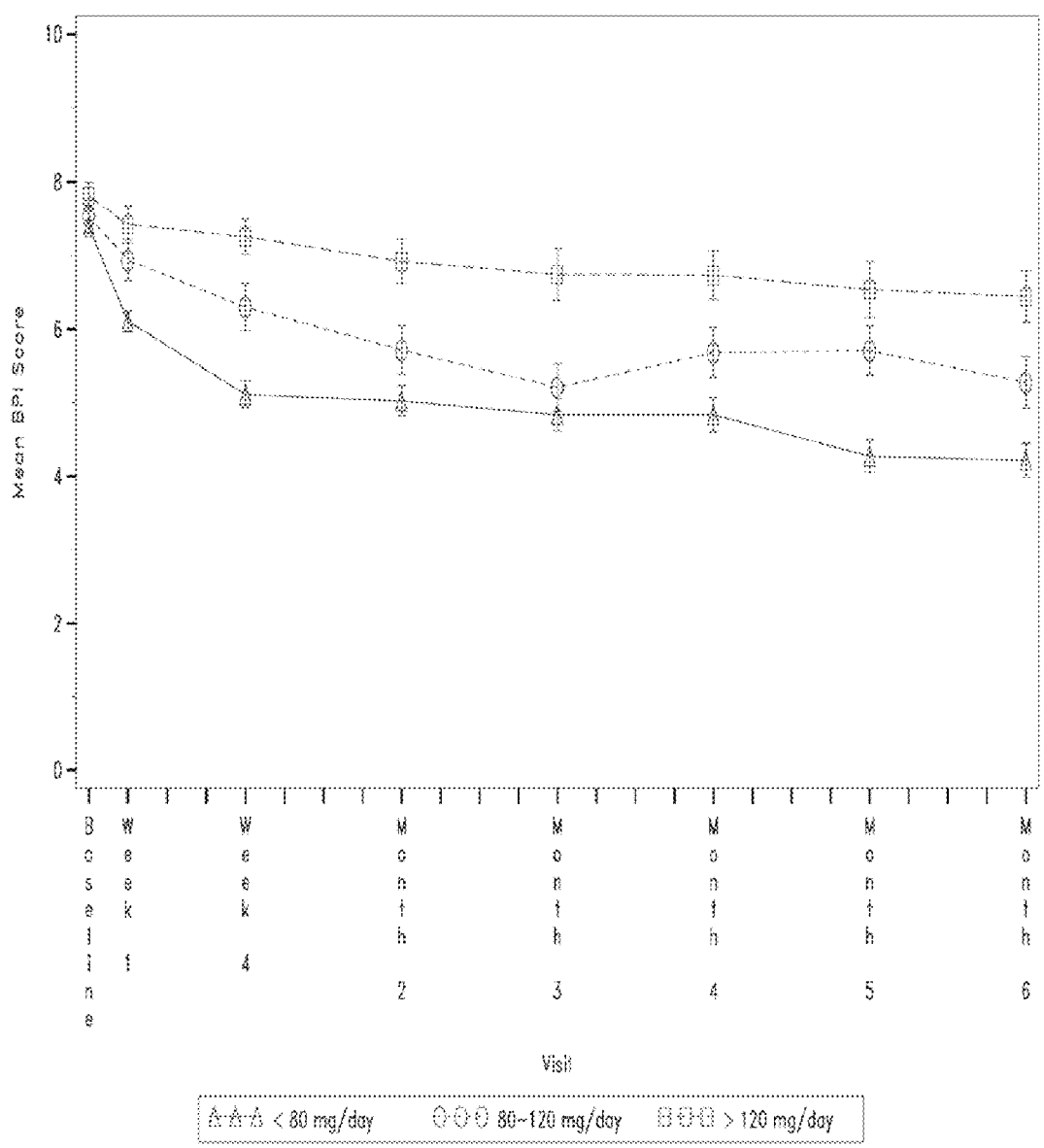
FIG. 1. Mean BPI Score Over Time by Treatment Group-Worst Pain in Past 24 Hours.

Provided herein is a pharmaceutical composition comprising an antagonist, an agonist, a seal coat, and a sequestering polymer, wherein the antagonist, agonist, seal coat and at least one sequestering polymer are all components of a single unit, and wherein the seal coat forms a layer physically separating the antagonist from the agonist from one another. The methods described herein provide methods for substantially relieving pain (e.g., providing an analgesic effect) for time periods of at least one week (e.g., two, four, eight, 12, 16, 20, 24, 28, 32, 36, 40 and 100 weeks) with regular administration (e.g., once, twice, three or four times daily). In certain embodiments, no substantial release of the antagonist from the intact form of the composition is observed. Methods for manufacturing Such a pharmaceutical composition are also provided. All references referred to or cited in this application are hereby incorporated by reference in their entirety.

DETAILED DESCRIPTION

Provided herein are compositions and methods for administering a multiple active agents to a mammal in a form and manner that minimizes the effects of either active agent upon the other in vivo. In certain embodiments, at least two active agents are formulated as part of a pharmaceutical composition. A first active agent may provide a therapeutic effect in vivo. The second active agent may be an antagonist of the first active agent, and may be useful in preventing misuse of the composition. For instance, where the first active agent is a narcotic, the second active agent may be an antagonist of the narcotic. The composition remains intact during normal usage by patients and the antagonist is not released. However, upon tampering with the composition, the antagonist may be released thereby preventing the narcotic from having its intended effect. In certain embodiments, the active agents are both contained within a single unit, such as a bead, in the form of layers. The active agents may be formulated with a substantially impermeable barrier as, for example, a controlled-release composition, such that release of the antagonist from the composition is minimized. In certain embodiments, the antagonist is released in in vitro assays but is substantially not released in vivo. In vitro and in vivo release of the active agent from the composition may be measured by any of several well-known techniques. For instance, in vivo release may be determined by measuring the plasma levels of the active agent or metabolites thereof (i.e., AUC, Cmax).

In certain embodiments, one of the active agents is an opioid receptor agonist. Several opioid agonists are commercially available or in clinical trials and may be administered as described herein such that the alcohol effects are minimized. Opioid agonists include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydroetorphine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, fentanyl, heroin, hydrocodone, hydromorphone, hydroxypethidine, isomethadone, ketobemidone, levallorphan, levorphanol, levophenacylmorphan, lofentanil, meperidine, meptaziniol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenazocine, phenomorphan, phenoperidine, piminodinie, piritramide, propheptazine, promedol, properidine, propiram, propoxyphene, sufentanil, tramadol, tilidine, derivatives or complexes thereof, pharmaceutically acceptable salts thereof, and combinations thereof. Preferably, the opioid agonist is selected from the group consisting of hydrocodone, hydromorphone, oxycodone, dihydrocodeine, codeine, dihydromorphine, morphine, buprenorphine, derivatives or complexes thereof, pharmaceutically acceptable salts thereof, and combinations thereof. Most preferably, the opioid agonist is morphine, hydromorphone, oxycodone or hydrocodone. Equianalgesic doses of these opioids, in comparison to a 15 mg dose of hydrocodone, are as follows: oxycodone (13.5 mg), codeine (90.0 mg), hydrocodone (15.0 mg), hydromorphone (3.375 mg), levorphanol (1.8 mg), meperidine (135.0 mg), methadone (9.0 mg), and morphine (27.0 mg).

A common dosage form of hydrocodone is in combination with acetaminophen and is commercially available, for example, as Lortab® in the United States from UCB Pharma, Inc. (Brussels, Belgium), as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen and a 7.5 mg hydrocodone bitartrate and 750 mg acetaminophen. Hydrocodone, in combination with aspirin, is given in an oral dosage form to adults generally in 1-2 tablets every 4-6 hours as needed to alleviate pain. The tablet form is 5 mg hydrocodone bitartrate and 224 mg aspirin with 32 mg caffeine; or 5 mg hydrocodone bitartrate and 500 mg aspirin. Another formulation comprises hydrocodone bitartrate and ibuprofen. Vicoprofen®, commercially available in the U.S. from Knoll Laboratories (Mount Olive, N.J.), is a tablet containing 7.5 mg hydrocodone bitartrate and 200 mg ibuprofen. The invention is contemplated to encompass all such formulations, with the inclusion of the opioid antagonist and/or antagonist in sequestered form as part of a subunit comprising an opioid agonist.

Oxycodone, chemically known as 4,5-epoxy-14-hydroxy-3-methoxy-17-methylmorpholine-6-one, is an opioid agonist whose principal therapeutic action is analgesia. Other therapeutic effects of oxycodone include anxiolysis, euphoria and feelings of relaxation. The precise mechanism of its analgesic action is not known, but specific CNS opioid receptors for endogenous compounds with opioid-like activity have been identified throughout the brain and spinal cord and play a role in the analgesic effects of this drug. Oxycodone is commercially available in the United States, e.g., as Oxycotin® from Purdue Pharma L.P. (Stamford, Conn.), as controlled-release tablets for oral administration containing 10 mg, 20 mg, 40 mg or 80 mg oxycodone hydrochloride, and as OxyIR™, also from Purdue Pharma L.P., as immediate-release capsules containing 5 mg oxycodone hydrochloride. The invention is contemplated to encompass all such formulations, with the inclusion of an opioid antagonist and/or antagonist in sequestered form as part of a subunit comprising an opioid agonist.

Oral hydromorphone is commercially available in the United States, e.g., as Dilaudid® from Abbott Laboratories (Chicago, Ill.). Oral morphine is commercially available in the United States, e.g., as Kadian® from Faulding Laboratories (Piscataway, N.J.).

In embodiments in which the opioid agonist comprises hydrocodone, the sustained-release oral dosage forms can include analgesic doses from about 8 mg to about 50 mg of hydrocodone per dosage unit. In sustained-release oral dosage forms where hydromorphone is the therapeutically active opioid, it is included in an amount from about 2 mg to about 64 mg hydromorphone hydrochloride. In another embodiment, the opioid agonist comprises morphine, and the sustained-release oral dosage forms of the invention include from about 2.5 mg to about 800 mg morphine, by weight. In yet another embodiment, the opioid agonist comprises oxycodone and the sustained-release oral dosage forms include from about 2.5 mg to about 800 mg oxycodone. In certain preferred embodiments, the sustained-release oral dosage forms include from about 20 mg to about 30 mg oxycodone. Controlled release oxycodone formulations are known in the art. The following documents describe various controlled-release oxycodone formulations suitable for use in the invention described herein, and processes for their manufacture: U.S. Pat. Nos. 5,266,331; 5,549,912; 5,508,042; and 5,656,295, which are incorporated herein by reference. The opioid agonist can comprise tramadol and the sustained-release oral dosage forms can include from about 25 mg to 800 mg tramadol per dosage unit.

In certain embodiments, another active agent contained within the composition may be an opioid receptor antagonist. In certain embodiments, the agonist and antagonist are administered together, either separately or as part of a single pharmaceutical unit. In the instance when the therapeutic agent is an opioid agonist, the antagonist preferably is an opioid antagonist, such as naltrexone, naloxone, nalmefene, cyclazacine, levallorphan, derivatives or complexes thereof, pharmaceutically acceptable salts thereof, and combinations thereof. More preferably, the opioid antagonist is naloxone or naltrexone. By "opioid antagonist" is meant to include one or more opioid antagonists, either alone or in combination, and is further meant to include partial antagonists, pharmaceutically acceptable salts thereof, stereoisomers thereof, ethers thereof, esters thereof, and combinations thereof. The pharmaceutically acceptable salts include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N-dibenzylethylenlediamine salt, and the like; inorganic acid salts, such as hydrochloride, hydrobromide, sulfate, phosphate, and the like; organic acid salts. Such as formate, acetate, trifluoroacetate, maleate, tartrate, and the like; sulfonates, such as methanesulfonate, benzenesulfonate, p-toluenesulfonate, and the like; amino acid salts, such as arginate, asparginate, glutamate, and the like. In certain embodiments, the amount of the opioid antagonist can be about 10 ng to about 275 mg. In a preferred embodiment, when the antagonist is naltrexone, it is preferable that the intact dosage form releases less than 0.125 mg or less within 24 hours, with 0.25 mg or greater of naltrexone released after 1 hour when the dosage form is crushed or chewed.

In a preferred embodiment, the opioid antagonist comprises naloxone. Naloxone is an opioid antagonist, which is almost void of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously in man prevent or promptly reverse the effects of morphine-like opioid agonist. One mg of naloxone intravenously has been reported to block completely the effect of 25 mg of heroin. The effects of naloxone are seen almost immediately after intravenous administration. The drug is absorbed after oral administration, but has been reported to be metabolized into an inactive form rapidly in its first passage through the liver, such that it has been reported to have significantly lower potency than when parenterally administered. Oral dosages of more than 1 g have been reported to be almost completely metabolized in less than 24 hours. It has been reported that 25% of naloxone administered sublingually is absorbed (Weinberg et al., *Clin. Pharmacol. Ther.* 44:335-340 (1988)).

In another preferred embodiment, the opioid antagonist comprises naltrexone. In the treatment of patients previously addicted to opioids, naltrexone has been used in large oral doses (over 100 mg) to prevent euphorigenic effects of opioid agonists. Naltrexone has been reported to exert strong preferential blocking action against mu over delta sites. Naltrexone is known as a synthetic congener of oxymorphone with no opioid agonist properties, and differs in structure from oxymorphone by the replacement of the methyl group located oil the nitrogen atom of oxymorphone with a cyclopropylmethyl group. The hydrochloride salt of naltrexone is soluble in water up to about 100 mg/cc. The pharmacological and pharmacokinetic properties of naltrexone have been evaluated in multiple animal and clinical studies. See, e.g., Gonzalez et al. *Drugs* 35:192-213 (1988). Following oral administration, naltrexone is rapidly absorbed (within 1 hour) and has an oral bioavailability ranging from 5-40%. Naltrexone's protein binding is approximately 21% and the volume of distribution following single-dose administration is 16.1 L/kg.

Naltrexone is commercially available in tablet form (Revia®, DuPont (Wilmington, Del.)) for the treatment of alcohol dependence and for the blockade of exogenously administered opioids. See, e.g., Revia (naltrexone hydrochloride tablets), Physician's Desk Reference, $51^{st}$ ed., Montvale, N.J.; and *Medical Economics* 51:957-959 (1997). A dosage of 50 mg Revia® blocks the pharmacological effects of 25 mg IV administered heroin for tip to 24 hours. It is known that, when coadministered with morphine, heroin or other opioids on a chronic basis, naltrexone blocks the development of physical dependence to opioids. It is believed that the method by which naltrexone blocks the effects of heroin is by competitively binding at the opioid receptors. Naltrexone has been used to treat narcotic addiction by complete blockade of the effects of opioids. It has been found that the most successful use of naltrexone for a narcotic addiction is with narcotic addicts having good prognosis, as part of a comprehensive occupational or rehabilitative program involving behavioral control or other compliance-enhancing methods. For treatment of narcotic dependence with naltrexone, it is desirable that the patient be opioid-free for at least 7-10 days. The initial dosage of naltrexone for such purposes has typically been about 25 mg, and if no withdrawal signs occur, the dosage may be increased to 50 mg per day. A daily dosage of 50 mg is considered to produce adequate clinical blockade of the actions of parenterally administered opioids. Naltrexone also has been used for the treatment of alcoholism as an adjunct with social and psychotherapeutic methods.

Other preferred opioid antagonists include, for example, cyclazocine and naltrexone, both of which have cyclopropylmethyl substitutions oil the nitrogen, retain much of their efficacy by the oral route, and last longer, with durations approaching 24 hours after oral administration.

The antagonist may also be a bittering agent. The term "bittering agent" as used herein refers to any agent that provides an unpleasant taste to the host upon inhalation and/or swallowing of a tampered dosage form comprising the sequestering subunit. With the inclusion of a bittering agent, the intake of the tampered dosage form produces a bitter taste upon inhalation or oral administration, which, in certain embodiments, spoils or hinders the pleasure of obtaining a high from the tampered dosage form, and preferably prevents the abuse of the dosage form.

Various bittering agents can be employed including, for example, and without limitation, natural, artificial and synthetic flavor oils and flavoring aromatics and/or oils, oleoresins and extracts derived from plants, leaves, flowers, fruits, and so forth, and combinations thereof. Nonlimiting representative flavor oils include spearmint oil, peppermint oil, eucalyptus oil, oil of nutmeg, allspice, mace, oil of bitter almonds, menthol and the like. Also useful bittering agents are artificial, natural and synthetic fruit flavors such as citrus oils, including lemon, orange, lime, and grapefruit, fruit essences, and so forth. Additional bittering agents include sucrose derivatives (e.g., sucrose octaacetate), chlorosucrose derivatives, quinine sulphate, and the like. A preferred bittering agent for use in the invention is Denatonium Benzoate NF-Anhydrous, sold under the name Bitrex™ (Macfarlan Smith Limited, Edinburgh, UK). A bittering agent can be added to the formulation in an amount of less than about 50% by weight, preferably less than about 10% by weight, more preferably less than about 5% by weight of the dosage form, and most preferably in an amount ranging from about 0.1 to 1.0 percent by weight of the dosage form, depending on the particular bittering agent(s) used.

Alternatively, the antagonist may be a dye. The term "dye" as used herein refers to any agent that causes discoloration of the tissue in contact. In this regard, if the sequestering subunit is tampered with and the contents are snorted, the dye will discolor the nasal tissues and surrounding tissues thereof. Preferred dyes are those that can bind strongly with subcutaneous tissue proteins and are well-known in the art. Dyes useful in applications ranging from, for example, food coloring to tattooing, are exemplary dyes suitable for the invention. Food coloring dyes include, but are not limited to FD&C Green #3 and FD&C Blue #1, as well as any other FD&C or D&C color. Such food dyes are commercially available through companies, such as Voigt Global Distribution (Kansas City, Mo.).

The antagonist may alternatively be an irritant. The term "irritant" as used herein includes a compound used to impart an irritating, e.g., burning or uncomfortable, sensation to an abuser administering a tampered dosage form of the invention. Use of an irritant will discourage an abuser from tampering with the dosage form and thereafter inhaling, injecting, or swallowing the tampered dosage form. Preferably, the irritant is released when the dosage form is tampered with and provides a burning or irritating effect to the abuser upon inhalation, injection, and/or swallowing the tampered dosage form. Various irritants can be employed including, for example, and without limitation, capsaicin, a capsaicin analog with similar type properties as capsaicin, and the like. Some capsaicin analogues or derivatives include, for example, and without limitation, resiniferatoxin, titnyatoxin, heptanoylisobutylamide, heptanoyl guaiacylamide, other isobutylamides or guaiacylamides, dihydrocapsaicin, homovanillyl octylester, nonanoyl vanillylamide, or other compounds of the class known as vanilloids. Resiniferatoxin is described, for example, in U.S. Pat. No. 5,290,816. U.S. Pat. No. 4,812,446 describes capsaicin analogs and methods for their preparation. Furthermore, U.S. Pat. No. 4,424,205 cites Newman, "Natural and Synthetic Pepper-Flavored Substances," published in 1954 as listing pungency of capsaicin-like analogs. Ton et al., *British Journal of Pharmacology* 10:175-182 (1955), discusses pharmacological actions of capsaicin and its analogs. With the inclusion of an irritant (e.g., capsaicin) in the dosage form, the irritant imparts a burning or discomforting quality to the abuser to discourage the inhalation, injection, or oral administration of the tampered dosage form, and preferably to prevent the abuse of the dosage form. Suitable capsaicin compositions include capsaicin (trans 8-methyl-N-vanillyl-6-noneamide) or analogues thereof in a concentration between about 0.00125% and 50% by weight, preferably between about 1% and about 7.5% by weight, and most preferably, between about 1% and about 5% by weight.

The antagonist may also be a gelling agent. The term "gelling agent" as used herein refers to any agent that provides a gel-like quality to the tampered dosage form, which slows the absorption of the therapeutic agent, which is formulated with the sequestering subunit, such that a host is less likely to obtain a rapid "high." In certain preferred embodiments, when the dosage form is tampered with and exposed to a small amount (e.g., less than about 10 ml) of an aqueous liquid (e.g., water), the dosage form will be unsuitable for injection and/or inhalation. Upon the addition of the aqueous liquid, the tampered dosage form preferably becomes thick and viscous, rendering it unsuitable for injection. The term "unsuitable for injection" is defined for purposes of the invention to mean that one would have substantial difficulty injecting the dosage form (e.g., due to pain upon administration or difficulty pushing the dosage form through a syringe) due to the viscosity imparted on the dosage form, thereby reducing the potential for abuse of the therapeutic agent in the dosage form. In certain embodiments, the gelling agent is present in such an amount in the dosage form that attempts at evaporation (by the application of heat) to an aqueous mixture of the dosage form in an effort, to produce a higher concentration of the therapeutic agent, produces a highly viscous substance unsuitable for injection. When nasally inhaling the tampered dosage form, the gelling agent can become gel-like upon administration to the nasal passages, due to the moisture of the mucous membranes. This also makes such formulations aversive to nasal administration, as the gel will stick to the nasal passage and minimize absorption of the abusable substance. Various gelling agents may can be employed including, for example, and without limitation, sugars or sugar-derived alcohols, such as mannitol, sorbitol, and the like, starch and starch derivatives, cellulose derivatives, such as microcrystalline cellulose, sodium caboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacant, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof, etc. In certain preferred embodiments, the gelling agent is xanthan gum. In other preferred embodiments, the gelling agent of the invention is pectin The pectin or pectic substances useful for this invention include not only purified or isolated pectates but also crude natural pectin sources, such as apple, citrus or sugar beet residues, which have been subjected, when necessary, to esterification or de-esterification, e.g., by alkali or enzymes. Preferably, the pectins used in this invention are derived from citrus fruits, such as lime, lemon, grapefruit, and orange. With the inclusion of a gelling agent in the dosage form, the gelling agent preferably imparts a gel-like quality to the dosage form upon tampering that spoils or hinders the pleasure of obtaining a rapid high from due to the gel-like consistency of the tampered dosage form in contact with the mucous membrane, and in certain embodiments, prevents the abuse of the dosage form by minimizing absorption, e.g., in the nasal passages. A gelling agent can be added to the formulation in a ratio of gelling agent to opioid agonist of from about 1:40 to about 40:1 by weight, preferably from about 1:1 to about 30:1 by weight, and more preferably from about 2:1 to about 10:1 by weight of the opioid agonist. In certain other embodiments, die dosage form forms a viscous gel having a viscosity of at least about 10 cP after the dosage form is tampered with by dissolution in an aqueous liquid (from about 0.5 to about 10 ml and preferably from 1 to about 5 ml). Most preferably, the resulting mixture will have a viscosity of at least about 60 cP.

The antagonist can comprise a single type of antagonist (e.g., a capsaicin), multiple forms of a single type of antagonist (e.g., a capasin and an analogue thereof), or a combination of different types of antagonists (e.g., one or more bittering agents and one or more gelling agents). Desirably, the amount of antagonist in a unit of the invention is not toxic to the host.

In one embodiment, the invention provides a sequestering subunit comprising an opioid antagonist and a blocking agent, wherein the blocking agent substantially prevents release of the opioid antagonist from the sequestering subunit in the gastrointestinal tract for a time period that is greater than 24 hours. This sequestering subunit is incorporated into a single pharmaceutical unit that also includes an opioid agonist. The pharmaceutical unit thus includes a core portion to which the opioid antagonist is applied. A seal coat is then optionally applied upon the antagonist. Upon the seal coat is then applied a composition comprising the pharmaceutically active agent. An additional layer containing the same or a different blocking agent may then be applied such that the opioid agonist is released in the digestive tract over time (i.e., controlled release). Thus, the opioid antagonist and the opioid agonist are both contained within a single pharmaceutical unit, which is typically in the form of a bead.

The term "sequestering subunit" as used herein refers to any means for containing an antagonist and preventing or substantially preventing the release thereof in the gastrointestinal tract when intact, i.e., when not tampered with. The term "blocking agent" as used herein refers to the means by which the sequestering subunit is able to prevent substantially the antagonist from being released. The blocking agent may be a sequestering polymer, for instance, as described in greater detail below.

The terms "substantially prevents," "prevents," or any words stemming therefrom, as used herein, means that the antagonist is substantially not released from the sequestering subunit in the gastrointestinal tract. By "substantially not released" is meant that the antagonist may be released in a small amount, but the amount released does not affect or does not significantly affect the analgesic efficacy when the dosage form is orally administered to a host, e.g., a mammal (e.g., a human), as intended. The terms "substantially prevents," "prevents," or any words stemming therefrom, as used herein, does not necessarily imply a complete or 100% prevention. Rather, there are varying decrees of prevention of which one of ordinary skill in the art recognizes as having a potential benefit. In this regard, the blocking agent substantially prevents or prevents the release of the antagonist to the extent that at least about 80% of the antagonist is prevented from being released from the sequestering subunit in the gastrointestinal tract for a time period that is greater than 24 hours. Preferably, the blocking agent prevents release of at least about 90% of the antagonist from the sequestering subunit in the gastrointestinal tract for a time period that is greater than 24 hours. More preferably, the blocking agent prevents release of at least about 95% of the antagonist from the sequestering subunit. Most preferably, the blocking agent prevents release of at least about 99% of the antagonist from the sequestering subunit in the gastrointestinal tract for a time period that is greater than 24 hours.

For purposes of this invention, the amount of the antagonist released after oral administration can be measured in-vitro by dissolution testing as described in the United States Pharmacopoeia (USP26) in chapter <711> Dissolution. For example, using 900 mL of 0.1 N HCl, Apparatus 2 (Paddle), 75 rpm, at 37° C. to measure release at various times from the dosage unit. Other methods of measuring the release of an antagonist from a sequestering subunit over a given period of time are known in the art (see, e.g., USP26).

Without being bound to any particular theory, it is believed that the sequestering subunit of the invention overcomes the limitations of the sequestered forms of an antagonist known in the art in that the sequestering subunit of the invention reduces osmotically-driven release of the antagonist from the sequestering subunit. Furthermore, it is believed that the present inventive sequestering subunit reduces the release of the antagonist for a longer period of time (e.g., greater than 24 hours) in comparison to the sequestered forms of antagonists known in the art. The fact that the sequestered subunit of the invention provides a longer prevention of release of the antagonist is particularly relevant, since precipitated withdrawal could occur after the time for which the therapeutic agent is released and acts. It is well known that the gastrointestinal tract transit time for individuals varies greatly within the population. Hence, the residue of the dosage form may be retained in the tract for longer than 24 hours, and in some cases for longer than 48 hours. It is further well known that opioid analgesics cause decreased bowel motility, further prolonging gastrointestinal tract transit time. Currently, sustained-release forms having an effect over a 24 hour time period have been approved by the Food and Drug Administration. In this regard, the present inventive sequestering subunit provides prevention of release of the antagonist for a time period that is greater than 24 hours when the sequestering subunit has not been tampered.

The sequestering subunit of the invention is designed to prevent substantially the release of the antagonist when intact. By "intact" is meant that a dosage form has not undergone tampering. The term "tampering" is meant to include any manipulation by mechanical, thermal and/or chemical means, which changes the physical properties of the dosage form. The tampering can be, for example, crushing, shearing, grinding, chewing, dissolution in a solvent, heating (for example, greater than about 45° C.), or any combination thereof. When the sequestering subunit of the invention has been tampered with, the antagonist is immediately released from the sequestering subunit.

By "subunit" is meant to include a composition, mixture, particle; etc., that can provide a dosage form (e.g., an oral dosage form) when combined with another subunit. The subunit can be in the form of a bead, pellet, granule, spheroid, or the like, and can be combined with additional same or different subunits, in the form of a capsule, tablet or the like, to provide a dosage form, e.g., an oral dosage form. The subunit may also be part of a larger, single unit, forming part of that unit, such as a layer. For instance, the subunit may be a core coated with an antagonist and a seal coat; this subunit may then be coated with additional compositions including a pharmaceutically active agent such as an opioid agonist.

For purposes of the invention, the antagonist can be any agent that negates the effect of the therapeutic agent or produces an unpleasant or punishing stimulus or effect, which will deter or cause avoidance of tampering with the sequestering subunit or compositions comprising the same. Desirably, the antagonist does not harm a host by its administration or consumption but has properties that deter its administration or consumption, e.g., by chewing and swallowing or by crushing and snorting, for example. The antagonist can have a strong or foul taste or smell, provide a burning or tingling sensation, cause a lachrymation response, nausea, vomiting, or any other unpleasant or repugnant sensation, or color tissue, for example. Preferably, the antagonist is selected from the group consisting of an antagonist of a therapeutic agent, a bittering agent, a dye, a gelling agent, and an irritant. Exemplary antagonists include capsaicin, dye, bittering agents and emetics.

By "antagonist of a therapeutic agent" is meant any drug or molecule, naturally-occurring or synthetic, that binds to the same target molecule (e.g., a receptor) of the therapeutic agent, yet does not produce a therapeutic, intracellular, or in vivo response. In this regard, the antagonist of a therapeutic agent binds to the receptor of the therapeutic agent, thereby preventing the therapeutic agent from acting on the receptor, thereby preventing the achievement of a "high" in the host.

In the instance when the therapeutic agent is an opioid agonist, the antagonist preferably is an opioid antagonist, such as naltrexone, naloxone, nalmefene, cyclazacine, levallorphan, derivatives or complexes thereof, pharmaceutically acceptable salts thereof, and combinations thereof More preferably, the opioid antagonist is naloxone or naltrexone. By "opioid antagonist" is meant to include one or more opioid antagonists, either alone or in combination, and is further meant to include partial antagonists, pharmaceutically acceptable salts thereof, stereoisomers thereof, ethers thereof, esters thereof, and combinations thereof. The pharmaceutically acceptable salts include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N-dibenzylethylenlediamine salt, and the like; inorganic acid salts, such as hydrochloride, hydrobromide, sulfate, phosphate, and the like; organic acid salts, such as formate, acetate, trifluoroacetate, maleate, tartrate, and the like; sulfonates, such as methanesulfonate, benzenesulfonate, p-toluenesulfonate, and the like; amino acid salts, such as arginate, asparginate, glutamate, and the like. In certain embodiments, the amount of the opioid antagonist, present in sequestered form, can be about 10 ng to about 275 mg. In a preferred embodiment, when the antagonist is naltrexone, it is preferable that the intact dosage form releases less than 0.125 mg or less within 24 hours, with 0.25 mg or greater of naltrexone released after 1 hour when the dosage form is crushed or chewed.

The antagonist can comprise a single type of antagonist (e.g., a capsaicin), multiple forms of a single type of antagonist (e.g., a capsin and an analogue thereof), or a combination of different types of antagonists (e.g., one or more bittering agents and one or more gelling agents). Desirably, the amount of antagonist in the sequestering subunit of the invention is not toxic to the host.

The blocking agent prevents or substantially prevents the release of the antagonist in the gastrointestinal tract for a time period that is greater than 24 hours, e.g., between 24 and 25 hours, 30 hours, 35 hours, 40 hours, 45 hours, 48 hours, 50 hours, 55 hours, 60 hours, 65 hours, 70 hours, 72 hours, 75 hours, 80 hours, 85 hours, 90 hours, 95 hours, or 100 hours; etc. Preferably, the time period for which the release of the antagonist is prevented or substantially prevented in the gastrointestinal tract is at least about 48 hours. More preferably, the blocking agent prevents or substantially prevents the release for a time period of at least about 72 hours.

The blocking agent of the present inventive sequestering subunit can be a system comprising a first antagonist-impermeable material and a core. By "antagonist-impermeable material" is meant any material that is substantially impermeable to the antagonist, such that the antagonist is substantially not released from the sequestering subunit. The term "substantially impermeable" as used herein does not necessarily imply complete or 100% impermeability. Rather, there are varying degrees of impermeability of which one of ordinary skill in the art recognizes as having a potential benefit. In this regard, the antagonist-impermeable material substantially prevents or prevents the release of the antagonist to an extent that at least about 80% of the antagonist is prevented from being released from the sequestering subunit in the gastrointestinal tract for a time period that is greater than 24 hours. Preferably, the antagonist-impermeable material prevents release of at least about 90% of the antagonist from the sequestering subunit in the gastrointestinal tract for a time period that is greater than 24 hours. More preferably, the antagonist-impermeable material prevents release of at least about 95% of the antagonist from the sequestering subunit. Most preferably, the antagonist-impermeable material prevents release of at least about 99% of the antagonist from the sequestering subunit in the gastrointestinal tract for a time period that is greater than 24 hours. The antagonist-impermeable material prevents or substantially prevents the release of the antagonist in the gastrointestinal tract for a time period that is greater than 24 hours, and desirably, at least about 48 hours. More desirably, the antagonist-impermeable material prevents or substantially prevents the release of the adverse agent from the sequestering subunit for a time period of at least about 72 hours.

Preferably, the first antagonist-impermeable material comprises a hydrophobic material, such that the antagonist is not released or substantially not released during its transit through the gastrointestinal tract when administered orally as intended, without having been tampered with. Suitable hydrophobic materials for use in the invention are described herein and set forth below. The hydrophobic material is preferably a pharmaceutically acceptable hydrophobic material. Preferably, the pharmaceutically acceptable hydrophobic material comprises a cellulose polymer.

It is preferred that the first antagonist-impermeable material comprises a polymer insoluble in the gastrointestinal tract. One of ordinary skill in the art appreciates that a polymer that is insoluble in the gastrointestinal tract will prevent the release of the antagonist upon ingestion of the sequestering subunit. The polymer can be a cellulose or an acrylic polymer. Desirably, the cellulose is selected from the group consisting of ethylcellulose, cellulose acetate, cellulose propionate, cellulose acetate propionate, cellulose acetate butyrate, cellulose acetate phthalate, cellulose triacetate, and combinations thereof Ethylcellulose includes, for example, one that has an ethoxy content of about 44 to about 55%. Ethylcellulose can be used in the form of an aqueous dispersion, an alcoholic solution, or a solution in other suitable solvents. The cellulose can have a degree of substitution (D.S.) on the anhydroglucose unit, from greater than zero and up to 3 inclusive. By "degree of substitution" is meant the average number of hydroxyl groups on the anhydroglucose unit of the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, monocellulose alkanylate, dicellulose alkanylate, tricellulose alkanylate, monocellulose alkenylates, dicellulose alkenylates, tricellulose alkenylates, monocellulose aroylates, dicellulose aroylates, and tricellulose aroylates.

More specific celluloses include cellulose propionate having a D.S. of 1.8 and a propyl content of 39.2 to 45 and a hydroxy content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyiyl content of 17 to 53% and a hydroxy content of 0.5 to 4.7%; cellulose triacylate having a D.S. of 2.9 to 3, such as cellulose triacetate, cellulose trivalerate, cellulose trilaurate, cellulose tripatmitate, cellulose trisuccinate, and cellulose trioctanoate; cellulose diacylates having a D.S. of 2.2 to 2.6, such as cellulose disuccinate, cellulose dipalmitate, cellulose dioctanoate, cellulose dipentanoate, and coesters of cellulose, such as cellulose acetate butyrate, cellulose acetate octanoate butyrate, and cellulose acetate propionate.

Additional cellulose polymers useful for preparing a sequestering subunit of the invention includes acetaldehyde dimethyl cellulose acetate, cellulose acetate ethylcarbamate, cellulose acetate methycarbamate, and cellulose acetate dimethylaminocellulose acetate.

The acrylic polymer preferably is selected from the group consisting of methacrylic polymers, acrylic acid and methacrylic acid copolymers, methyl methacrylate copolymers, ethoxyethyl methacrylates, cyanoethyl methacrylate, poly (acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly (methacrylic acid anhydride), glycidyl methacrylate copolymers, and combinations thereof. An acrylic polymer useful for preparation of a sequestering subunit of the invention includes acrylic resins-comprising copolymers synthesized from acrylic and methacrylic acid esters (e.g., the copolymer of acrylic acid lower alkyl ester and methacrylic acid lower alkyl ester) containing about 0.02 to about 0.03 mole of a tri (lower alkyl)ammonium group per mole of the acrylic and methacrylic monomer used. An example of a suitable acrylic resin is ammonio methacrylate copolymer NF21, a polymer manufactured by Rohm Pharma GmbH, Darmstadt, Germany, and sold under the Eudragit® trademark. Eudragit RS30D is preferred. Eudragit® is a water-insoluble copolymer of ethyl acrylate (EA), methyl methacrylate (MM) and trimethylammoniumethyl methacrylate chloride (TAM) in which the molar ratio of TAM to the remaining components (EA and MM) is 1:40. Acrylic resins, such as Eudragit®, can be used in the form of an aqueous dispersion or as a solution in suitable solvents.

In another preferred embodiment, the antagonist-impermeable material is selected from the group consisting of polylactic acid, polyglycolic acid, a co-polymer of polylactic acid and polyglycolic acid, and combinations thereof. In certain other embodiments, the hydrophobic material includes a biodegradable polymer comprising a poly(lactic/glycolic acid) ("PLGA"), a polylactide, a polyglycolide, a polyanhydride, a polyorthoester, polycaprolactones, polyphosphazenes, polysaccharides, proteinaceous polymers, polyesters, polydioxanone, polygluconate, polylactic-acid-polyethylene oxide copolymers, poly(hydroxybutyrate), polyphosphoester or combinations thereof.

Preferably, the biodegradable polymer comprises a poly (lactic/glycolic acid), a copolymer of lactic and glycolic acid, having a molecular weight of about 2,000 to about 500,000 daltons. The ratio of lactic acid to glycolic acid is preferably from about 100:1 to about 25:75, with the ratio of lactic acid to glycolic acid of about 65:35 being more preferred.

Poly(lactic/glycolic acid) can be prepared by the procedures set forth in U.S. Pat. No. 4,293,539 (Ludwig et al.), which is incorporated herein by reference. In brief, Ludwig prepares the copolymer by condensation of lactic acid and glycolic acid in the presence of a readily removable polymerization catalyst (e.g., a strong ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction can be conducted without solvents at a temperature from about 100° C. to about 250° C. for about 48 to about 96 hours, preferably under a reduced pressure to facilitate removal of water and by-products. Poly(lactic/glycolic acid) is then recovered by filtering the molten reaction mixture in an organic solvent, such as dichloromethane or acetone, and then filtering, to remove the catalyst.

Suitable plasticizers, for example, acetyl triethyl citrate, acetyl tributyl citrate, triethyl citrate, diethyl phthalate, dibutyl phthalate, or dibutyl sebacate, also can be admixed with the polymer used to make the sequestering subunit. Additives, Such as coloring agents, talc and/or magnesium stearate, and other additives also can be used in making the present inventive sequestering subunit.

In certain embodiments, additives may be included in the compositions to improve the sequestering characteristics of the sequestering subunit. As described below, the ratio of additives or components with respect to other additives or components may be modified to enhance or delay improve sequestration of the agent contained within the subunit. Various amounts of a functional additive (i.e., a charge-neutralizing additive) may be included to vary the release of an antagonist, particularly where a water-soluble core (i.e., a sugar sphere) is utilized. For instance, it has been determined that the inclusion of a low amount of charge-neutralizing additive relative to sequestering polymer on a weight-by-weight basis may cause decreased release of the antagonist.

In certain embodiments, a surfactant may serve as a charge-neutralizing additive. Such neutralization may in certain embodiments reduce the swelling of the sequestering polymer by hydration of positively charged groups contained therein. Surfactants (ionic or non-ionic) may also be used in preparing the sequestering subunit. It is preferred that the surfactant be ionic. Suitable exemplary agents include, for example, alkylaryl sulphonates, alcohol sulphates, sulphosuccinates, sulphosuccinamates, sarcosinates or taurates and others. Additional examples include but are not limited to ethoxylated castor oil, benzalkonium chloride, polyglycolyzed glycerides, acetylated monoglycerides, sorbitan fatty acid esters, poloxamers, polyoxyethylene fatty acid esters, polyoxyethylene derivatives, monoglycerides or ethoxylated derivatives thereof, diglycerides or polyoxyethylene derivatives thereof, sodium docusate, sodium lauryl sulfate, dioctyl sodium sulphosuccinate, sodium lauryl sarcosinate and sodium methyl cocoyl taurate, magnesium lauryl sulfate, triethanolamine, cetrimide, sucrose laurate and other sucrose esters, glucose (dextrose) esters, simethicone, ocoxynol, dioctyl sodiumsulfosuceinate, polyglycolyzed glycerides, sodiumdodecylbenzene sulfonate, dialkyl sodiumsulfosuccinate, fatty alcohols such as lauryl, cetyl, and steryl, glycerylesters, cholic acid or derivatives thereof, lecithins, and phospholipids. These agents are typically characterized as ionic (i.e., anionic or cationic) or nonionic. In certain embodiments described herein, an anionic surfactant such as sodium lauryl sulfate (SLS) is preferably used (U.S. Pat. No. 5,725,883; U.S. Pat. No. 7,201,920; EP 502642A1; Shokri, et al. Pharm. Sci. 2003. *The effect of sodium lauryl sulphate oil the release of diazepam from solid dispersions prepared by cogrinding technique*. Wells, et al. *Effect of Anionic Surfactants on the Release of Chlorpheniramine Maleate From an Inert, Heterogeneous Matrix*. Drug Development and Industrial Pharmacy 18(2) (1992). 175-186. Rao, et al. "Effect of Sodium Lauryl Sulfate on the Release of Rifampicin from Guar Gum Matrix." Indian Journal of Pharmaceutical Science (2000): 404-406; Knop, et al. *Influence of surfactants of different charge and concentration on drug release from pellets coated with an aqueous dispersion of quaternary acrylic polymers*. STP Pharma Sciences, Vol. 7, No. 6, (1997) 507-512). Other suitable agents are known in the art.

As shown herein, SLS is particularly useful in combination with Eudragit RS when the sequestering subunit is built upon a sugar sphere substrate. The inclusion of SLS at less than approximately 6.3% on a weight-to-weight basis relative to the sequestering polymer (i.e., Eudragit RS) may provide a charge neutralizing function (theoretically 20% and 41% neutralization, respectfully), and thereby significantly slow the release of the active agent encapsulated thereby (i.e., the antagonist naltrexone). Inclusion of more than approximately 6.3% SLS relative to the sequestering polymer appears to increase release of the antagonist from the sequestering subunit. With respect to SLS used in conjunction with Eudragit® RS, it is preferred that the SLS is present at approximately 1%, 2%, 3%, 4% or 5%, and typically less than 6% on a w/w basis relative to the sequestering polymer (i.e., Eudragit® RS). In preferred embodiments, SLS may be present at approximately 1.6% or approximately 3.3% relative to the sequestering polymer. As discussed above, many agents (i.e., surfactants) may substitute for SLS in the compositions disclosed herein.

Additionally useful agents include those that may physically block migration of the antagonist from the subunit and/or enhance the hydrophobicity of the barrier. One exemplary agent is talc, which is commonly used in pharmaceutical compositions (Pawar et al. *Agglomeration of Ibuprofen With Talc by Novel Crystallo-Co-Agglomeration Technique*. AAPS PharmSciTech. 2004; 5(4): article 55). As shown in the Examples, talc is especially useful where the sequestering subunit is built upon a sugar sphere core. Any form of talc may be used, so long as it does not detrimentally affect the function of the composition. Most talc results from the alteration of dolomite ($CaMg(CO_3)_2$ or magnesite (MgO) in the presence of excess dissolved silica ($SiO_2$) or by altering serpentine or quartzite. Talc may be include minerals such as tremolite ($CaMg_3(SiO_3)_4$), serpentine ($3MgO.2SiO_2.2H_2O$), anthophyllite ($Mg_7.(OH)_2.(Si_4O_{11})_2$), magnesite, mica, chlorite, dolomite, the calcite form of calcium carbonate ($CaCO_3$), iron oxide, carbon, quartz, and/or manganese oxide. The presence of such impurities may be acceptable in the compositions described herein provided the function of the talc is maintained. It is preferred that that talc be USP grade. As mentioned above, the function of talc as described herein is to enhance the hydrophobicity and therefore the functionality of the sequestering polymer. Many substitutes for talc may be utilized in the compositions described herein as may be determined by one of skill in the art.

It has been determined that the ratio of talc to sequestering polymer may make a dramatic difference in the functionality of the compositions described herein. For instance, the Examples described below demonstrate that the talc to sequestering polymer ratio (w/w) is important with respect to compositions designed to prevent the release of naltrexone therefrom. It is shown therein that inclusion of an approximately equivalent amount (on a weight-by-weight basis) of talc and Eudragit® RS results in a very low naltrexone release profile. In contrast, significantly lower or higher both a lower (69% w/w) and a higher (151% w/w) talc:Eudragit® RS ratios result in increased release of naltrexone release. Thus, where talc and Eudragit® RS are utilized, it is preferred that talc is present at approximately 75%, 80%, 85%, 90%, 95%, 100%, 105%, 110%, 115%, 120% or 125% w/w relative to Eudragit® RS. As described above, the most beneficial ratio for other additives or components will vary and may be determined using standard experimental procedures.

In certain embodiments, such as where a water-soluble core is utilized, it is useful to include agents that may affect the osmotic pressure of the composition (i.e., an osmotic pressure regulating agent) (see, in general, WO 2005/046561 A2 and WO 2005/046649 A2 relating to Eudramode®). This agent is preferably applied to the Eudragit® RS/talc layer described above. In a pharmaceutical unit comprising a sequestering subunit overlayed by an active agent (i.e., a controlled-release agonist preparation), the osmotic pressure regulating agent is preferably positioned immediately beneath the active agent layer. Suitable osmotic pressure regulating agents may include, for instance, hydroxypropylmethyl cellulose (HPMC) or chloride ions (i.e., from NaCl), or a combination of HPMC and chloride ions (i.e., from NaCl). Other ions that may be useful include bromide or iodide. The combination of sodium chloride and HPMC may be prepared in water or in a mixture of ethanol and water, for instance. HPMC is commonly utilized in pharmaceutical compositions (see, for example, U.S. Pat. Nos. 7,226,620 and 7,229,982). In certain embodiments, HPMC may have a molecular weight ranging from about 10,000 to about 1,500,000, and typically from about 5000 to about 10,000 (low molecular weight HPMC). The specific gravity of HPMC is typically from about 1.19 to about 1.31, with an average specific gravity of about 1.26 and a viscosity of about 3600 to 5600. HPMC may be a water-soluble synthetic polymer. Examples of suitable, commercially available hydroxypropyl methylcellulose polymers include Methocel K100 LV and Methocel K4M (Dow). Other HPMC additives are known in the art and may be suitable in preparing the compositions described herein. As shown in the Examples, the inclusion of NaCl (with HPMC) was found to have positively affect sequestration of naltrexone by Eudragit® RS. In certain embodiments, it is preferred that the charge-neutralizing additive (i.e., NaCl) is included at less than approximately 1, 2, 3, 4, 5, 6, 7, 8, 9, or 10% of the composition on a weight-by-weight basis. In other preferred embodiments, the charge-neutralizing additive is present at approximately 4% of the composition on a weight-by-weight basis.

Thus, in one embodiment, a sequestering subunit built upon a sugar sphere substrate is provide d comprising a sequestering polymer (i.e., Eudragit® RS) in combination with several optimizing agents, including sodium lauryl sulfate (SLS) as a charge-neutralizing agent to reduce swelling of the film by hydration of the positively charged groups on the polymer; talc to create a solid impermeable obstacle to naltrexone transport through the film and as a hydrophobicity-enhancing agent; and a chloride ion (i.e., as NaCl) as an osmotic pressure reducing agent. The ratio of each of the additional ingredients relative to the sequestering polymer was surprisingly found to be important to the function of the sequestering subunit. For instance, the Examples provide a sequestering subunit including a sequestering polymer and the optimizing agents SLS at less than 6%, preferably 1-4%, and even more preferably 1.6% or 3.3% on a w/w basis relative to Eudragit RS; talc in an amount approximately equal to Eudragit® RS (on a w/w basis); and, NaCl present at approximately 4% on a w/w basis relative to Eudragit® RS.

The therapeutic agent applied upon the sequestering subunit may be any medicament. The therapeutic agent of the present inventive compositions can be any medicinal agent used for the treatment of a condition or disease, a pharmaceutically acceptable salt thereof, or an analogue of either of the foregoing. The therapeutic agent can be, for example, an analgesic (e.g., an opioid agonist, aspirin, acetaminophen, non-steroidal anti-inflammatory drugs ("NSAIDS"), N-methyl-D-aspartate ("NMDA") receptor antagonists, cycooxygenase-II inhibitors ("COX-II inhibitors"), and glycine receptor antagonists), an antibacterial agent, an anti-viral agent, an anti-microbial agent, anti-infective agent, a chemotherapeutic, an immunosuppressive agent, an antitussive, an expectorant, a decongestant, an antihistamine drugs, a decongestant, antihistamine drugs, and the like. Preferably, the therapeutic agent is one that is addictive (physically and/or psychologically) upon repeated use and typically leads to abuse of the therapeutic agent. In this regard, the therapeutic agent can be any opioid agonist as discussed herein.

The therapeutic agent can be an opioid agonist. By "opioid" is meant to include a drug, hormone, or other chemical or biological substance, natural or synthetic, having a sedative, narcotic, or otherwise similar effect(s) to those containing opium or its natural or synthetic derivatives. By "opioid agonist," sometimes used herein interchangeably with terms "opioid" and "opioid analgesic," is meant to include one or more opioid agonists, either alone or in combination, and is further meant to include the base of the opioid, mixed or combined agonist-antagonists, partial agonists, pharmaceutically acceptable salts thereof, stereoisomers thereof, ethers thereof, esters thereof, and combinations thereof.

Opioid agonists include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydroetorphine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenazocine, phenomorphan, phenoperidine, piminodine, piritramide, propheptazine, promedol, properidine, propiram, propoxyphene, sufentanil, tramadol, tilidine, derivatives or complexes thereof, pharmaceutically acceptable salts thereof, and combinations thereof Preferably, the opioid agonist is selected from the group consisting of hydrocodone, hydromorphone, oxycodone, dihydrocodeine, codeine, dihydromorphine, morphine, buprenorphine, derivatives or complexes thereof, pharmaceutically acceptable salts thereof, and combinations thereof. Most preferably, the opioid agonist is morphine, hydromorphone, oxycodone or hydrocodone. In a preferred embodiment, the opioid agonist comprises oxycodone or hydrocodone and is present in the dosage form in an amount of about 15 to about 45 mg, and the opioid antagonist comprises naltrexone and is present in the dosage form in an amount of about 0.5 to about 5 mg.

Equianalgesic doses of these opioids, in comparison to a 15 mg dose of hydrocodone, are set forth in Table 1 below:

TABLE I

Equianalgesic Doses of Opioids

| Opioid | Calculated Dose (mg) |
|---|---|
| Oxycodone | 13.5 |
| Codeine | 90.0 |
| Hydrocodone | 15.0 |

TABLE I-continued

Equianalgesic Doses of Opioids

| Opioid | Calculated Dose (mg) |
|---|---|
| Hydromorphone | 3.375 |
| Levorphanol | 1.8 |
| Meperidine | 135.0 |
| Methadone | 9.0 |
| Morphine | 27.0 |

Hydrocodone is a semisynthetic narcotic analgesic and antitussive with multiple nervous system and gastrointestinal actions. Chemically, hydrocodone is 4,5-epoxy-3-methoxy-17-methylmorphinan-6-one, and is also known as dihydrocodeine. Like other opioids, hydrocodone can be habit-forming and can produce drug dependence of the morphine type. Like other opium derivatives, excess doses of hydrocodone will depress respiration.

Oral hydrocodone is also available in Europe (e.g., Belgium, Germany, Greece, Italy, Luxembourg, Norway and Switzerland) as an antitussive agent. A parenteral formulation is also available in Germany as an antitussive agent. For use as an analgesic, hydrocodone bitartrate is commonly available in the United States only as a fixed combination with non-opiate drugs (e.g., ibuprofen, acetaminophen, aspirin; etc.) for relief of moderate to moderately severe pain.

A common dosage form of hydrocodone is in combination with acetaminophen and is commercially available, for example, as Lortab® in the United States from UCB Pharma, Inc. (Brussels, Belgium), as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen and a 7.5 mg hydrocodone bitartrate and 750 mg acetaminophen. Hydrocodone, in combination with aspirin, is given in an oral dosage form to adults generally in 1-2 tablets every 4-6 hours as needed to alleviate pain. The tablet form is 5 mg hydrocodone bitartrate and 224 mg aspirin with 32 mg caffeine; or 5 mg hydrocodone bitartrate and 500 mg aspirin. Another formulation comprises hydrocodone bitartrate and ibuprofen. Vicoprofen®, commercially available in the U.S. from Knoll Laboratories (Mount Olive, N.J.), is a tablet containing 7.5 mg hydrocodone bitartrate and 200 mg ibuprofen. The invention is contemplated to encompass all such formulations, with the inclusion of the opioid antagonist and/or antagonist in sequestered form as part of a subunit comprising an opioid agonist.

Oxycodone, chemically known as 4,5-epoxy-14-hydroxy-3-methoxy-17-methylmorphinan-6-one, is an opioid agonist whose principal therapeutic action is analgesia. Other therapeutic effects of oxycodone include anxiolysis, euphoria and feelings of relaxation. The precise mechanism of its analgesic action is not known, but specific CNS opioid receptors for endogenous compounds with opioid-like activity have been identified throughout the brain and spinal cord and play a role in the analgesic effects of this drug.

Oxycodone is commercially available in the United States, e.g., as Oxycotin® from Purdue Pharma L.P. (Stamford, Conn.), as controlled-release tablets for oral administration containing 10 mg, 20 mg, 40 mg or 80 mg oxycodone hydrochloride, and as OxyIR™, also from Purdue Pharma L.P., as immediate-release capsules containing 5 mg oxycodone hydrochloride. The invention is contemplated to encompass all such formulations, with the inclusion of an opioid antagonist and/or antagonist in sequestered form as part of a subunit comprising an opioid agonist.

Oral hydromorphone is commercially available in the United States, e.g., as Dilaudid® from Abbott Laboratories (Chicago, Ill.). Oral morphine is commercially available in the United States, e.g., as Kadian® from Faulding Laboratories (Piscataway, N.J.).

Exemplary NSAIDS include ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well-known.

Exemplary NMDA receptor medicaments include morphinans, such as dexotromethorphan or dextrophan, ketamine, d-methadone, and pharmaceutically acceptable salts thereof, and encompass drugs that block a major intracellular consequence of NMDA-receptor activation, e.g., a ganglioside, such as (6-aminothexyl)-5-chloro-1-naphthalenesulfonamide. These drugs are stated to inhibit the development of tolerance to and/or dependence on addictive drugs, e.g., narcotic analgesics, such as morphine, codeine; etc., in U.S. Pat. Nos. 5,321,012 and 5,556,838 (both to Mayer et al.), both of which are incorporated herein by reference, and to treat chronic pain in U.S. Pat. No. 5,502,058 (Mayer et al.), incorporated herein by reference. The NMDA agonist can be included alone or in combination with a local anesthetic, such as lidocaine, as described in these patents by Mayer et al.

COX-2 inhibitors have been reported in the art, and many chemical compounds are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944 and 5,130,311, all of which are incorporated herein by reference. Certain preferred COX-2 inhibitors include celecoxib (SC-58635), DUP-697, flosulide (CGP-28238), meloxicam, 6-methoxy-2-naphthylacetic acid (6-NMA), MK-966 (also known as Vioxx), nabumetone (prodrug for 6-MNA), nimesulide, NS-398, SC-5766, SC-58215, T-614, or combinations thereof. Dosage levels of COX-2 inhibitor on the order of from about 0.005 mg to about 140 mg per kilogram of body weight per day have been shown to be therapeutically effective in combination with an opioid analgesic. Alternatively, about 0.25 mg to about 7 g per patient per day of a COX-2 inhibitor can be administered in combination with an opioid analgesic.

The treatment of chronic pain via the use of glycine receptor antagonists and the identification of such drugs is described in U.S. Pat. No. 5,514,680 (Weber et al.), which is incorporated herein by reference.

Pharmaceutically acceptable salts of the antagonist or agonist agents discussed herein include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N'-dibenzylethylenediamine salt, and the like; inorganic acid salts, such as hydrochloride, hydrobromide, sulfate, phosphate, and the like; organic acid salts, such as formate, acetate, trifluoroacetate, maleate, tartrate, and the like; sulfonates, such as methanesulfonate, benzenesulfonate, p-toluenesulfonate, and the like; amino acid salts, such as arginate, aspartinate, glutamate, and the like.

In embodiments in which the opioid agonist comprises hydrocodone, the sustained-release oral dosage forms can include analgesic doses from about 8 mg to about 50 mg of hydrocodone per dosage unit. In sustained-release oral dosage forms where hydromorphone is the therapeutically active opioid, it is included in an amount from about 2 mg to about 64 mg hydromorphone hydrochloride. In another embodiment, the opioid agonist comprises morphine, and the sustained-release oral dosage forms of the invention include from about 2.5 mg to about 800 mg morphine, by weight. In yet another embodiment, the opioid agonist comprises oxycodone and the sustained-release oral dosage forms include from about 2.5 mg to about 800 mg oxycodone. In certain preferred embodiments, the sustained-release oral dosage forms include from about 20 mg to about 30 mg oxycodone. Controlled release oxycodone formulations are known in the art. The following documents describe various controlled-release oxycodone formulations suitable for use in the invention described herein, and processes for their manufacture: U.S. Pat. Nos. 5,266,331; 5,549,912; 5,508,042; and 5,656,295, which are incorporated herein by reference. The opioid agonist can comprise tramadol and the sustained-release oral dosage forms can include from about 25 mg to 800 mg tramadol per dosage unit.

Methods of making any of the sequestering subunits of the invention are known in the art. See, for example, *Remington: The Science and Practice of Pharmacy*, Alfonso R. Genaro (ed), 20$^{th}$ edition, and Example 2 set forth below. The sequestering subunits can be prepared by any suitable method to provide, for example, beads, pellets, granules, spheroids, and the like. Spheroids or beads, coated with an active ingredient can be prepared, for example, by dissolving the active ingredient in water and then spraying the solution onto a substrate, for example, nu pariel 18/20 beads, using a Wurster insert. Optionally, additional ingredients are also added prior to coating the beads in order to assist the active ingredient in binding to the substrates, and/or to color the solution; etc. The resulting substrate-active material optionally can be overcoated with a barrier material to separate the therapeutically active agent from the next coat of material, e.g., release-retarding material. Preferably, the barrier material is a material comprising hydroxypropyl methylcellulose. However, any film-former known in the art can be used. Preferably, the barrier material does not affect the dissolution rate of the final product.

Pellets comprising an active ingredient can be prepared, for example, by a melt pelletization technique. Typical of such techniques is when the active ingredient in finely divided form is combined with a binder (also in particulate form) and other optional inert ingredients, and thereafter the mixture is pelletized, e.g., by mechanically working the mixture in a high shear mixer to form the pellets (e.g., pellets, granules, spheres, beads; etc., collectively referred to herein as "pellets"). Thereafter, the pellets can be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

The diameter of the extruder aperture or exit port also can be adjusted to vary the thickness of the extruded strands. Furthermore, the exit part of the extruder need not be round; it can be oblong, rectangular; etc. The exiting strands can be reduced to particles using a hot wire cutter, guillotine; etc.

The melt-extruded multiparticulate system can be, for example, in the form of granules, spheroids, pellets, or the like, depending upon the extruder exit orifice. The terms "melt-extended multiparticulate(s)" and "melt-extended multiparticulate system(s)" and "melt-extruded particles" are used interchangeably herein and include a plurality of sub-units, preferably within a range of similar size and/or shape. The melt-extended multiparticulates are preferably in a range of from about 0.1 to about 12 mm in length and have a diameter of from about 0.1 to about 5 mm. In addition, the melt-extruded multiparticulates can be any geometrical shape within this size range. Alternatively, the extrudate can simply be cut into desired lengths and divided into unit doses of the therapeutically active agent without the need of a spheronization step.

The substrate also can be prepared via a granulation technique. Generally, melt-granulation techniques involve melting a normally solid hydrophobic material, e.g., a wax, and incorporating an active ingredient therein. To obtain a sustained-release dosage form, it can be necessary to incorporate an additional hydrophobic material.

A coating composition can be applied onto a substrate by spraying it onto the substrate using any suitable spray equipment. For example, a Wurster fluidized-bed system can be used in which an air flow from underneath, fluidizes the coated material and effects drying, while the insoluble polymer coating is sprayed on. The thickness of the coating will depend on the characteristics of the particular coating composition, and can be determined by using routine experimentation.

Any manner of preparing a subunit can be employed. By way of example, a subunit in the form of a pellet or the like can be prepared by co-extruding a material comprising the opioid agonist and a material comprising the opioid antagonist and/or antagonist in sequestered form. Optionally, the opioid agonist composition can cover, e.g., overcoat, the material comprising the antagonist and/or antagonist in sequestered form. A bead, for example, can be prepared by coating a substrate comprising an opioid antagonist and/or an antagonist in sequestered form with a solution comprising an opioid agonist.

The sequestering subunits of the invention are particularly well-suited for use in compositions comprising the sequestering subunit and a therapeutic agent in releasable form. In this regard, the invention also provides a composition comprising any of the sequestering subunits of the invention and a therapeutic agent in releasable form. By "releasable form" is meant to include immediate release, intermediate release, and sustained-release forms. The therapeutic agent can be formulated to provide immediate release of the therapeutic agent. In preferred embodiments, the composition provides sustained-release of the therapeutic agent.

The therapeutic agent in sustained-release form is preferably a particle of therapeutic agent that is combined with a release-retarding material. The release-retarding material is preferably a material that permits release of the therapeutic agent at a sustained rate in an aqueous medium. The release-retarding material can be selectively chosen so as to achieve, in combination with the other stated properties, a desired in vitro release rate.

In a preferred embodiment, the oral dosage form of the invention can be formulated to provide for an increased duration of therapeutic action allowing once-daily dosing. In general, a release-retarding material is used to provide the increased duration of therapeutic action. Preferably, the once-daily dosing is provided by the dosage forms and methods described in U.S. Patent Application Pub. No. 20050020613 to Boehm, entitled "Sustained-Release Opioid Formulations and Method of Use," filed on Sep. 22, 2003, and incorporated herein by reference.

Preferred release-retarding materials include acrylic polymers, alkylcelluloses, shellac, zein, hydrogenated vegetable oil, hydrogenated castor oil, and combinations thereof. In certain preferred embodiments, the release-retarding material is a pharmaceutically acceptable acrylic polymer, including acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, and glycidyl methacrylate copolymers. In certain preferred embodiments, the acrylic polymer comprises one or more ammonio methacrylate copolymers. Ammonio methacrylate copolymers are well-known in the art, and are described in NF21, the 21$^{st}$ edition of the National Formulary, published by the United States Pharmacopeial Convention Inc. (Rockville, Md.), as fully polymerized copolymers of acrylic and methacrylic acid esters with a low content of quaternary ammonium groups. In other preferred embodiments, the release-retarding material is an alkyl cellulosic material, such as ethylcellulose. Those skilled in the art will appreciate that other cellulosic polymers, including other alkyl cellulosic polymers, can be substituted for part or all of the ethylcellulose.

Release-modifying agents, which affect the release properties of the release-retarding material, also can be used. In a preferred embodiment, the release-modifying agent functions as a pore-former. The pore-former can be organic or inorganic, and include materials that can be dissolved, extracted or leached from the coating in the environment of use. The pore-former can comprise one or more hydrophilic polymers, Such as hydroxypropylmethylcellulose. In certain preferred embodiments, the release-modifying agent is selected from hydroxypropylmethylcellulose, lactose, metal stearates, and combinations thereof.

The release-retarding material can also include an erosion-promoting agent, such as starch and gums; a release-modifying agent useful for making microporous lamina in the environment of use, such as polycarbonates comprised of linear polyesters of carbonic acid in which carbonate groups reoccur in the polymer chain; and/or a semi-permeable polymer.

The release-retarding material can also include an exit means comprising at least one passageway, orifice, or the like. The passageway can be formed by such methods as those disclosed in U.S. Pat. Nos. 3,845,770; 3,916,889; 4,063,064; and 4,088,864, which are incorporated herein by reference. The passageway can have any shape, such as round, triangular, square, elliptical, irregular; etc.

In certain embodiments, the therapeutic agent in sustained-release form can include a plurality of substrates comprising the active ingredient, which substrates are coated with a sustained-release coating comprising a release-retarding material.

The sustained-release preparations of the invention can be made in conjunction with any multiparticulate system, such as beads, ion-exchange resin beads, spheroids, microspheres, seeds, pellets, granules, and other multiparticulate systems in order to obtain a desired sustained-release of the therapeutic agent. The multiparticulate system can be presented in a capsule or in any other suitable unit dosage form.

In certain preferred embodiments, more than one multiparticulate system can be used, each exhibiting different characteristics, such as pH dependence of release, time for release in various media (e.g., acid, base, simulated intestinal fluid), release in vivo, size and composition.

To obtain a sustained-release of the therapeutic agent in a manner sufficient to provide a therapeutic effect for the sustained durations, the therapeutic agent can be coated with an amount of release-retarding material sufficient to obtain a weight gain level from about 2 to about 30%, although the coat can be greater or lesser depending upon the physical properties of the particular therapeutic agent utilized and the desired release rate, among other things. Moreover, there can be more than one release-retarding material used in the coat, as well as various other pharmaceutical excipients.

Solvents typically used for the release-retarding material include pharmaceutically acceptable solvents, such as water, methanol, ethanol, methylene chloride and combinations thereof.

In certain embodiments of the invention, the release-retarding material is in the form of a coating comprising an aqueous dispersion of a hydrophobic polymer. The inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentrations of the plasticizer, however, can be determined by routine experimentation.

Examples of plasticizers for ethylcellulose and other celluloses include dibutyl sebacate, diethyl phthalate, triethyl citrate, tributyl citrate, and triacetin, although it is possible that other plasticizers (such as acetylated monoglycerides, phthalate esters, castor oil; etc.) can be used.

Examples of plasticizers for the acrylic polymers include citric acid esters, such as triethyl citrate NF21, tributyl citrate, dibutyl phthalate, and possibly 1,2-propylene glycol, polyethylene glycols, propylene glycol, diethyl phthalate, castor oil, and triacetin, although it is possible that other plasticizers (such as acetylated monoglycerides, phthalate esters, castor oil; etc.) can be used.

The sustained-release profile of drug release in the formulations of the invention (either in vivo or in vitro) can be altered, for example, by using more than one release-retarding material, varying the thickness of the release-retarding material, changing the particular release-retarding material used, altering the relative amounts of release-retarding material, altering the manner in which the plasticizer is added (e.g., when the sustained-release coating is derived from an aqueous dispersion of hydrophobic polymer), by varying the amount of plasticizer relative to retardant material, by the inclusion of additional ingredients or excipients, by altering the method of manufacture; etc.

In certain other embodiments, the oral dosage form can utilize a multiparticulate sustained-release matrix. In certain embodiments, the sustained-release matrix comprises a hydrophilic and/or hydrophobic polymer, such as gums, cellulose ethers, acrylic resins and protein-derived materials. Of these polymers, the cellulose ethers, specifically hydroxyalkylcelluloses and carboxyalkylcelluloses, are preferred.

The oral dosage form can contain between about 1% and about 80% (by weight) of at least one hydrophilic or hydrophobic polymer.

The hydrophobic material is preferably selected from the group consisting of alkylcellulose, acrylic and methacrylic acid polymers and copolymers, shellac, zein, hydrogenated castor oil, hydrogenated vegetable oil, or mixtures thereof Preferably, the hydrophobic material is a pharmaceutically acceptable acrylic polymer, including acrylic acid and methacrylic acid copolymers, methyl methacrylate, methyl methacrylate copolymers, ethoxyethyl methacrylates, cyanoethyl methacrylate, aminoalkyl methacrylate copolymer, poly (acrylicacid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material can also include hydrooxyalkylcelluloses such as hydroxypropylmethylcellulose and mixtures of the foregoing.

Preferred hydrophobic materials are water-insoluble with more or less pronounced hydrophobic trends. Preferably, the hydrophobic material has a melting point from about 30° C. to about 200° C., more preferably from about 45° C. to about 90° C. The hydrophobic material can include neutral or synthetic waxes, fatty alcohols (such as lauryl, myristyl, stearyl, cetyl or preferably cetostearyl alcohol), fatty acids, including fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include beeswax, glycowax, castor wax, carnauba wax and wax-like substances, e.g., material normally solid at room temperature and having a melting point of from about 30° C. to about 100° C.

Preferably, a combination of two or more hydrophobic materials are included in the matrix formulations. If an additional hydrophobic material is included, it is preferably a natural or synthetic wax, a fatty acid, a fatty alcohol, or mixtures thereof. Examples include beeswax, carnauba wax, stearic acid and stearyl alcohol.

In other embodiments, the sustained-release matrix comprises digestible, long-chain (e.g., $C_9$-$C_{50}$, preferably $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between about 25° C. and about 90° C. are preferred. Of these long-chain hydrocarbon materials, fatty (aliphatic) alcohols are preferred. The oral dosage form can contain up to about 60% (by weight) of at least one digestible, long-chain hydrocarbon.

Further, the sustained-release matrix can contain up to 60% (by weight) of at least one polyalkylene glycol.

In a preferred embodiment, the matrix comprises at least one water-soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$-$C_6$) alkyl cellulose, such as hydroxypropylcellulose, hydroxypropylmethylcellulose and, preferably, hydroxyethyl cellulose. The amount of the at least one hydroxyalkyl cellulose in the oral dosage form will be determined, amongst other things, by the precise rate of opioid release required. The amount of the at least one aliphatic alcohol in the present oral dosage form will be determined by the precise rate of opioid release required. However, it will also depend on whether the at least one polyalkylene glycol is absent from the oral dosage form.

In certain embodiments, a spheronizing agent, together with the active ingredient, can be spheronizing to form spheroids. Microcrystalline cellulose and hydrous lactose impalpable are examples of such agents. Additionally (or alternatively), the spheroids can contain a water-insoluble polymer, preferably an acrylic polymer, an acrylic copolymer, such as a methacrylic acid-ethyl acrylate copolymer, or ethyl cellulose. In such embodiments, the sustained-release coating will generally include a water-insoluble material such as (a) a wax, either alone or in admixture with a fatty alcohol, or (b) shellac or zein.

Preferably, the sequestering subunit comprises the therapeutic agent in sustained-release form. The sustained-release subunit can be prepared by any suitable method. For example, a plasticized aqueous dispersion of the release-retarding material can be applied onto the subunit comprising the opioid agonist. A sufficient amount of the aqueous dispersion of release-retarding material to obtain a predetermined sustained-release of the opioid agonist when the coated substrate is exposed to aqueous solutions, e.g., gastric fluid, is preferably applied, taking into account the physical characteristics of the opioid agonist, the manner of incorporation of the plasticizer; etc. Optionally, a further overcoat of a film-former, such as Opadry (Colorcon, West Point, Va.), can be applied after coating with the release-retarding material.

The subunit can be cured in order to obtain a stabilized release rate of the therapeutic agent. In embodiments employing, an acrylic coating, a stabilized product can be preferably obtained by subjecting the subunit to oven curing at a temperature above the glass transition temperature of the plasticized acrylic polymer for the required time period. The optimum temperature and time for the particular formulation can be determined by routine experimentation.

Once prepared, the subunit can be combined with at least one additional subunit and, optionally, other excipients or drugs to provide an oral dosage form.

In addition to the above ingredients, a sustained-release matrix also can contain suitable quantities of other materials, e.g., diluents, lubricants, binders, granulating aids, colorants, flavorants and glidants that are conventional in the pharmaceutical art.

Optionally and preferably, the mechanical fragility of any of the sequestering subunits described herein is the same as the mechanical fragility of the therapeutic agent in releasable form. In this regard, tampering with the composition of the invention it) a manner to obtain the therapeutic agent will result in the destruction of the sequestering, subunit, such that the antagonist is released and mixed in with the therapeutic agent. Consequently, the antagonist cannot be separated from the therapeutic agent, and the therapeutic agent cannot be administered in the absence of the antagonist. Methods of assaying the mechanical fragility of the sequestering subunit and of a therapeutic agent are known in the art.

The composition of the invention can be in any suitable dosage form or formulation, (see, e.g., *Pharmaceutics and Pharmacy Practice*, J. B. Lippincott Company, Philadelphia, Pa., Banker and Chalmers, eds., pages 238-250 (1982)). Formulations suitable for oral administration can consist of (a) liquid Solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

One of ordinary skill in the art will readily appreciate that the compositions of the invention can be modified in any number of ways, such that the therapeutic efficacy of the composition is increased through the modification. For instance, the therapeutic agent or sequestering subunit could be conjugated either directly or indirectly through a linker to a targeting moiety. The practice of conjugating therapeutic agents or sequestering subunits to targeting moieties is known in the art. See, for instance, Wadwa et al., *J. Drug Targeting* 3:111 (1995), and U.S. Pat. No. 5,087,616. The term "targeting moiety" as used herein, refers to any molecule or agent that specifically recognizes and binds to a cell-surface receptor, such that the targeting moiety directs the delivery of the therapeutic agent or sequestering subunit to a population of cells on which the receptor is expressed. Targeting moieties include, but are not limited to, antibodies, or fragments thereof, peptides, hormones, growth factors, cytokines, and any other naturally- or non-naturally-existing ligands, which bind to cell-surface receptors. The term "linker" as used herein, refers to any agent or molecule that bridges the therapeutic agent or sequestering subunit to the targeting moiety. One of ordinary skill in the art recognizes that sites on the therapeutic agent or sequestering subunit, which are not necessary for the function of the agent or sequestering subunit, are ideal sites for attaching a linker and/or a targeting moiety, provided that the linker and/or targeting moiety, once attached to the agent or sequestering subunit, do(es) not interfere with the function of the therapeutic agent or sequestering subunit.

With respect to the present inventive compositions, the composition is preferably an oral dosage form. By "oral dosage form" is meant to include a unit dosage form prescribed or intended for oral administration comprising subunits. Desirably, the composition comprises the sequestering subunit coated with the therapeutic agent in releasable form, thereby forming a composite subunit comprising the sequestering subunit and the therapeutic agent. Accordingly, the invention further provides a capsule suitable for oral administration comprising a plurality of such composite subunits.

Alternatively, the oral dosage form can comprise any of the sequestering subunits of the invention in combination with a therapeutic agent subunit, wherein the therapeutic agent subunit comprises the therapeutic agent in releasable form. In this respect, the invention provides a capsule suitable for oral administration comprising a plurality of sequestering subunits of the invention and a plurality of therapeutic subunits, each of which comprises a therapeutic agent in releasable form.

The invention further provides tablets comprising a sequestering subunit of the invention and a therapeutic agent in releasable form. For instance, the invention provides a tablet suitable for oral administration comprising a first layer comprising any of the sequestering subunits of the invention and a second layer comprising therapeutic agent in releasable form, wherein the first layer is coated with the second layer. The first layer can comprise a plurality of sequestering subunits. Alternatively, the first layer can be or can consist of a single sequestering subunit. The therapeutic agent in releasable form can be in the form of a therapeutic agent subunit and the second layer can comprise a plurality of therapeutic subunits. Alternatively, the second layer can comprise a single substantially homogeneous layer comprising the therapeutic agent in releasable form.

When the blocking agent is a system comprising a first antagonist-impermeable material and a core, the sequestering subunit can be in one of several different forms. For example, the system can further comprise a second antagonist-impermeable material, in which case the sequestering unit comprises an antagonist, a first antagonist-impermeable material, a second antagonist-impermeable material, and a core. In this instance, the core is coated with the first antagonist-impermeable material, which, in turn, is coated with the antagonist, which, in turn, is coated with the second antagonist-impermeable material. The first antagonist-impermeable material and second antagonist-impermeable material substantially prevent release of the antagonist from the sequestering subunit in the gastrointestinal tract for a time period that is greater than 24 hours. In some instances, it is preferable that the first antagonist-impermeable material is the same as the second antagonist-impermeable material. In other instances, the first antagonist-impermeable material is different from the second antagonist-impermeable material. It is within the skill of the ordinary artisan to determine whether or not the first and second antagonist-impermeable materials should be the same or different. Factors that influence the decision as to whether the first and second antagonist-impermeable materials should be the same or different can include whether a layer to be placed over the antagonist-impermeable material requires certain properties to prevent dissolving part or all of the antagonist-impermeable layer when applying the next layer or properties to promote adhesion of a layer to be applied over the antagonist-impermeable layer.

Alternatively, the antagonist can be incorporated into the core, and the core is coated with the first antagonist-impermeable material. In this case, the invention provides a sequestering subunit comprising an antagonist, a core and a first antagonist-impermeable material, wherein the antagonist is incorporated into the core and the core is coated with the first antagonist-impermeable material, and wherein the first antagonist-impermeable material substantially prevents release of the antagonist from the sequestering subunit in the gastrointestinal tract for a time period that is greater than 24 hours. By "incorporate" and words stemming therefrom, as used herein is meant to include any means of incorporation, e.g., homogeneous dispersion of the antagonist throughout the core, a single layer of the antagonist coated on top of a core, or a multi-layer system of the antagonist, which comprises the core.

In another alternative embodiment, the core comprises a water-insoluble material, and the core is coated with the antagonist, which, in turn, is coated with the first antagonist-impermeable material. In this case, the invention further provides a sequestering subunit comprising an antagonist, a first antagonist-impermeable material, and a core, which comprises a water-insoluble material, wherein the core is coated with the antagonist, which, in turn, is coated with the first antagonist-impermeable material, and wherein the first antagonist-impermeable material substantially prevents release of the antagonist from the sequestering subunit in die gastrointestinal tract for a time period that is greater than 24 hours. The term "water-insoluble material" as used herein means any material that is substantially water-insoluble. The term "substantially water-insoluble" does not necessarily refer to complete or 100% water-insolubility. Rather, there are varying degrees of water insolubility of which one of ordinary skill in the art recognizes as having a potential benefit. Preferred water-insoluble materials include, for example, microcrystalline cellulose, a calcium salt, and a wax. Calcium salts include, but are not limited to, a calcium phosphate (e.g., hydroxyapatite, apatite; etc.), calcium carbonate, calcium sulfate, calcium stearate, and the like. Waxes include, for example, carnuba wax, beeswax, petroleum wax, candelilla wax, and the like.

In one embodiment, the sequestering subunit includes an antagonist and a seal coat where the seal coat forms a layer physically separating the antagonist within the sequestering subunit from the agonist which is layered upon the sequestering subunit. In one embodiment, the seal coat comprises one or more of an osmotic pressure regulating agent, a change-neutralizing additive, a sequestering polymer hydrophobicity-enhancing additive, and a first sequestering polymer (each having been described above). In such embodiments, it is preferred that the osmotic pressure regulating agent, charge-neutralizing additive, and/or sequestering polymer hydrophobicity-enhancing additive, respectively where present; are present in proportion to the first sequestering polymer such that no more than 10% of the antagonist is released from the intact dosage form. Where an opioid antagonist is used in the sequestering subunit and the intact dosage form includes an opioid agonist, it is preferred that ratio of the osmotic pressure regulating agent, charge-neutralizing additive, and/or sequestering polymer hydrophobicity-enhancing additive, respectively where present, in relation to the first sequestering polymer is such that the physiological effect of the opioid agonist is not diminished when the composition is in its intact dosage form or during the normal course digestion in the patient. Release may be determined as described above using the USP paddle method (optionally using a buffer containing, a surfactant such as Triton X-100) or measured from plasma after administration to a patient in the fed or non-fed state. In one embodiment, plasma naltrexone levels are determined; in others, plasma 6-beta naltrexol levels are determined. Standard tests may be utilized to ascertain the antagonist's effect on agonist function (i.e., reduction of pain).

The sequestering subunit of the invention can have a blocking agent that is a tether to which the antagonist is attached. The term "tether" as used herein refers to any means by which the antagonist is tethered or attached to the interior of the sequestering subunit, such that the antagonist is not released, unless the sequestering subunit is tampered with. In this instance, a tether-antagonist complex is formed. The complex is coated with a tether-impermeable material, thereby substantially preventing release of the antagonist from the subunit. The term "tether-impermeable material" as used herein refers to any material that substantially prevents or prevents the tether from permeating through the material. The tether preferably is an ion exchange resin bead.

The invention further provides a tablet suitable for oral administration comprising a single layer comprising a therapeutic agent in releasable form and a plurality of any of the sequestering subunits of the invention dispersed throughout the layer of the therapeutic agent in releasable form. The invention also provides a tablet in which the therapeutic agent in releasable form is in the form of a therapeutic agent subunit and the tablet comprises an at least substantially homogeneous mixture of a plurality of sequestering subunits and a plurality of subunits comprising the therapeutic agent.

In preferred embodiments, oral dosage forms are prepared to include an effective amount of melt-extruded subunits in the form of multiparticles within a capsule. For example, a plurality of the melt-extruded multiparticulates can be placed in a gelatin capsule in an amount sufficient to provide an effective release dose when ingested and contacted by gastric fluid.

In another preferred embodiment, the subunits, e.g., in the form of multiparticulates, can be compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Aurther Osol., editor), 1553-1593 (1980), which is incorporated herein by reference. Excipients in tablet formulation can include, for example, an inert diluent such as lactose, granulating and disintegrating agents, such as cornstarch, binding agents, such as starch, and lubricating agents, such as magnesium stearate.

In yet another preferred embodiment, the subunits are added during the extrusion process and the extrudate can be shaped into tablets as set forth in U.S. Pat. No. 4,957,681 (Klimesch et al.), which is incorporated herein by reference.

Optionally, the sustained-release, melt-extruded, multiparticulate systems or tablets can be coated, or the gelatin capsule can be further coated, with a sustained-release coating, such as the sustained-release coatings described herein. Such coatings are particularly useful when the subunit comprises an opioid agonist in releasable form, but not in sustained-release form. The coatings preferably include a sufficient amount of a hydrophobic material to obtain a weight gain level form about 2 to about 30 percent, although the overcoat can be greater, depending upon the physical properties of the particular opioid analgesic utilized and the desired release rate, among other things.

The melt-extruded dosage forms can further include combinations of melt-extruded multiparticulates containing one or more of the therapeutically active agents before being encapsulated. Furthermore, the dosage forms can also include an amount of an immediate release therapeutic agent for prompt therapeutic effect. The immediate release therapeutic agent can be incorporated or coated on the surface of the subunits after preparation of the dosage forms (e.g., controlled-release coating or matrix-based). The dosage forms can also contain a combination of controlled-release beads and matrix multiparticulates to achieve a desired effect.

The sustained-release formulations preferably slowly release the therapeutic agent, e.g., when ingested and exposed to gastric fluids, and then to intestinal fluids. The sustained-release profile of the melt-extruded formulations can be altered, for example, by varying the amount of retardant, e.g., hydrophobic material, by varying the amount of plasticizer relative to hydrophobic material, by the inclusion of additional ingredients or excipients, by altering the method of manufacture; etc.

In other embodiments, the melt-extruded material is prepared without the inclusion of the subunits, which are added thereafter to the extrudate. Such formulations can have the subunits and other drugs blended together with the extruded matrix material, and then the mixture is tableted in order to provide a slow release of the therapeutic agent or other drugs. Such formulations can be particularly advantageous, for example, when the therapeutically active agent included in the formulation is sensitive to temperatures needed for softening the hydrophobic material and/or the retardant material.

In certain embodiments, the release of the antagonist of the sequestering subunit or composition is expressed in terms of a ratio of the release achieved after tampering, e.g., by crushing or chewing, relative to the amount released from the intact formulation. The ratio is, therefore, expressed as [Crushed]:[Whole], and it is desired that this ratio have a numerical range of at least about 4:1 or greater (e.g., crushed release within 1 hour/intact release in 24 hours). In certain embodiments, the ratio of the therapeutic agent and the antagonist, present in the sequestering subunit, is about 1:1, about 50:1, about 75:1, about 100:1, about 150:1, or about 200:1, for example, by weight, preferably about 1:1 to about 20:1 by weight or 15:1 to about 30:1 by weight. The weight ratio of the therapeutic agent to antagonist refers to the weight of the active ingredients. Thus, for example, the weight of the therapeutic agent excludes the weight of the coating, matrix, or other component that renders the antagonist sequestered, or other possible excipients associated with the antagonist particles. In certain preferred embodiments, the ratio is about 1:1 to about 10:1 by weight. Because in certain embodiments the antagonist is in a sequestered from, the amount of such antagonist within the dosage form can be varied more widely than the therapeutic agent/antagonist combination dosage forms, where both are available for release upon administration, as the formulation does not depend on differential metabolism or hepatic clearance for proper functioning. For safety reasons, the amount of the antagonist present in a substantially non-releasable form is selected as not to be harmful to humans, even if fully released under conditions of tampering.

The compositions of the invention are particularly well-suited for use in preventing abuse of a therapeutic agent. In this regard, the invention also provides a method of preventing abuse of a therapeutic agent by a human being. The method comprises incorporating the therapeutic agent into any of the compositions of the invention. Upon administration of the composition of the invention to the person, the antagonist is substantially prevented from being released in the gastrointestinal tract for a time period that is greater than 24 hours. However, if a person tampers with the compositions, the sequestering subunit, which is mechanically fragile, will break and thereby allow the antagonist to be released. Since the mechanical fragility of the sequestering subunit is the same as the therapeutic agent in releasable form, the antagonist will be mixed with the therapeutic agent, such that separation between the two components is virtually impossible.

The effectiveness of treatment of chronic moderate to severe pain (focusing on osteoarthritis of the hip or knee) is typically measured by mean change in diary Brief Pain Inventory (BPI) score of average pain (daily scores of average pain averaged over 7 days; in-clinic BPI and/or daily diary BPI (worst, least, and current pain)), WOMAC Osteoarthritis Index, Medical Outcomes Study (MOS) Sleep Scale, Beck Depression Inventory, and Patient Global Impression of Change (PGIC). The safety and tolerability of opioid medications such as Kadian NT are compared to placebo using Adverse Events (AEs), clinical laboratory data, vital signs, and two measures of opioid withdrawal: Subjective Opiate Withdrawal Scale (SOWS) and Clinical Opiate Withdrawal Scale (COWS).

BPI is typically measured using 11-point BPI system according the following questions: 1. Please rate your pain by circling the one number that best describes your pain at its worst in the last 24 hours. Pain Scale 0=no pain up to 10=Pain as bad as you can imagine. 2. Please rate your pain by circling the one number that best describes your pain at its least in the last 24 hours. Pain Scale 0=no pain up to 10=Pain as bad as you can imagine. 3. Please rate your pain by circling the one number that tells how much pain you have right now. Pain Scale 0=no pain up to 10=Pain as bad as you can imagine.

The MOS Sleep Scale is a self administered, subject rated questionnaire consisting of 12 items that assess key components of sleep (R. D., & Stewart, A. L. (1992). Sleep Measures. In A. L. Stewart & J. E. Ware (eds.), Measuring functioning and well being: The Medical Outcomes Study approach (pp. 235-259), Durham, N.C.: Duke University Press). When scored, the instrument provides seven subscale scores (sleep disturbance, snoring, awaken short of breath or with a headache, quantity of sleep, sleep adequacy, and somnolence) as well as a nine-item overall sleep adequacy, where a higher score reflects more impairment in all subscales except for sleep adequacy, where a higher score reflects less impairment. A typical representation of the MOS Sleep Scale is as follows: Question 1. How long did it usually take for you to fall asleep during the past four weeks (circle one): 1-15 minutes (1); 16-30 minutes (2); 31-45 minutes (3); 46-60 minutes (4); more than 60 minutes (5). Question 2: How often during the past four weeks did you feel that your sleep was not quiet (moving restlessly, feeling tense, speaking, etc., while sleeping)? All of the time (1); Most of the time (2); A good bit of the time (3); Some of the time (4); A little of the time (5) and None of the time (6). Question 3: How often during the past four weeks did you get enough sleep to feel rested upon waking in the morning? All of the time (1); Most of the time (2); A good bit of the time (3); Some of the time (4); A little of the time (5) and None of the time (6). Question 4: How often during the past four weeks did you awaken short of breath or with a headache? All of the time (1); Most of the time (2); A good bit of the time (3); Some of the time (4); A little of the time (5) and None of the time (6). Question 5: How often during the past four weeks did you feel drowsy or sleepy during the day? All of the time (1); Most of the time (2); A good bit of the time (3); Some of the time (4); A little of the time (5) and None of the time (6). Question 6: How often during the past four weeks did you have trouble falling asleep? All of the time (1); Most of the time (2); A good bit of the time (3); Some of the time (4); A little of the time (5) and None of the time (6). Question 7: How often in the past four weeks did you awaken during your sleep time and have trouble falling asleep again? All of the time (1); Most of the time (2); A good bit of the time (3); Some of the time (4); A little of the time (5) and None of the time (6). Question 8: How often in the past four weeks did you have trouble staying awake during the day? All of the time (1); Most of the time (2); A good bit of the time (3); Some of the time (4); A little of the time (5) and None of the time (6). Question 9: How often in the past four weeks did you snore during your sleep? All of the time (1); Most of the time (2); A good bit of the time (3); Some of the time (4); A little of the time (5) and None of the time (6). Question 10: How often in the past four weeks did you take naps (5 minutes or longer) during the day? All of the time (1); Most of the time (2); A good bit of the time (3); Some of the time (4); A little of the time (5) and None of the time (6). Question 11: How often in the past four weeks did you get the amount of sleep you needed? All of the time (1); Most of the time (2); A good bit of the time (3); Some of the time (4); A little of the time (5) and None of the time (6).

The Beck Depression Inventory is a self-administered, 21-item test in multiple-choice format that measures the presence and degree of depression (Beck et al. An inventory for measuring depression. Arch Gen Psych. 1961;4:561-571).

Each of the inventory questions corresponds to a specific category of depressive symptom and/or attitude. Answers are scored on a 0 to 3 scale, where "0" is minimal and "3" is severe. A score of <15 indicates mild depression, a score of 15-30 indicates moderate depression, and a score >30 indicates severe depression.

The WOMAC Osteoarthritis Index consists of questions on three subscales: Pain, Stiffness, and Physical Function (Bellamy et al. Validation study of WOMAC: a health Status instrument for measuring clinically important patient relevant outcomes to antirheumatic drug therapy in patients with osteoarthritis of the hip or knee. J Rheumatol. 1988;15:1833-1840; Bellamy N. Pain assessment in osteoarthritis: experience with the WOMAC osteoarthritis index. Semin Arthritis Rheum. 1989;18:14-17; Bellamy et al. Double blind randomized controlled trial of sodium meclofenamate (Meclomen) and diclofenac sodium (Voltaren): post validation reapplication of the WOMAC Osteoarthritis index. J Rheumatol. 1992; 19:153-159). Questions are typically completed by the subject before any other efficacy assessments are performed. A typical WOMAC survey is reproduced below:

The PGIC is a self-administered instrument that measures change in patient's overall status on a scale ranging from 1 (very much improved) to 7 (very much worse). The PGIC is based on the Clinical Global Impression of Change (CGIC) (Guy W. ECDEU assessment manual for psychopharmacology. Washington, D.C.: Department of Health, Education and Welfare, 1976; 217-222. Publication Number (ADM) 76-338), which is a validated scale. A typical form of the PGIC survey is shown below:

How would you rate your overall status since your last visit (please circle one): very much improved (1); Much improved (2); Minimally improved (3); No Change (4); Minimally Worse (5); Much Worse (6); Very Much Worse (7).

Any or all of these measures of effectiveness may be used alone or in combination to determine the efficacy of various formulations or treatment regimens. Provided herein are methods for treating pain in a person comprising administering thereto a multilayer pharmaceutical composition as described herein such that pain is substantially relieved in the patient. By "substantially relieved" is meant that the person reports a decrease in pain as measured by any of several known methods (including but not limited to those described herein) for determining pain. This decrease may be in comparison to no treatment, a placebo, or another form of treatment including but not limited to another composition, either one described herein or otherwise available to one of skill in the art. Typically but not necessarily, pain is considered substantially relieved where the decrease is significant (e.g., p<0.05). The methods described herein provide methods for substantially relieving pain (e.g., providing an analgesic effect) for time periods of at least one week (e.g., two, four, eight, 12, 16, 20, 24, 28, 32, 36, 40 and 100 weeks) by administering a multi-layer pharmaceutical composition as described herein. In one embodiment, the method includes regularly administering (e.g., at least once, twice, three, or four times daily) a multi-layer pharmaceutical composition comprising an agonist and an atagonist as described herein for at least one week (e.g., one, two, four, eight, 12, 16, 20, 24, 28, 32, 36, 40 and 100 weeks) wherein no substantial release (e.g., zero, or less than about 10%, 20%, or 30% release) of the antagonist is observed. In some embodiments, administration of the composition to a population once daily for a time period of at least one week results in no substantial release in at least about 90%, 80%, 70%, 60%, or 50% of the individuals making up the population. Release may be measured by detecting naltrexone or β-naltrexol in plasma.

A better understanding of the present invention and of its many advantages will be had from the following examples, given by way of illustration.

EXAMPLES

Exemplary KadianNT formulations and methods described below in Examples 1-4 may also be found in PCT/US2007/014282 (WO 2007/149438 A2), PCT/US2007/021627 (WO 2008/063301 A2), and PCT/US08/10357.

Example 1

Optimization Study #4, KadianNT, Morphine sulfate and Naltrexone HCl 60 mg/4.8 mg (20-780-1N)

| | PI-1495 | | PI-1496 | |
|---|---|---|---|---|
| | mg/unit | Percent | mg/unit | Percent |
| Sealed-coated sugar spheres | | | | |
| Sugar spheres (#25-30 mesh) | 37.2 | 11.7 | 37.1 | 11.9 |
| Ethylcellulose N50 | 6.2 | 1.9 | 6.2 | 2.0 |
| Mag Stearate | 2.5 | 0.8 | 2.5 | 0.8 |
| DBS | 0.6 | 0.2 | 0.6 | 0.2 |
| Talc | 15.5 | 4.9 | 15.5 | 5.0 |
| Subtotal | 62.0 | 19.4 | 61.9 | 19.9 |
| Naltrexone cores | | | | |
| Sealed sugar spheres | (62.0) | (19.4) | (61.9) | (19.9) |
| Naltrexone HCl | 4.8 | 1.50 | 4.8 | 1.54 |
| HPC (Klucel LF) | 0.9 | 0.3 | 0.9 | 0.3 |
| Ascorbic acid | 0.5 | 0.2 | 0.5 | 0.2 |
| Talc | 2.27 | 0.7 | 2.24 | 0.7 |
| Subtotal | 70.5 | 22.1 | 70.3 | 2.6 |
| Naltrexone pellets | | | | |
| Naltrexone cores | (70.5) | (22.1) | (70.3) | (22.6) |
| Eudragit RS PO | 53.3 | 16.7 | 53.3 | 17.1 |
| SLS | 1.8 | 0.6 | 1.8 | 0.6 |
| DBS | 5.36 | 1.7 | 5.36 | 1.7 |
| Talc | 52.1 | 16.3 | 52.1 | 16.8 |
| Subtotal | 183.0 | 57.4 | 182.9 | 58.8 |
| Naltrexone-morphine cores | | | | |
| Naltrexone pellets | (183.0) | (57.4) | (182.9) | (58.8) |
| Morphine sulfate | 59.9 | 18.8 | 59.7 | 19.2 |
| Sodium chloride | 11.2 | 3.5 | | |
| HPC (Klucel LF) | 73 | 2.3 | 4.76 | 1.5 |
| HPMC, 3 cps | | | 7.6 | 2.4 |
| Subtotal | 261.4 | 82.0 | 255.0 | 82.0 |
| Naltrexone-morphine pellets | | | | |
| Naltrexone-morphine cores | (261.4) | (82.0) | (255.0) | (82.0) |
| Ethylcellulose N50 | 19.81 | 6.2 | 19.31 | 6.2 |
| PEG 6000 | 9.16 | 2.9 | 8.9 | 2.9 |
| Eudragit L100-55 | 4.3 | 1.3 | 4.2 | 1.4 |
| DEP | 4.12 | 1.3 | 4 | 1.3 |
| Talc | 20.13 | 6.3 | 19.62 | 6.3 |
| Total | 319.0 | 100.0 | 311.0 | 100.0 |

A. Method of Preparation—
  1. Dissolve Ethylcellulose and dibutyl sebacate into ethanol, then disperse talc and magnesium stearate into the solution.
  2. Spray the dispersion from 1 onto sugar spheres in a Wurster to form seal-coated sugar spheres (50 μm seal coat).

3. Dissolve Klucel LF and ascorbic acid into 20:80 mixture of water and ethanol. Disperse naltrexone HCl and talc into the solution.
4. Spray the naltrexone dispersion from 3 onto seal-coated sugar spheres from 2 in a Wurster to form naltrexone cores.
5. Dissolve Eudragit RS, sodium lauryl sulfate and dibutyl debacate into ethanol. Disperse talc into the solution.
6. Spray the dispersion from 5 onto naltrexone cores from 4 in a Wurster to form naltrexone pellets.
7. The Naltrexone pellets are dried at 50° C. for 48 hours.
8. Resulting pellets have a Eudragit RS coat thickness of 150 μm for both PI-1495 PI-1496.
9. (Only for PI-1495) Dissolve sodium chloride and hypromellose into water.
10. Dissolve hypromellose into 10:90 mixture of water and ethanol. Disperse morphine sulfate into the solution.
11. (Only for PI-1495) Spray the solution from 9 followed by the dispersion from 10 onto naltrexone pellets in 7 in a rotor to form naltrexone-morphine cores.
12. (Only for PI-1496) Spray the dispersion from 10 onto naltrexone pellets in 7 in a rotor to form naltrexone-morphine cores.
13. Dissolve ethylcellulose, PEG 6000, Eudragit L100-55 and diethyl phthalate into ethanol. Disperse talc into the solution.
14. Spray the dispersion from 12 onto naltrexone-morpholine cores in 11 or 12 to form naltrexone-morphine pellets.
15. The pellets are filled into capsules.

B. In-Vitro Drug Release—
1. Method—USP paddle method at 37° C. and 100 rpm
   1 hour in 0.1 N HCl, then 72 hours in 0.05M pH 7.5 phosphate buffer
   Results—Percent of NT released at 73 hours for PI-1495=0%
   Percent of NT released at 73 hours for PI-1496=0%
2. Method—USP paddle method at 37° C. and 100 rpm
   72 hrs in 0.2% Triton X-100/0.2% sodium acetate/0.002N HCl, pH 5.5
   Results—Percent of NT released at 73 hours for PI-1495=0%
   Percent of NT released at 73 hours for PI-1496=0%

C. In-Vivo Study

This is a single-dose, open-label, two period study in which two groups of eight subjects received one dose of either PI-1495 or PI-1496. Each subject received an assigned treatment sequence based on a randomization schedule under fasting and non-fasting conditions. Blood samples were drawn prior to dose administration and at 0.5 to 168 hours post-dose. Limits of quantitation are 4.00 pg/mL for naltrexone and 0.250 pg/mL for 6-beta-naltrexol. A summary of the pharmacokinetic results is shown in the following tables.

| | Naltrexone | | | |
|---|---|---|---|---|
| | PI-1495 | | PI-1496 | |
| | Fast | Fed | Fast | Fed |
| Tmax (hr) | 54.00 (N = 2) | 14.34 (N = 3) | 55.20 (N = 5) | 41.60 (N = 5) |
| Cmax (pg/mL) | 8.53 | 6.32 (N = 7) | 24.23 (N = 7) | 45.67 (N = 5) |
| $AUC_{last}$ (pg * h/mL) | 100.8 | 75.9 (N = 7) | 500.6 (N = 7) | 1265 (N = 7) |
| $AUC\infty$ (pg * h/mL) | — | — | 2105.3 (N = 2) | 3737 (N = 2) |
| $T^{1/2}$ (hr) | — | — | 44.56 (N = 2) | 33.17 (N = 2) |
| Relative Bioavailability to an oral solution (Dose-adjusted) | | | | |
| Cmax Ratio (Test/Solution) | 0.29% | 0.21% | 0.82% | 1.55% |
| $AUC_{last}$ Ratio (Test/Solution) | 1.13% | 0.85% | 5.61% | 14.17% |
| $AUC\infty$ Ratio (Test/Solution) | — | — | 22.0% | 39.1% |

N = 8, unless specified otherwise

| | 6-beta-Naltrexol | | | |
|---|---|---|---|---|
| | PI-1495 | | PI-1496 | |
| | Fast | Fed | Fast | Fed |
| Tmax (hr) | 69.00 | 41.44 (N = 7) | 70.51 | 67.63 |
| Cmax (pg/mL) | 116.3 | 151.7 (N = 7) | 303.3 | 656.7 |
| $AUC_{last}$ (pg * h/mL) | 5043 | 7332 (N = 7) | 14653 | 27503 |
| $AUC\infty$ (pg * h/mL) | 5607 | 8449 (N = 6) | 14930 | 27827 |
| $T^{1/2}$ (hr) | 20.97 | 16.69 (N = 7) | 16.29 | 22.59 |
| Relative Bioavailability to an oral solution (Dose-adjusted) | | | | |
| Cmax Ratio (Test/Solution) | 0.47% | 0.62% | 1.23% | 2.67% |
| $AUC_{last}$ Ratio (Test/Solution) | 2.45% | 3.45% | 7.12% | 13.36% |
| $AUC\infty$ Ratio (Test/Solution) | 2.64% | 3.97% | 7.02% | 13.08% |

N = 8, unless specified otherwise

Kadian NT pellets with naltrexone pellet coat thickness of 150 μm had comparable naltrexone release as NT pellets with 90 μm coat thickness. This comparable NT release may also be attributed from the presence of 50 μm seal coat on the sugar spheres used in Kadian NT pellets. Significant NT sequestering was observed, both at fasting (>97%) and fed states (>96%). Kadian NT pellets containing sodium chloride immediately above the naltrexone pellet coat (PI-1495) had half the release of naltrexone compared to Kadian NT pellet without sodium chloride (PI-1496), consistent with in vitro results. There is again food effect observed. Lag time was significantly reduced.

Example 2

| Optimization Study #5, KadianNT, Morphine sulfate and Naltrexone HCl 60 mg/2.4 mg (20-903-AU) | | |
|---|---|---|
| | PI-1510 | |
| | Mg/unit | Percent |
| Sealed sugar spheres | | |
| Sugar spheres (#25-30 mesh) | 39.9 | 12.2 |
| Ethylcellulose N50 | 6.5 | 2.0 |
| Mag Stearate | 2.6 | 0.8 |
| DBS | 0.7 | 0.2 |
| Talc | 16.7 | 5.1 |
| Subtotal | 66.4 | 20.3 |
| Naltrexone cores | | |
| Sealed sugar spheres | (66.4) | (20.3) |
| Naltrexone HCl | 2.4 | 0.73 |
| HPC (Klucel LF) | 0.5 | 0.1 |
| Ascorbic acid | 0.2 | 0.1 |
| Talc | 1.1 | 0.4 |
| Subtotal | 70.6 | 21.6 |
| Naltrexone pellets | | |
| Naltrexone cores | (70.6) | (21.6) |
| Eudragit RS PO | 53.0 | 16.2 |
| SLS | 1.8 | 0.6 |
| DBS | 5.3 | 1.6 |
| Talc | 53.0 | 16.2 |
| Subtotal | 183.7 | 56.2 |
| Naltrexone-morphine cores | | |
| Naltrexone pellets | (183.7) | (56.2) |
| Morphine sulfate | 60.1 | 18.4 |
| Sodium chloride | 12.5 | 3.8 |
| HPC (Klucel LF) | 6.2 | 1.9 |
| Subtotal | 262.4 | 80.2 |
| Naltrexone-morphine pellets | | |
| Naltrexone-morphine cores | (262.4) | (80.2) |
| Ethylcellulose N50 | 22.9 | 7.0 |
| PEG 6000 | 10.6 | 3.2 |
| Eudragit L100-55 | 5.0 | 1.5 |
| DEP | 4.7 | 1.5 |
| Talc | 21.5 | 6.6 |
| Total | 327.1 | 100.0 |

B. Method of Preparation—
1. Dissolve Ethylcellulose and dibutyl sebacate into ethanol, then disperse talc and magnesium stearate into the solution.
2. Spray the dispersion from 1 onto sugar spheres in a Wurster to form seal-coated sugar spheres (50 μm seal coat).
3. Dissolve Klucel LF and ascorbic acid into 20:80 mixture of water and ethanol. Disperse naltrexone HCl and talc into the solution.
4. Spray the naltrexone dispersion from 3 onto seal-coated sugar spheres from 2 in a Wurster to form naltrexone cores.
5. Dissolve Eudragit RS, sodium lauryl sulfate and dibutyl sebacate into ethanol. Disperse talc into the solution.
6. Spray the dispersion from 5 onto naltrexone cores from 4 in a Wurster to form naltrexone pellets.
7. The Naltrexone pellets are dried at 50° C. for 48 hours.
8. Resulting pellets have a Eudragit RS coat thickness of 150 μm.
9. Dissolve sodium chloride and hypromellose into water.
10. Dissolve hypromellose into 10:90 mixture of water and ethanol. Disperse morphine sulfate into the solution.
11. Spray the solution from 9 followed by the dispersion from 10 onto naltrexone pellets in 7 in a rotor to form naltrexone-myrophine cores.
12. Dissolve ethylcellulose, PEG 6000, Eudragit L100-55 and diethyl phthalate into ethanol. Disperse talc into the solution.
13. Spray the dispersion from 12 onto naltrexone-morphine cores in 11 or 12 to form naltrexone-morphine pellets.
14. The pellets are filled into capsules.

B. In-vitro Drug Release—
1. Method—USP paddle method at 37° C. and 100 rpm 1 hour in 0.1N HCl, then 72 hours in 0.05M pH 7.5 phosphate buffer
Results—Percent of NT released at 73 hours for =0%
2. Method—USP paddle method at 37° C. and 100 rpm 72 hrs in 0.2% Triton X-100/0.2% sodium acetate/ 0.002N HCl, pH 5.5
Results—Percent of NT released at 73 hours=0%

C. In-Vivo Study

This is a single-dose, open-label, two period study in which eight subjects were randomized to receive one dose of PI-1510 under either fasted or fed state during Study Period 1 and alternate fasted or fed state for Study Period 2. Blood samples were drawn prior to dose administration and at 0.5 to 168 hours post-dose. Limits of quantitation are 4.00 pg/mL for naltrexone and 0.250 pg/mL for 6-beta-naltrexol. A summary of the pharmacokinetic measurements is provided in the following tables.

| | 6-beta-Naltrexol levels | |
|---|---|---|
| | PI-1510 | |
| | Fast | Fed |
| Tmax (hr) | 45.00 (N = 6) | 57.29 (N = 7) |
| Cmax (pg/mL) | 16.1 | 25.0 |
| $AUC_{last}$ (pg * h/mL) | 609.2 | 1057 |
| AUC∞ (pg * h/mL) | 1233 | 1431 (N = 6) |
| T½ (hr) | 17.36 | 17.48 (N = 6) |
| Relative Bioavailability to an oral solution (Dose-adjusted) | | |
| Cmax Ratio (Test/Solution) | 0.44% | 0.68% |
| $AUC_{last}$ Ratio (Test/Solution) | 1.97% | 3.42% |
| AUC∞ Ratio (Test/Solution) | 3.86% | 4.49% |

N = 8, unless specified otherwise

It was concluded that PI-1510 and PI-1495 are comparable. The reduction in naltrexone loading in the pellets (from 1.5% in PI-1495 to 0.7% in PI-1510) does not seem to affect NT release. Significant NT sequestering was observed, both at fasting (>96%) and fed states (>95%). The food effect observed was modest in terms of total NT release. However, the lag time was significantly reduced in the presence of food. There were subjects with multiple peaks of release.

Summary of NT Release from all In-Vivo Studies

BA (Cmax)=Relative bioavailability based on Cmax=Dose-adjusted ratio of Cmax (NT/KNT pellet) to Cmax (NT soln)
BA (AUC last)=Relative bioavailability based on AUC last=Dose-adjusted ratio of AUC last (NT/KNT pellet) to AU
BA (AUC inf)=Relative bioavailability based on AUC inf=Dose-adjusted ratio of AUC inf (NT/KNT pellet)
Total in-vivo cumulative NT release can be extrapolated from BA (AUC inf) calculations from 6-beta-Naltrexol plasma levels

|  | BA (Cmax) (%) | BA (AUC last) (%) | BA (AUC inf) (%) |
|---|---|---|---|
| OPTIM. #4 PI-1495 Fast | | | |
| Avg ± SD Range Fed | 0.5 ± 0.5 0.1-1.4 | 2.5 ± 2.3 5.9-0.3 | 2.6 ± 2.4 0.3-5.7 |
| Avg ± SD Range Fed (-Subject 1) | 3.0 ± 6.7 0.1-19.4 | 10.2 ± 19.4 0.2-57.0 | 11.3 ± 20.0 0.2-55.4 |
| Avg ± SD Range PI-1496 Fast | 0.6 ± 0.9 0.1-2.5 | 3.6 ± 4.9 0.2-13.8 | 4.0 ± 5.0 0.2-13.4 |
| Avg ± SD Range Fed | 1.2 ± 0.9 0.1-2.7 | 7.1 ± 4.6 0.6-14.2 | 7.0 ± 4.6 0.6-14.5 |
| Avg ± SD Range OPTIM. #5 PI-1510 Fast | 2.7 ± 2.9 0.1-7.6 | 13.4 ± 12.6 0.1-31.6 | 13.1 ± 12.3 0.4-30.7 |
| Avg Fed | 0.4 | 2.0 | 3.9 |
| Avg | 0.7 | 3.4 | 4.5 |

Example 3

| Kadian NT Formulation #6 (AL-01) | | |
|---|---|---|
|  | 15% TPCW | Final formulation AL-01 |
| Seal-coated Sugar Spheres | | |
| Sugar Spheres (#25-30 mesh) | 11.99 | 11.94 |
| Ethylcellulose NF 50 cps | 2.00 | 1.99 |
| Magnesium Stearate NF | 0.80 | 0.80 |
| Dibutyl Sebacate NF | 0.20 | 0.20 |
| Talc USP (Suzorite 1656) | 5.00 | 4.98 |
| Naltrexone HCl Core | | |
| Seal-coated Sugar Spheres | | (19.90) |
| Naltrexone Hydrochloride USP | 0.73 | 0.72 |
| Hydroxypropyl Cellulose NF | 0.14 | 0.14 |

| Kadian NT Formulation #6 (AL-01) | | |
|---|---|---|
|  | 15% TPCW | Final formulation AL-01 |
| Ascorbic Acid USP | 0.07 | 0.07 |
| Talc USP (Suzorite 1656) | 0.34 | 0.34 |
| Naltrexone HCl Intermediate Pellet | | |
| Naltrexone HCl Core | | (21.17) |
| Ammonio Methacrylate Copolymer Type B NF | 6.26 | 6.23 |
| Sodium Lauryl Sulfate NF | 0.22 | 0.22 |
| Dibutyl Sebacate NF | 0.63 | 0.62 |
| Talc USP (Suzorite 1656) | 6.08 | 6.05 |
| Naltrexone HCl Finished Pellet | | |
| Naltrexone HCl Intermediate Pellet | | (34.29) |
| Ammonio Methacrylate Copolymer Type B NF | 9.89 | 9.85 |
| Sodium Lauryl Sulfate NF | 0.34 | 0.34 |
| Dibutyl Sebacate NF | 0.99 | 0.98 |
| Talc USP (Suzorite 1656) | 9.71 | 9.67 |
| NaCl Overcoated Naltrexone HCl Pellet | | |
| Naltrexone HCl Finished Pellet | | (55.13) |
| Sodium Chloride USP | 3.75 | 3.73 |
| Hydroxypropyl Cellulose NF | 0.42 | 0.41 |
| MS Cores with Sequestered Naltrexone HCl | | |
| NaCl Overcoated Naltrexone HCl Pellet | | (59.28) |
| Morphine Sulfate USP | 18.11 | 18.03 |
| Hydroxypropyl Cellulose NF | 1.42 | 1.42 |
| MS Extended-release with Sequestered Naltrexone HCl Pellet | | |
| MS Cores with Sequestered Naltrexone HCl | | (78.73) |
| Component (a): ethylcellulose NF (50 cps) | 7.40 | 7.36 |
| Component (c): polyethylene glycol NF (6000) | 3.42 | 3.40 |
| Component (b): methacrylic acid copolymer NF (Type C, Powder) | 1.60 | 1.60 |
| Diethyl Phthalate NF (plasticizer) | 1.53 | 1.53 |
| Talc USP (Suzorite 1656) (filler) | 6.98 | 7.38 |
| Total | 100.0 | 100.0 |

In certain embodiments, components (a), (b) and/or (c) may be included as described below:
(a) preferably a matrix polymer insoluble at pH of about 1 to about 7.5; preferably ethylcellulose; preferably at least 35% by weight of a+b+c;
(b) preferably an enteric polymer insoluble at pH of about 1 to about 4 but soluble at pH of about 6 to about 7.5; preferably methacrylic acid-ethyl acrylate copolymer (methacrylic acid copolymer type C) preferably about 1 to about 30% of a+b+c; and,
(c) compound soluble at a pH from about 1 to about 4; preferably polyethylene glycol with a molecular weight from about 1700 to about 20,000; preferably from about 1% to about 60% by weight of a+b+c.

C. Method of Preparation
1. Ethylcellulose and Dibutyl Sebacate were dissolved into Alcohol SDA3A. Talc and Magnesium Stearate were then dispersed into the solution. The percent solid of the dispersion was 20%.
2. The dispersion from 1 was sprayed onto Sugar Spheres in a Wurster to form Seal-coated Sugar Spheres (approx. 50 μm seal coat).
3. Hydroxypropyl Cellulose and Ascorbic Acid were dissolved into a 20:80 mixture of Water and Alcohol SDA3A. Naltrexone HCl and Talc were then dispersed into the solution. The percent solid of the dispersion is 20.4%.
4. The Naltrexone HCl dispersion from 3 was sprayed onto Seal-coated Sugar Spheres from 2 in a Wurster to form Naltrexone HCl cores.

5. Ammonio Methacrylate Copolymer, Sodium Lauryl Sulfate and Dibutyl Sebacate were dissolved into a 22:78 mixture of Water and Alcohol SDA3A. Talc was dispersed into the solution. The percent solid of the dispersion was 20%.
6. The dispersion from 5 was sprayed onto Naltrexone HCl cores from 4 in a Wurster to form Naltrexone HCl Intermediate Pellets.
7. The Naltrexone HCl Intermediate Pellets were dried in an oven at 50° C. for 24 hours.
8. Ammonio Methacrylate Copolymer, Sodium Lauryl Sulfate and Dibutyl Sebacate were dissolved into a 22:78 mixture of Water and Alcohol SDA3A. Talc was dispersed into the Solution. The percent solid of the dispersion was 20%.
9. The dispersion from 8 was sprayed onto Naltrexone HCl Intermediate Pellets from 7 in a Wurster to form Naltrexone HCl Finished Pellets.
10. The Naltrexone HCl Finished Pellets were dried in an oven at 50° C. for 24 hours.
11. The resulting pellets had a pellet coat thickness of approximately 150 μm.
12. Sodium Chloride (NaCl) and Hydroxypropyl Cellulose were dissolved into Water. The percent solid in the solution was 6%.
13. The Sodium Chloride solution from 12 was sprayed onto Naltrexone HCl Finished Pellets from 10 in a Wurster to form Sodium Chloride (NaCl) Overcoated Naltrexone HCl Pellets.
14. Hydroxypropyl Cellulose was dissolved into Alcohol SDA3A, and Morphine Sulfate dispersed into the solution. The percent solid in the dispersion was 24.4%.
15. The Morphine Sulfate dispersion from 14 was sprayed onto NaCl Overcoated Naltrexone HCl Pellets in 13 in a rotor to form Morphine Sulfate Cores with Sequestered Naltrexone HCl.
16. Ethylcellulose, Polyethylene Glycol, Methacrylic Acid Copolymer and Diethyl Phthalate were dissolved into Alcohol SDA3A. Talc was dispersed into the solution. The percent solid in the dispersion was 14.3%.
17. The Dispersion from 16 was sprayed onto Morphine Sulfate Cores with Sequestered Naltrexone HCl in 15 to form Morphine Sulfate Extended-release with Sequestered Naltrexone HCl Pellets.
18. The pellets were filled into capsules.

Example 4

Methods for Treating Pain (202)

As an example, Kadian NT (60 mg morphine sulfate, 2.4 mg naltrexone HCl) was administered to humans and compared to the previously described product Kadian. Each Kadian sustained release capsule contains either 20, 30, 50, 60, or 100 mg of Morphine Sulfate USP and the following inactive ingredients common to all strengths: hydroxypropyl methylcellulose, ethylcellulose, methacrylic acid copolymer, polyethylene glycol, diethyl phthalate, talc, corn starch, and sucrose. In these studies, the effects of Kadian were compared to those of Kadian NT.

Patients already being treated with Kadian were subjected to a "washout" period of approximately 14 days during which Kadian was not administered. Immediately following this washout period, the trial was begun. Patients were either administered Kadian or Kadian NT at day 0. After a period of up to 28 days treatment with Kadian®, patients were then "crossed-over" to Kadian NT or continued taking Kadian®. The amount of Kadian NT was individually adjusted such that each patient was receiving approximately the same amount of morphine they had previously been receiving while taking Kadian. This cross-over was then repeated after 14 days. Various physiological responses were measured at different timepoints, as discussed below. These responses included morphine blood levels, naltrexone blood levels, 6-β-natrexol blood levels and pain scores.

Mean morphine concentrations were measured and determined to be approximately the same for Kadian® and Kadian NT. This observation confirms that the new formulation effectively releases morphine into the blood of patients. This is shown in the table below:

|  | Cmax (pg/mL) | Cmin (pg/mL) | Cavg (pg/mL) | Tmax (hr) | Fluctuation (%) | AUC (TAU) (hr* pg/mL) |
|---|---|---|---|---|---|---|
| Kadian | | | | | | |
| N | 68 | 68 | 68 | 68 | 68 | 68 |
| Mean | 12,443 | 6,650 | 9,317 | 4.90 | 66.3 | 111,806 |
| SD | 7,680 | 4,544 | 6,019 | 3.36 | 28.8 | 72,223 |
| Min | 2,630 | 1,000 | 1,758 | 0.00 | 21.4 | 21,100 |
| Median | 9,870 | 5,285 | 7,426 | 5.00 | 63.5 | 89,110 |
| Max | 35,600 | 21,600 | 28,908 | 12.0 | 213 | 346,900 |
| CV % | 61.7 | 68.3 | 64.6 | 68.5 | 43.4 | 64.6 |
| Kadian NT | | | | | | |
| N | 68 | 68 | 68 | 68 | 68 | 68 |
| Mean | 13,997 | 6,869 | 10,120 | 4.29 | 71.49 | 121,438 |
| SD | 10,949 | 5,377 | 7,316 | 3.05 | 38.59 | 87,794 |
| Min | 2,420 | 0.00 | 1,815 | 0.00 | 21.04 | 21,775 |
| Median | 10,200 | 5,805 | 7,496 | 4.00 | 65.89 | 89,948 |
| Max | 57,600 | 29,000 | 35,046 | 12.0 | 265 | 420,550 |
| CV % | 78.2 | 78.3 | 72.3 | 71.0 | 54.0 | 72.3 |

It is important that the Kadian NT formulation not release significant amounts of antagonist (i.e., naltrexone or derivatives thereof) into the bloodstream such that the activity of morphine is diminished. Only 14 of 69 patients had quantifiable (>4.0 pg/mL) naltrexone concentrations. The range of quantifiable concentrations was 4.4-25.5 pg/mL. However, the release of some naltrexone into the bloodstream did not significantly affect the pain scores (see below).

| Subject | Naltrexone Conc (pg/mL) | Pain Score* |
|---|---|---|
| 49411 | 25.5 | 2 |
| 49408 | 16.8 | 3 |
| 59510 | 15.9 | 2 |
| 29218 | 13.5 | 0 |
| 39308 | 7.74 | 0 |
| 39306 | 8.98 | 1 |
| 49422 | 8.12 | 4 |
| 79709 | 7.15 | 2 |
| 89817 | 6.82 | 3 |
| 59509 | 6.29 | 2 |
| 49409 | 6.58 | 2 |
| 49431 | 4.81 | 1 |
| 49430 | 4.58 | 1 |
| 59530 | 4.4 | 3 |

*A pain score of 0-3 is considered "mild" and 4-7 is considered "moderate".

When provided in an immediate formulation, naltrexone (parent) is rapidly absorbed and converted to the 6-β-naltrexol metabolite. 6-β-naltrexol is a weaker opioid antagonist than naltrexone, having only 2 to 4% the antagonist potency.

Most patients had quantifiable levels (>0.25 pg/mL) of 6-β-naltrexol. The incidental presence of 6-β-naltrexol in the plasma had no effect on pain scores.

It was also important to confirm that Kadian NT did not result in a significantly different type, number or severity of common adverse events. This was confirmed, as shown below:

| | Open-label | Double-blind | |
|---|---|---|---|
| Event | Kadian (N = 111) | Kadian (N = 71) | Kadian NT (N = 71) |
| Any event | 83.8% | 45.1% | 46.5% |
| Constipation | 46.8% | 12.7% | 15.5% |
| Nausea | 40.5% | 8.5% | 9.9% |
| Somnolence | 28.8% | 8.5% | 9.9% |
| Vomiting | 24.3% | 4.2% | 8.5% |
| Dizziness | 20.7% | 7.0% | 1.4% |
| Headache | 16.2% | 8.5% | 4.2% |

In addition, it was important to note whether Kadian NT functioned similarly to Kadian with respect to adverse events typically associated with withdrawal symptoms. This was confirmed as shown below:

| | Open-label | Double-blind | |
|---|---|---|---|
| Event | Kadian (N = 111) | Kadian (N = 71) | Kadian NT (N = 71) |
| Tremor | 3.6% | 0.0% | 0.0% |
| Anxiety | 2.7% | 2.8% | 1.4% |
| Irritability | 1.8% | 0.0% | 0.0% |
| Restlessness | 0.9% | 0.0% | 0.0% |
| Muscle Twitch | 0.9% | 0.0% | 0.0% |
| Cold Sweat | 0.9% | 0.0% | 1.4% |
| Piloerection | 0.0% | 0.0% | 0.0% |
| Rhinitis | 0.0% | 0.0% | 0.0% |
| Tachycardia | 0.0% | 0.0% | 0.0% |

Other measurements, including In-Clinic Pain, WOMAC Pain, WOMAC Stiffness, WOMAC Daily Activities, and BPI Pain were also made. It was determined that the differences in these measurements in those taking Kadian and those taking Kadian NT was not significant, as shown below.

| In-Clinic Pain (ITT Population, Completers) | | | | |
|---|---|---|---|---|
| | Mean | | | |
| Day | Kadian | Kadian NT | Treatment P-value | 95% CI for Difference |
| Baseline | 2.13 | | | |
| Change Day 7 | N = 68 +0.18 | N = 69 +0.16 | 0.9773 | −0.32, 0.33 |
| Change Day 14 | N = 69 +0.28 | N = 69 +0.06 | 0.2176 | −0.13, 0.56 |

| WOMAC Pain (ITT Population, Completers) | | | | |
|---|---|---|---|---|
| | Mean | | | |
| Day | Kadian | Kadian NT | Treatment P-value | 95% CI for Difference |
| Baseline | 98.1 | | | |
| Change Day 14 | N = 69 +18.1 | N = 69 +5.9 | 0.0928 | −2.0, 26.0 |

| WOMAC Stiffness (ITT Population, Completers) | | | | |
|---|---|---|---|---|
| | Mean | | | |
| Day | Kadian | Kadian NT | Treatment P-value | 95% CI for Difference |
| Baseline | 51.1 | | | |
| Change Day 14 | N = 69 +12.3 | N = 69 +2.1 | 0.0200 | 1.7, 18.5 |

| WOMAC Daily Activities (ITT Population, Completers) | | | | |
|---|---|---|---|---|
| | Mean | | | |
| Day | Kadian | Kadian NT | Treatment P-value | 95% CI for Difference |
| Baseline | 396.6 | | | |
| Change Day 14 | N = 69 +70.7 | N = 69 +28.9 | 0.1206 | −11.0, 93.6 |

In conclusion, plasma morphine levels for Kadian and Kadian NT are bioequivalent. It was observed that 55 of 69 (80%) patients had no measurable levels of naltrexone. Of the 14 patients with measurable levels of naltrexone, there was no negative effect on pain scores. Seven of these 14 patients had a measurable level at only one time point. Most patients had some level of 6-β-naltrexol, however there was no negative effect on pain scores. In addition, there was no difference in pain scores in individuals taking Kadian or Kadian NT.

Example 5

Long-Term Safety, Study of Kadian NT (302)

A. Methods

The primary objective of this study was to evaluate the long-term safety of Kadian NT administered for up to 12 months. The secondary objectives of this study were to:
  evaluate the long-term efficacy of Kadian NT during a 12-month period by assessing pain intensity (PI) in the past 24 hours using the Brief Pain Inventory (BPI) Short Form, and the Global Assessment of Study Drug;
  evaluate opioid withdrawal symptoms in subjects who receive Kadian NT upon completion of 12-months exposure or early termination from the study using the Clinical Opiate Withdrawal Scale (COWS); and,
  evaluate plasma naltrexone, 6-β-naltrexol, and morphine concentrations at Visits 2 through 15 in selected male and female subjects for pharmacokinetic study This long-term, open-label study evaluated the safety of Kadian NT administered once or twice daily (QD or BID) over a 12-month period. Kadian NT was used in dosage strengths of 20 mg, 30 mg, 40 mg, 50 mg, 60 mg, 80 mg and 100 mg. There was no maximum allowable daily dose set for this study. Subjects were titrated upward as needed in a manner consistent with the current Kadian® labeling and in accordance with the investigator's best medical judgment for the most effective pain management. Multiples of the available dosage strengths were combined as needed to achieve the intended necessary daily dose.

Subjects with chronic moderate to severe nonmalignant pain who meet all inclusion/exclusion criteria were enrolled into the long-term study. Each subject was provided with Kadian NT at each clinic visit in the form of capsules to be-administered BID approximately 12 hours apart or QD at 24-hour intervals. Opioid-naïve subjects began at a total daily dose of 40 mg Kadian NT administered as 20 mg BID. Opioid-naïve subjects who fully qualify for study and have documented normal labs within the previous three months were enrolled and dosed on the Baseline Visit day. All other subjects were to return within seven days for enrollment and dosing.

Subjects currently taking opioids who will have their opioid dose converted to a Kadian NT dose should be scheduled for a morning clinic appointment (before noon) for the Drug Dispensing Visit. Additionally, subjects were instructed to refrain from taking the morning dose of their current opioid pain medication on the day of their Drug Dispensing clinic visit. It was recommended that subjects who are already taking opioid medication be started oil a Kadian NT dose equivalent to 50% to 75% of the current daily opioid dose rounded to the lowest available Kadian NT dosage strength due to potential for incomplete cross tolerance. The dose was determined utilizing the conversion table provided in Appendix V of this protocol; investigators were free to choose an alternate opioid conversion schedule at their own discretion. Opioid dose requirements were based on the subject's average combined daily opioid consumption for chronic and rescue dosing over the week prior to study entry.

All subjects were to return to the clinic one week after the Drug Dispensing Visit and then monthly for the remainder of the study. Pain Intensity and Global Assessment of Study Drug were collected at each scheduled visit. Urine drug screens, adverse events (AEs), concomitant medications, and vital signs were collected at all clinic visits. Urine pregnancy tests will be performed monthly on females of child-bearing potential. Drug accountability was conducted at all clinic visits. The occurrence of withdrawal symptoms for subjects taking Kadian NT was assessed utilizing the Clinical Opiate Withdrawal Scale (COWS). The COWS was administered at every visit from Visit 3 through 16, or at early termination (whichever comes first).

Dose titration was allowed throughout the duration of the study. At each clinic visit, the dose of Kadian NT was increased where all of the following criteria were met:

Subject was tolerating study medication (no unacceptable AEs);

Pain Intensity (PI) within the past 24 hours is >3; and,

Both investigator and subject agreed that the dose should be increased.

Even if a subject is experiencing a PI>3, the subject was free to choose not to have the dose increased. For example, a subject may have been satisfied with having his or her pain level reduced to a PI level of 4. If a subject's dose was increased and the subject reported unacceptable AEs or an opioid-experienced subject was converted to a dose that results in unacceptable AEs, the dose was decreased.

If a subject experiences inadequate pain relief and desired to have his or her dose increased prior to a scheduled clinic visit, the subject was allowed to telephone the site and request a dose increase after a minimum of three days at the previous dosage level. The subject was then to return to the site for an unscheduled clinic visit to return study medication and to receive new study medication at the increased dose. Opioid toxicity assessments and drug accountability were conducted, but a complete battery of efficacy assessments was not necessary for these unscheduled visits.

Investigators provided a stimulating bowel regimen for prophylactic treatment of constipation, the most common opioid side effect. (American Pain Society, 2003) If unacceptable opioid-related AEs were experienced prior to a scheduled clinic visit, subjects were allowed to return to the clinic between scheduled visits for a dose reduction and to obtain treatment for opioid-related AEs.

Subjects were required to return for a post-treatment follow-up visit approximately 28 to 32 days after the final dose of study medication to record AEs and concomitant medications and to assure that appropriate tapering from study medication and transition to standard of care has been accomplished. Subjects wishing to discontinue opioid medication were converted to Kadian® for the taper period. The suggested mechanism for tapering was for the subject to take half of his or her last effective dose of study medication in divided doses of Kadian (BID) for three days, and then to take half of that reduced dose in divided doses (BID) for the next three days; on the seventh day, all dosing will discontinue. Subjects were also allowed to convert to currently-approved extended release opioid per investigator discretion.

Safety was evaluated by vital signs (heart rate, respiratory rate, blood pressure after sitting for three minutes, and oral temperature), physical examinations, electrocardiograms (ECGs), clinical laboratory tests and Adverse Events. Clinical laboratory tests were performed at Baseline and at the end of months 3, 6, 9, and 12 or at early termination. Qualitative urine drug screens were performed monthly and included reflex testing to identify specific opiates taken by subjects during study participation. Urine pregnancy tests were performed monthly for female subjects of child-bearing potential. ECG was performed at Baseline, at the end of months 6 and 12 or early termination.

Population pharmacokinetic (PK) sampling was also performed in this study monthly after the Baseline Visit. The Interactive Voice Response System (IVRS) was used to identify up to 20 subjects in each of the following daily dosing categories to undergo PK sample collection at their scheduled visits: 40 mg to 60 mg, 80 mg to 120 mg, and >120 mg. Up to 20 subjects aged 65 years and above were also identified to participate in the PK sample collection. The primary focus of this PK sampling was to quantify naltrexone, 6-beta naltrexol and morphine concentrations. Study medications were in the form of orally administered capsules. Study medications were: 1) Kadian NT 20, 30, 40, 50, 60, 80 and 100 mg capsules; or, 2) acetaminophen up to two (2) grams per day (500 mg every 6 hours as needed) as rescue medication.

A subject was eligible for study participation if he/she meets the following criteria:

1. The subject was 18 to 70 years of age and exhibited sufficient literary skills to complete study assessments.
2. The subject agreed to refrain from taking any opioid medications other than study medication during the study period, and agreed to report all non-opioid analgesic medications taken;
3. Subject had a history of chronic moderate to severe pain caused by a nonmalignant condition for at least three months prior to Baseline Visit. Conditions may include, but are not limited to, osteoarthritis of any joint, chronic low back pain with or without radiculopathy, diabetic peripheral neuropathy, and post-herpetic neuralgia. Subject was directed to choose the most painful joint or body area to serve as the target joint/area for this study. A target joint was not to contain any type of orthopedic and/or prosthetic device.
4. If female, subject was either not of childbearing potential (defined as postmenopausal for at least one year or surgically sterile (bilateral tubal ligation, bilateral oophorectomy or hysterectomy)) childbearing potential and practicing one of the following methods of birth control:
   total abstinence from sexual intercourse (minimum one complete menstrual cycle before study entry),
   a vasectomized partner,
   contraceptives (oral, parenteral, or transdermal) for three consecutive months prior to investigational product administration,
   intrauterine device (IUD), or
   double-barrier method (condoms, sponge, diaphragm or vaginal ring with jellies or cream).
5. If female of childbearing potential, subject had a negative urine pregnancy test at screening (urine specimen must be obtained within 14 days prior to randomization) and monthly throughout study participation.
6. Subject was able to understand and cooperate with study procedures, was to be easily reached by telephone, and signed a written informed consent prior to entering the study.

A subject will be excluded from the study if he/she meets any of the following criteria:
1. Subject had a documented history of an allergic reaction (hives, rash, etc.) or a clinically significant intolerance to morphine or other opioids, such that treatment with morphine is contraindicated.
2. Subject was pregnant or breast-feeding.
3. Subject was receiving systemic chemotherapy, or has an active malignancy of any type, or has been diagnosed with cancer within the past three years (excluding squamous or basal cell carcinoma of the skin).
4. Subject had a documented history of drug abuse/dependence/misuse or narcotic analgesic abuse/dependence/misuse within five years prior to the Baseline Visit.
5. Subject had a documented history of alcohol abuse (>2 glasses/day) and/or dependence within five years prior to the Baseline Visit, which, in the opinion of the investigator, may have influenced subject compliance with the study.
6. Subject had a positive urine drug screen at the Baseline Visit NOT caused by any therapeutic concomitant medication reported by the subject.
7. Subject was considered by the investigator, for any reason, to be an unsuitable candidate to receive extended-release morphine sulfate with naltrexone, including (but not limited to) the risk(s) in terms of precautions, warnings, and contraindications in the Investigator's Brochure for Kadian NT.
8. Subject had a Body Mass Index (BMI)>4.5 kg/m$^2$.
9. Subject had a psychiatric illness or medical illness/condition, and/or abnormal diagnostic finding, that, in the opinion of the investigator, would interfere with the completion of the study, confound the results of the study, or pose risk to the subject.
10. Subject had abnormalities on physical examination, or abnormal vital signs or ECG findings that judged to be clinically significant by the investigator.
11. Subject had clinically significant abnormalities in clinical chemistry, hematology or urinalysis, including serum glutamic-oxaloacetic transaminase/aspartate aminotransferase (AST) or serum glutamic-pyruvic transaminase/alanine aminotransferase (ALT) ≥3.0 times the tipper limit of the reference range or a serum creatinine≥3.0 mg/dL at the Baseline Visit.
12. Subject had pain in the target area due to conditions such as malignancy, fibromyalgia, migraine, recent trauma or fracture, or infection.
13. Subject was involved in an unsettled claim such as automobile accident, civil lawsuit, or worker's compensation pertaining to a specific injury. Subjects with settled claims were allowed to participate.
14. Subject received intraspinal infusion of any medication within one month of the Baseline Visit, had an implanted spinal cord stimulator, or had plans for such treatment during the proposed study period.
15. Subject received epidural or local corticosteroid injections in target joint within two months of the Baseline Visit, or target joint viscosupplementation within the past three months.
16. Subject received oral or intramuscular corticosteroids within the past 90 days. (Topical, nasal and inhaled corticosteroids were permitted and low, stable doses e.g. <10 mL, prednisone, provided were no changes in dosing within the previous four weeks.)
17. Subject had surgical intervention to the back within six months of study entry or plans for surgical intervention while in the study.
18. Subject underwent an elective surgical procedure within eight weeks prior to the Baseline Visit, or was scheduled for an elective surgical procedure during the course of the study.
19. Subject had a history of severe impairment of pulmonary function, hypercarbia, hypoxia, chronic obstructive pulmonary disease, cor pulmonale, uncontrolled asthma, sleep apnea syndrome, or respiratory depression.
20. Subject had a history of gastric or small intestine surgery leading to clinical malabsorption (e.g., gastric bypass), or any other disease that causes clinical malabsorption.
21. Subject had active cardiac disease or other health condition(s) that pose a significant health risk in the event of opioid withdrawal.
22. Subject was taking phenothiazines or high doses of sedatives, hypnotic, or tranquilizers. Chronic low dose sleep aids or anxiolytics were allowed with Medical Monitor approval.
23. Subject was historically non-responsive (no therapeutic response) to morphine.
24. Subject had received treatment with an investigational product in the 30 days prior to Baseline Visit.

Safety endpoints were the incidence of treatment-emergent AEs; changes from pre-treatment to post-treatment for vital signs, ECGs, physical examination findings, and clinical laboratory test results; and opioid toxicity assessments. The efficacy endpoints were Pain Intensity (PI) within the past 24 hours; and, Global Assessment of Study Drug.

Three subject analysis populations were defined as follows: 1) the "safety population" consisting of all subjects who take study medication, used for safety analyses; 2) the "intent-to-treat" (ITT) population consisting of all subjects who take study medication and have at least one post-Baseline Brief Pain Inventory, or Global Assessment of Study Drug observation; the ITT population will be used for efficacy analyses; 3) the pharmacokinetic (PK) population will consist of all subjects with PK samples and will be used for PK analyses.

Safety was assessed based on the incidence of treatment-emergent AEs, chances from pre-treatment to post-treatment for vital signs, ECGs, physical examination findings and clinical laboratory test results. Changes on a Physical Exam were captured as Adverse Events.

The number and percentage of subjects with AEs will be displayed by System Organ Class and preferred term using the Medical Dictionary for Regulatory Activities® (MedDRA®). Summaries in terms of severity and relationship to study medication were also provided. SAEs and AEs causing discontinuation of study medication were summarized separately in a similar manner. Subject listings of AEs causing discontinuation of study medication and SAEs was produced. The incidence and severity of selected opioid-associated AEs, including dry mouth, constipation, dizziness, somnolence, pruritus, nausea, and vomiting were also be tabulated. Vital signs were summarized at each visit in terms of descriptive statistics including the mean, median, standard deviation, minimum, maximum, and quartiles. Actual values and change from Baseline were summarized. ECGs were performed at Baseline, Visit 8 (end of month 6) and Visit 15 (end of month 12) or Early Termination. Changes from Baseline were summarized. Quantitative laboratory test results were summarized at each visit in terms of descriptive statistics. Actual values and change from Baseline were summarized. For qualitative laboratory tests, the number and percentage of subjects in each category were produced at each visit. For all laboratory tests, a shift table was produced summarizing changes from normal (at Baseline) to abnormal and vice-versa. The number and percentage of subjects with normal and abnormal findings in the physical examination at each visit were displayed. A shift table was produced summarizing changes from normal (at Baseline) to abnormal and vice-versa. COWS were summarized at each visit beginning with Visit 3 in terms of descriptive statistics. Actual values and change through study period were summarized. Selected analyses were repeated by subgroups based on age, sex, and race.

Efficacy was assessed based on the BPI Short Form, and subject's Global Assessment of Study Drug. All efficacy analyses were descriptive, with no formal testing of statistical hypotheses, although p-values or confidence intervals were presented to aid in interpretation. Each of the four items of the BPI Short Form were analyzed at each visit in terms of the values themselves as well as in terms of change and percent change from Baseline. Descriptive statistics were calculated, and pairwise t-test p-values used to summarize the difference between each post-Baseline time point and Baseline. Global Assessment of Study Drug was summarized descriptively. Rescue medication (additional analgesic medication) was summarized. All efficacy analyses are considered secondary. Sparse blood samples (one trough blood sample taken from each subject participating in the PK study, total 14 blood samples) were taken at selected visits for morphine, naltrexone, and 6-β-naltrexol determinations.

Schedule of Observations and Procedures

| Evaluation | Visit 1 Baseline Day −7 to Day 0 | Drug Dispensing Visit Day 0 | Visits 2-3 End of Wks 1 & 4 (+/−2 days) | Unscheduled Visits[1,2] Dose Adjust/Tx of AEs | Visits 4-14 End of Mos 2-11 Wk 8-48 (+/−3 days) | Visit 15 End of Mo 12 (Wk 52)/Early Termination (+/−3 days) | Follow-up Telephone Call Opioid Withdrawal Monitoring (Days 1-4)[3] | Visit 16[4] Post Treatment Follow-up |
|---|---|---|---|---|---|---|---|---|
| Written Informed Consent | X | | | | | | | |
| Inclusion/Exclusion Criteria | X | | | | | | | |
| Vital Signs[5] | X | | X | X | X | X | | |
| Height, Weight, and BMI | X | | | | | | | |
| Complete Physical Exam | X | | | | X[6] | X | | |
| Chronic Pain History | X | | | | | | | |
| Medical History | X | | | | | | | |
| 12-lead ECG | X | | | | X[6] | X | | |
| Clinical Laboratory Tests[7] | X | | | | X[8] | X | | |
| PK sampling[9] | | | X | | X | X | | |
| Urine Drug Screen | X | | X[10] | X[10] | X[10] | X[10] | | |
| Urine Pregnancy Test for Females of Childbearing Potential | X | | X[11] | X | X | X | | |
| Clinical Pain Intensity | X | | X | X | X | X | | |
| Clinic Global Assessment of Study Drug | | | X | | X | X | | |
| Dispense Study Medication | | X | X | X | X | | | |
| Study/Rescue Drug Accountability | | | X | X | X | X | | |
| COWS | | | X | X | X | X | | X |
| Concomitant Medications | X | | X | X | X | X | X | X |
| Adverse Events | | | X | X | X | X | X | X |

BMI = Body Mass Index

[1] Assess subject's current pain intensity at unscheduled visits for inadequate pain relief (to enter in IWRS).

[2] A subject converting from another opioid to Kadian NT may return in ≥24 hours of the Drug Dispensing Visit for an unscheduled visit for a dose increment if the initial dose conversion leads to inadequate pain relief. In addition, if a subject who converted from another opioid experiences symptoms of opioid withdrawal after dose conversion, Alpharma/INC Research may be contacted for approval to allow the subject to return in <24 hours of the Baseline Visit for a dose increase, if necessary. All other visits for dose increases may only occur if a subject has been on current dose for ≥3 days.

[3] Subjects to be converted to approved ER opioid or tapered per investigator discretion. If necessary, a clinic visit may be required for those subjects experiencing clinically significant symptoms of opioid withdrawal.

[4] Visit 16 may be conducted 28 to 32 days after the last dose of study medication.

[5] Vital signs include heart rate, respiratory rate, blood pressure after sitting for three minutes, and oral temperature.

[6] Completed at Visit 8 (Month 6) only.

[7] Includes chemistry, hematology, and urinalysis.

[8] Completed at Visits 5, 8, and 11 (End or Months 3, 6 and 9) only.

[9] To be completed on subjects in the PK population only.

[10] Includes reflex testing to identify specific opiates used.

[11] Completed at Visit 3 only

B. Results

1. Adverse Events

Treatment-Emergent AEs (TEAEs) occurring in more than 5% of patients included constipation, nausea, vomiting, headache, somnolence, diarrhea, pruritis and fatigue. These are all typical opioid-related AEs. A summary of the number of Treatment-Emergent Adverse Events, Serious Adverse Events and Deaths (none) resulting from treatment with Kadian NT is shown below.

TEAEs resulting in discontinuation of treatment was observed in approximately 30% of patients administered less than 80 mg Kadian NT per day; approximately 10% of patients administered between 80 and 120 mg Kadian NT per day; and, approximately 9% of patients administered more than 120 mg Kadian NT per day. Overall, TE AEs were observed in approximately 24% of patients.

Serious AEs (SEAEs) resulting in discontinuation of Kadian NT treatment were observed in approximately 2% of patients administered less than 80 mg Kadian NT per day; approximately 8% of patients administered between 80 and 120 mg, Kadian NT per day; and, approximately 2% of patients administered more than 120 mg Kadian NT per day. Overall, SE AEs were observed in approximately 3% of patients.

Summary of Treatment-Emergent Adverse Events, Serious Adverse Events and Death - Safety Population

|  | Average Daily Dose of Kadian NT | | | |
|---|---|---|---|---|
|  | <80 mg N = 307 | 80-120 mg N = 67 | >120 mg N = 56 | Overall N = 439 |
| Any Treatment-Emergent Adverse Event | 246 (80.1%) | 56 (83.6%) | 37 (66.1%) | 340 (77.4%) |
| Treatment-Emergent Adverse Events which are Possibly, Probably, or Definitely related to Kadian NT | 210 (68.4%) | 31 (46.3%) | 22 (39.3%) | 264 (60.1%) |
| Treatment-Emergent Adverse Events which led to discontinuation of Kadian NT | 92 (30.0%) | 7 (10.4%) | 5 (8.9%) | 105 (23.9%) |
| Severe Treatment-Emergent Adverse Events | 39 (12.7%) | 11 (16.4%) | 6 (10.7%) | 56 (12.8%) |
| Serious Adverse Events | 11 (3.6%) | 6 (9.0%) | 2 (3.6%) | 19 (4.3%) |
| Serious Adverse Events which led to discontinuation of Kadian NT | 6 (2.0%) | 5 (7.5%) | 1 (1.8%) | 12 (2.7%) |
| Deaths | 0 | 0 | 0 | 0 |

2. Efficacy

As shown in FIGS. 1-4, daily administration of Kadian NT to patients included in this trial results in lower mean BPI scores for up to six months. The data indicates that the affects of morphine in this population is not negatively affected by the concomitant administration of both morphine and naltrexone in an intact dosage font (Kadian NT). Thus, Kadian NT may be used to effectively treat pain in human patients for long periods of time (i.e., greater than two weeks). Previously, Kadian NT was only shown to be effective for periods up to two weeks. It was not known whether the cumulative effect of repeatedly administering a composition containing a morphine antagonist over a period of greater than two weeks would eventually negatively affect the actions of morphine in the patient. Surprisingly, the data indicates that Kadian NT may be used to alleviate pain for long periods of time (i.e., greater than two weeks). The data also indicates that Kadian NT may be most effective at the lowest dose tested (i.e., less than 80 mg per day).

Pharmacokinetic (PK) data was also analyzed as shown below. The results demonstrate that naltrexone was indeed sequestered over the course of the trial. While there were a couple of outliers, the data indicates sequestration is possible over long periods of time (i.e., greater than two weeks and out to 100 weeks).

ALO-KNT-302 PK Data

| Week | Subject | Morphine Conc (ng/mL) | Naltrexone Conc (pg/mL) | 6B-Naltrexol Conc (pg/mL) |
|---|---|---|---|---|
| 1 | 201-2005 | 4.16 | 0 | 0 |
|  | 201-2006 | 3.28 | Missing | Missing |
|  | 201-2013 | 2 | 0 | 3.24 |
|  | 202-2001 | LIS | Missing | Missing |
|  | 203-2004 | 0 | 0 | 0 |
|  | 204-2003 | 4.04 | 0 | 10.3 |

-continued

ALO-KNT-302 PK Data

| Week | Subject | Morphine Conc (ng/mL) | Naltrexone Conc (pg/mL) | 6B-Naltrexol Conc (pg/mL) |
|---|---|---|---|---|
|  | 204-2006 | 5.11 | 0 | BLQ < 10.0 |
|  | 204-2008 | 9.27 | 0 | 26.3 |
|  | 205-2001 | 5.18 | 0 | 0 |
|  | 205-2002 | 18.9 | 0 | 3.31 |
|  | 205-2007 | 4.17 | 4.33 | 63.3 |
|  | 209-2012 | 3.28 | 0 | Missing |
|  | 211-2001 | 3.95 | 0 | BLQ < 1.00 |
|  | 211-2003 | 2.98 | 0 | ALQ < 10.0 |

ALO-KNT-302 PK Data

| Week | Subject | Morphine Conc (ng/mL) | Naltrexone Conc (pg/mL) | 6B-Naltrexol Conc (pg/mL) |
|---|---|---|---|---|
| | 211-2005 | 7.43 | 0 | 146 |
| | 212-2001 | 4.23 | 0 | BLQ < 1.00 |
| | 212-2002 | 5.31 | 0 | 10.3 |
| | 212-2005 | Missing | 0 | 58.4 |
| | 212-2006 | 3.7 | 4.68 | 12.8 |
| | 213-2002 | 0 | 0 | 21.9 |
| | 213-2003 | 3.86 | 4.03 | 43.7 |
| | 213-2004 | 36.2 | 0 | 69.5 |
| | 213-2005 | 2.45 | 0 | BLQ < 5.00 |
| | 213-2007 | 7.35 | 0 | BLQ < 2.50 |
| | 214-2002 | 5.77 | 0 | 33.2 |
| | 217-2010 | 4.23 | 0 | 13.4 |
| | 217-2014 | 35.3 | 0 | 280 |
| | 222-2001 | 1.99 | 0 | 25.3 |
| | 222-2002 | 2.81 | 0 | 0.532 |
| | 222-2003 | 2.66 | 0 | Missing |
| | 222-2008 | 24.4 | 0 | 13.4 |
| | 222-2009 | 4.01 | 0 | 4.31 |
| | 222-2016 | 6.1 | 0 | 2.04 |
| | 229-2005 | 9.12 | 0 | 1.1 |
| | 229-2006 | 5.94 | 0 | 36.7 |
| | 229-2008 | 4.32 | 0 | 9.86 |
| | 235-2001 | 5.85 | 0 | 14.5 |
| | 235-2008 | 6.01 | 0 | 0 |
| | 239-2002 | 1.76 | 0 | Missing |
| | 240-2003 | 22.7 | 0 | 9.33 |
| | 241-2001 | 0 | 0 | 0 |
| | 241-2007 | 3.21 | 0 | BLQ < 2.50 |
| | 252-2001 | 24.9 | 0 | 128 |
| | 252-2002 | 5.04 | 0 | 0 |
| | 255-2001 | 0.608 | 0 | BLQ < 10.0 |
| | 255-2003 | 101 | 0 | 28.4 |
| | 257-2005 | 7.74 | 0 | 10 |
| | 257-2010 | 7.85 | 0 | 6.75 |
| | 257-2011 | 7.57 | 0 | 12.1 |
| | 259-2002 | 15.5 | 0 | 24.6 |
| | N | 48 | 48 | 37 |
| | Mean | 9.44 | 0.272 | 30.3 |
| | SD | 15.8 | 1.07 | 53.6 |
| | Min | 0 | 0 | 0 |
| | Median | 4.68 | 0 | 12.1 |
| | Max | 101 | 4.68 | 280 |
| | CV % | 167.7 | 392.2 | 176.6 |
| 4 | 201-2005 | 2.06 | 0 | 1.01 |
| | 201-2006 | 3.45 | 0 | 0 |
| | 201-2013 | 3.29 | 0 | 58.3 |
| | 204-2006 | PC | 0 | BLQ < 20.0 |
| | 204-2008 | 9.95 | 0 | 7.16 |
| | 205-2001 | 3.3 | 0 | 3.12 |
| | 205-2002 | 28.9 | 0 | 1.27 |
| | 205-2007 | 4.58 | 6.76 | 172 |
| | 209-2012 | 14.2 | 0 | Missing |
| | 212-2001 | 10.8 | 0 | 51.1 |
| | 212-2002 | 5.88 | 0 | Missing |
| | 212-2005 | Missing | 17.7 | 763 |
| | 212-2006 | 2.7 | 0 | Missing |
| | 213-2002 | 0 | 0 | 3.58 |
| | 213-2003 | 9.63 | 0 | 22.3 |
| | 213-2004 | Missing | 0 | 107 |
| | 213-2007 | 8.52 | 0 | BLQ < 1.00 |
| | 214-2010 | 4.28 | 0 | 1.26 |
| | 217-2014 | 24.2 | BLQ < 8.00 | 293 |
| | 222-2002 | 0.693 | 0 | 0 |
| | 222-2003 | 0 | 0 | 0 |
| | 222-2016 | 5.74 | 0 | 0 |
| | 229-2005 | 14.9 | 0 | 0.813 |
| | 229-2008 | 4.51 | 0 | 24.3 |
| | 229-2009 | 6.34 | 0 | 1.29 |
| | 235-2001 | 12.6 | 0 | 10.9 |
| | 241-2001 | 11.6 | 0 | 4.1 |
| | 241-2004 | 30.6 | 0 | 16.3 |
| | 241-2007 | 0 | 0 | BLQ < 0.500 |
| | 243-2005 | Missing | Missing | Missing |
| | 252-2001 | 21.7 | 0 | 16.9 |
| | 252-2002 | 1.25 | 0 | 0 |
| | 257-2005 | 7.77 | BLQ < 40.0 | BLQ < 5.00 |
| | 257-2010 | 15 | 0 | 1.53 |
| | 259-2002 | Missing | 0 | 32.2 |
| | N | 30 | 32 | 27 |

-continued

ALO-KNT-302 PK Data

| Week | Subject | Morphine Conc (ng/mL) | Naltrexone Conc (pg/mL) | 6B-Naltrexol Conc (pg/mL) |
|---|---|---|---|---|
|  | Mean | 8.95 | 0.764 | 59 |
|  | SD | 8.35 | 3.31 | 155 |
|  | Min | 0 | 0 | 0 |
|  | Median | 6.11 | 0 | 4.1 |
|  | Max | 30.6 | 17.7 | 763 |
|  | CV % | 93.4 | 433.4 | 262.7 |
| 8 | 201-2005 | 6.74 | 4.83 | 58.8 |
|  | 201-2006 | 5.93 | 0 | 7.12 |
|  | 204-2008 | 9.39 | 0 | 28 |
|  | 205-2002 | 21.6 | 0 | 1.68 |
|  | 205-2007 | 6.93 | 0 | 25.7 |
|  | 209-2013 | 16.4 | 0 | Missing |
|  | 212-2001 | 15.2 | 0 | 14.7 |
|  | 212-2002 | 10.3 | LIS | 49.9 |
|  | 212-2005 | Missing | 12.8 | 330 |
|  | 212-2006 | 3.2 | 0 | Missing |
|  | 213-2002 | 28.8 | 0 | 35.4 |
|  | 213-2003 | 17.6 | 0 | 43.5 |
|  | 213-2004 | 80.5 | 0 | 85 |
|  | 213-2006 | 18.6 | 0 | 9.07 |
|  | 213-2007 | 12.9 | 0 | 6.35 |
|  | 214-2002 | 19 | 0 | 18.5 |
|  | 217-2010 | 6.47 | 0 | 0.866 |
|  | 217-2014 | 24.4 | 0 | 31 |
|  | 222-2002 | 0 | 0 | BLQ < 0.500 |
|  | 228-2011 | 13.9 | 0 | Missing |
|  | 229-2005 | 9.48 | 0 | BLQ < 0.500 |
|  | 229-2008 | 8.3 | 0 | 25.1 |
|  | 229-2009 | 4.76 | 0 | 0.527 |
|  | 235-2001 | 9.35 | 0 | 13.1 |
|  | 241-2004 | 37.9 | 0 | BLQ < 1.25 |
|  | 252-2001 | 66.3 | 0 | 37.3 |
|  | 252-2005 | 5.33 | 0 | 40.6 |
|  | 257-2005 | 6.88 | 0 | 14.6 |
|  | 257-2010 | 7.17 | 0 | 7.81 |
|  | N | 28 | 28 | 23 |
|  | Mean | 16.9 | 0.63 | 38.5 |
|  | SD | 18.1 | 2.55 | 66.9 |
|  | Min | 0 | 0 | 0.527 |
|  | Median | 9.89 | 0 | 25.1 |
|  | Max | 80.5 | 12.8 | 330 |
|  | CV % | 107.1 | 405.6 | 173.9 |
| 12 | 201-2005 | 13.8 | 0 | 20.2 |
|  | 201-2006 | 4.63 | 0 | 10.7 |
|  | 204-2008 | 7.35 | 0 | Missing |
|  | 205-2002 | 26.2 | 0 | Missing |
|  | 209-2013 | 20.7 | 0 | 11.9 |
|  | 212-2002 | 9.21 | 0 | 0.722 |
|  | 212-2005 | Missing | 24.5 | 681 |
|  | 212-2006 | 3.47 | 0 | 2.48 |
|  | 213-2004 | 73.7 | 0 | 30.9 |
|  | 213-2006 | 17.6 | 0 | 17.5 |
|  | 213-2007 | 7.2 | 0 | 46.2 |
|  | 214-2002 | 11 | 0 | 72.5 |
|  | 217-2010 | 4.33 | 0 | 0 |
|  | 217-2014 | 38.4 | 0 | 92.3 |
|  | 222-2002 | 2.9 | 0 | 189 |
|  | 228-2006 | 8.37 | 0 | Missing |
|  | 229-2005 | 2.7 | 0 | 0 |
|  | 229-2006 | 6.56 | 0 | BLQ < 1.00 |
|  | 229-2008 | 6.07 | 0 | 21.3 |
|  | 233-2006 | 23.3 | 0 | Missing |
|  | 235-2001 | 19.4 | 0 | 19.1 |
|  | 241-2004 | 30 | 0 | 28.3 |
|  | 252-2001 | 32.4 | 0 | 62.3 |
|  | 252-2002 | 0 | 0 | Missing |
|  | N | 23 | 24 | 18 |
|  | Mean | 16.1 | 1.02 | 72.6 |
|  | SD | 16.5 | 5 | 159 |
|  | Min | 0 | 0 | 0 |
|  | Median | 9.21 | 0 | 20.8 |
|  | Max | 73.7 | 24.5 | 681 |
|  | CV % | 102.8 | 489.9 | 218.6 |
| 16 | 201-2005 | 1.23 | 0 | 0 |
|  | 201-2006 | 5.11 | 0 | 7.25 |
|  | 204-2008 | 10.7 | 18.3 | 153 |
|  | 205-2002 | 43.5 | 0 | 10.3 |
|  | 209-2013 | 26.5 | Missing | Missing |
|  | 212-2005 | ALQ > 60.0 | Missing | Missing |
|  | 212-2006 | 8.99 | 0 | 10.8 |
|  | 213-2004 | Missing | 0 | 39.9 |
|  | 213-2006 | 22.6 | 0 | 1.71 |
|  | 213-2007 | 27 | 4.15 | 69.6 |
|  | 214-2002 | 27.2 | 0 | 25.8 |
|  | 217-2010 | 2.27 | 0 | Missing |

ALO-KNT-302 PK Data

| Week | Subject | Morphine Conc (ng/mL) | Naltrexone Conc (pg/mL) | 6B-Naltrexol Conc (pg/mL) |
|---|---|---|---|---|
| | 217-2014 | 15.9 | LIS | 35.9 |
| | 222-2002 | 27.7 | 23.5 | 477 |
| | 228-2006 | 9.49 | 0 | 21.2 |
| | 229-2005 | 3.93 | 0 | Missing |
| | 229-2006 | 10.8 | 0 | Missing |
| | 229-2008 | 13.9 | 0 | 86.3 |
| | 232-2001 | 6.23 | LIS | Missing |
| | 235-2001 | 12.3 | 7.89 | 201 |
| | 241-2004 | 28.8 | 0 | 13.4 |
| | 252-2002 | 4.12 | 0 | Missing |
| | 257-2005 | 7.73 | 9.88 | 1.46 |
| | 257-2010 | 9.37 | 0 | BLQ < 10.0 |
| | N | 22 | 20 | 16 |
| | Mean | 14.8 | 3.19 | 72.2 |
| | SD | 11.1 | 6.73 | 122 |
| | Min | 1.23 | 0 | 0 |
| | Median | 10.8 | 0 | 23.5 |
| | Max | 43.5 | 23.5 | 477 |
| | CV % | 75.4 | 211.3 | 169.6 |
| 20 | 201-2005 | 6.22 | 0 | Missing |
| | 201-2006 | 7.51 | 0 | Missing |
| | 204-2008 | 10.7 | 0 | 31.4 |
| | 212-2005 | Missing | 0 | 371 |
| | 213-2004 | 43.9 | 0 | 40 |
| | 213-2006 | 25.2 | 0 | Missing |
| | 213-2007 | 17.9 | 0 | Missing |
| | 214-2002 | 26 | LIS | 149 |
| | 217-2010 | 7.47 | 0 | 12.1 |
| | 217-2014 | 26.7 | PC | 21.6 |
| | 222-2002 | 22.1 | 145 | 1680 |
| | 228-2006 | 15.9 | 0 | 32 |
| | 229-2005 | 10 | 0 | Missing |
| | 229-2006 | 7.55 | 0 | Missing |
| | 229-2008 | 5.09 | 0 | 29.1 |
| | 235-2001 | 19.4 | 9.27 | 163 |
| | 241-2004 | 31.6 | 0 | 18.7 |
| | 252-2001 | 24.8 | 0 | 32.2 |
| | 252-2002 | 0 | 0 | Missing |
| | 257-2005 | 4.5 | 0 | Missing |
| | N | 19 | 18 | 12 |
| | Mean | 16.4 | 8.57 | 215 |
| | SD | 11.4 | 34.1 | 473 |
| | Min | 0 | 0 | 12.1 |
| | Median | 15.9 | 0 | 32.1 |
| | Max | 43.9 | 145 | 1680 |
| | CV % | 69.2 | 398.1 | 220 |
| 24 | 201-2005 | 3.66 | 0 | Missing |
| | 201-2006 | 5.04 | 0 | Missing |
| | 203-2002 | 7.8 | 0 | 11.1 |
| | 204-2008 | 9.95 | Missing | Missing |
| | 205-2002 | Missing | 0 | 26.2 |
| | 213-2004 | 49 | 0 | 112 |
| | 213-2007 | 17.1 | 0 | 17.9 |
| | 214-2001 | 19.8 | Missing | Missing |
| | 214-2002 | 21.9 | LIS | 21.4 |
| | 214-2010 | 10.5 | 0 | 17.7 |
| | 217-2010 | 4.26 | 0 | 22.2 |
| | 222-2002 | 0.684 | 0 | 257 |
| | 229-2005 | 6.95 | 0 | 18.7 |
| | 229-2006 | 4.54 | 0 | Missing |
| | 229-2008 | 13 | 0 | 86.9 |
| | 235-2001 | 38.8 | 12.7 | 95.1 |
| | 240-2005 | 19 | Missing | Missing |
| | 241-2004 | 44.9 | 0 | Missing |
| | 252-2001 | 28.7 | 4.99 | 121 |
| | N | 18 | 15 | 12 |
| | Mean | 17 | 1.18 | 67.3 |
| | SD | 14.7 | 3.44 | 72.8 |
| | Min | 0.684 | 0 | 11.1 |
| | Median | 11.8 | 0 | 24.2 |
| | Max | 49 | 12.7 | 257 |
| | CV % | 86.3 | 291.4 | 108.2 |
| 28 | 201-2005 | 8.63 | 0 | Missing |
| | 201-2006 | 8.22 | 0 | Missing |
| | 203-2002 | 9.94 | Missing | Missing |
| | 203-2003 | 3.05 | Missing | Missing |
| | 204-2008 | 17.5 | Missing | Missing |
| | 213-2004 | 38 | 0 | Missing |
| | 213-2007 | 23.4 | Missing | Missing |
| | 214-2002 | 37 | 0 | 142 |
| | 217-2010 | LIS | Missing | Missing |
| | 222-2002 | 10.1 | 38.6 | 1440 |
| | 226-2002 | 0 | Missing | Missing |
| | 229-2005 | 3.5 | 0 | Missing |
| | 229-2006 | 9.69 | 0 | Missing |

ALO-KNT-302 PK Data

| Week | Subject | Morphine Conc (ng/mL) | Naltrexone Conc (pg/mL) | 6B-Naltrexol Conc (pg/mL) |
|---|---|---|---|---|
| | 229-2008 | 9.11 | 0 | 24.9 |
| | 235-2001 | 30.6 | 10.1 | 132 |
| | 241-2004 | 39.5 | 0 | Missing |
| | 251-2001 | 34.1 | 0 | 13.5 |
| | 251-2002 | 39.1 | Missing | Missing |
| | 252-2001 | 54.3 | Missing | Missing |
| | 252-2002 | 0 | Missing | Missing |
| | N | 19 | 11 | 5 |
| | Mean | 19.8 | 4.43 | 350 |
| | SD | 16.5 | 11.7 | 612 |
| | Min | 0 | 0 | 13.5 |
| | Median | 10.1 | 0 | 132 |
| | Max | 54.3 | 38.6 | 1440 |
| | CV % | 83.6 | 265 | 174.6 |
| 32 | 201-2005 | 8.4 | Missing | Missing |
| | 201-2006 | 2.35 | Missing | Missing |
| | 203-2002 | 9.58 | Missing | Missing |
| | 204-2008 | 19.1 | Missing | Missing |
| | 213-2004 | 29.8 | Missing | Missing |
| | 213-2007 | 21.4 | Missing | Missing |
| | 214-2002 | 23.4 | Missing | Missing |
| | 226-2002 | 1.98 | Missing | Missing |
| | 229-2005 | 5.74 | Missing | Missing |
| | 229-2006 | 8.95 | Missing | Missing |
| | 229-2008 | 15 | Missing | Missing |
| | 235-2001 | 24.7 | 0 | 16 |
| | 241-2004 | 24.5 | Missing | Missing |
| | 251-2001 | 35.5 | Missing | Missing |
| | 251-2002 | 33.5 | Missing | Missing |
| | 252-2001 | 43.8 | Missing | Missing |
| | 252-2002 | 0 | Missing | Missing |
| | N | 17 | 1 | 1 |
| | Mean | 18.1 | 0 | 16 |
| | SD | 13 | Missing | Missing |
| | Min | 0 | 0 | 16 |
| | Median | 19.1 | 0 | 16 |
| | Max | 43.8 | 0 | 16 |
| | CV % | 71.9 | Missing | Missing |
| 36 | 201-2005 | 3.62 | Missing | Missing |
| | 201-2006 | 5.77 | Missing | Missing |
| | 213-2004 | 45.2 | Missing | Missing |
| | 213-2007 | Missing | Missing | Missing |
| | 214-2002 | 27.9 | Missing | Missing |
| | 216-2001 | 7.86 | Missing | Missing |
| | 217-2010 | Missing | Missing | Missing |
| | 226-2002 | Missing | Missing | Missing |
| | 229-2005 | LIS | Missing | Missing |
| | 229-2006 | 11.8 | Missing | Missing |
| | 229-2008 | 7.82 | Missing | Missing |
| | 235-2001 | 30.9 | Missing | Missing |
| | 241-2004 | 43.5 | Missing | Missing |
| | 251-2001 | 35.2 | Missing | Missing |
| | 251-2002 | 37.1 | Missing | Missing |
| | 252-2001 | 14.8 | Missing | Missing |
| | 252-2002 | 0 | Missing | Missing |
| | N | 13 | 0 | 0 |
| | Mean | 20.9 | Missing | Missing |
| | SD | 16.2 | Missing | Missing |
| | Min | 0 | Missing | Missing |
| | Median | 14.8 | Missing | Missing |
| | Max | 45.2 | Missing | Missing |
| | CV % | 77.5 | Missing | Missing |
| 40 | 201-2005 | 4.74 | Missing | Missing |
| | 201-2006 | Missing | Missing | Missing |
| | 209-2013 | Missing | Missing | Missing |
| | 213-2004 | 29 | Missing | Missing |
| | 214-2002 | Missing | Missing | Missing |
| | 226-2002 | Missing | Missing | Missing |
| | 229-2005 | Missing | Missing | Missing |
| | 229-2006 | Missing | Missing | Missing |
| | 229-2008 | Missing | Missing | Missing |
| | 235-2001 | 29 | Missing | Missing |
| | 236-2002 | Missing | Missing | Missing |
| | 241-2004 | ALQ > 60.0 | Missing | Missing |
| | 251-2001 | Missing | Missing | Missing |
| | 251-2002 | Missing | Missing | Missing |
| | 252-2002 | 0 | Missing | Missing |
| | N | 4 | 0 | 0 |
| | Mean | 15.7 | Missing | Missing |
| | SD | 15.5 | Missing | Missing |
| | Min | 0 | Missing | Missing |
| | Median | 16.9 | Missing | Missing |
| | Max | 29 | Missing | Missing |
| | CV % | 98.8 | Missing | Missing |
| 44 | 201-2005 | Missing | Missing | Missing |
| | 201-2006 | Missing | Missing | Missing |
| | 235-2001 | Missing | Missing | Missing |
| | 241-2004 | Missing | Missing | Missing |

-continued

| ALO-KNT-302 PK Data | | | |
|---|---|---|---|
| Week | Subject | Morphine Conc (ng/mL) | Naltrexone Conc (pg/mL) | 6B-Naltrexol Conc (pg/mL) |
| | 252-2001 | 14.2 | Missing | Missing |
| | 252-2002 | 0 | Missing | Missing |
| | N | 2 | 0 | 0 |
| | Mean | 7.1 | Missing | Missing |
| | SD | 10 | Missing | Missing |
| | Min | 0 | Missing | Missing |
| | Median | 7.1 | Missing | Missing |
| | Max | 14.2 | Missing | Missing |
| | CV % | 141.4 | Missing | Missing |
| 100 (ET) | 201-2013 | 0 | 0 | 0 |
| | 202-2004 | 0 | Missing | Missing |
| | 205-2001 | 0 | 0 | BLQ < 2.50 |
| | 205-2003 | 0.778 | 0 | 5.36 |
| | 205-2006 | 0 | 0 | 0 |
| | 208-2001 | 0 | 0 | 0.533 |
| | 211-2010 | 0 | Missing | Missing |
| | 212-2001 | 1.02 | 0 | BLQ < 0.500 |
| | 212-2002 | 1.78 | 0 | 0 |
| | 212-2006 | 8.8 | 0 | 12.6 |
| | 213-2002 | BLQ < 1.00 | 0 | BLQ < 10.0 |
| | 213-2003 | 18.7 | 0 | 1.17 |
| | 213-2005 | 5.27 | 0 | BLQ < 10.0 |
| | 213-2006 | 24.2 | 0 | 35.8 |
| | 214-2003 | 34.4 | 0 | 3.21 |
| | 216-2009 | 33 | Missing | Missing |
| | 217-2014 | 3.81 | LIS | 21.9 |
| | 222-2002 | 40.9 | 118 | 2860 |
| | 222-2011 | 0.214 | 0 | 13.7 |
| | 229-2001 | 0 | 0 | 14.7 |
| | 229-2007 | 0 | 0 | ALQ > 10.0 |
| | 241-2001 | 0 | 0 | 0 |
| | 241-2007 | 8.64 | 0 | BLQ < 0.500 |
| | 241-2019 | 0 | 0 | BLQ < 0.500 |
| | 255-2001 | Missing | 0 | Missing |
| | 255-2003 | 204 | 16.8 | 192 |
| | 257-2001 | 7.75 | 0 | 12 |
| | 257-2010 | 15.6 | 0 | 54 |
| | 259-2002 | 1.88 | 0 | 5.91 |
| | N | 27 | 25 | 18 |
| | Mean | 15.2 | 5.39 | 180 |
| | SD | 39.6 | 23.7 | 670 |
| | Min | 0 | 0 | 0 |
| | Median | 1.78 | 0 | 8.96 |
| | Max | 204 | 118 | 2860 |
| | CV % | 260.3 | 439.5 | 373.3 |

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A method of treating moderate to severe chronic pain in a patient in need thereof comprising orally administering to the patient an intact multi-layer pharmaceutical composition comprising:
   a core;
   an opioid antagonist layer, coating the core;
   a sequestering polymer layer which contains a charge-neutralizing additive and a hydrophobicity-enhancing additive and which coats said opioid antagonist layer;
   an opioid agonist layer coating the sequestering polymer layer, and;
   an osmotic pressure regulating agent located immediately beneath the agonist layer;
   wherein administration of the intact form of the composition to the patient once or twice daily for a time period of at least two weeks results in zero release of the antagonist over the time period as determined by the antagonist concentration in the plasma of the patient.

2. The method of claim 1 wherein administration of the intact form of the composition to the patient for at least a time period selected from the group consisting of four, eight, 12, 16, 20, 24, 28, 32, 36, 40 and 100 weeks.

3. The method of either claim 1 or 2 wherein the antagonist is naltrexone.

4. The method of claim 3 wherein release of naltrexone is determined by measuring plasma levels of B-naltrexol.

5. A method of treating moderate to severe chronic pain in a patients in need thereof comprising orally administering to the patients an intact multi-layer pharmaceutical composition comprising:
   a core;
   an opioid antagonist layer, coating the core;
   a sequestering polymer layer which contains a charge-neutralizing additive and a hydrophobicity-enhancing additive and which coats said opioid antagonist layer;
   an opioid agonist layer coating the sequestering polymer layer, and;
   an osmotic pressure regulating agent located immediately beneath the agonist layer;
   wherein administration of the intact form of the composition to the patients once daily for a time period of at least two weeks results in zero release of the antagonist in about 90% of the patients as determined by measuring antagonist concentration in the plasma of the patients.

6. The method of claim 5 wherein administration of the intact form of the composition to the patient for at least a time period of 28 weeks.

7. The method of either claim 5 or 6 wherein the antagonist is naltrexone.

8. The method of claim 7 wherein release of naltrexone is determined by measuring plasma levels of B-naltrexol.

9. The method of claim 2 or 3 wherein the opioid agonist is morphine.

10. The method of claim 7 or 8 wherein the opioid agonist is morphine.

11. The method of claim 9 or 10 wherein the osmotic pressure regulating agent is hydroxypropyl methylcellulose or chloride ions.

12. The method of claim 1 wherein the opioid agonist is morphine and the opioid antagonist is naltrexone.

13. A method of treating moderate to severe chronic pain in a patients in need thereof comprising orally administering to the patients an intact multi-layer pharmaceutical composition comprising:
   a core;
   an opioid antagonist layer coating the core;
   a sequestering polymer layer which contains a charge-neutralizing additive and a hydrophobicity-enhancing additive and which coats said opioid antagonist layer;
   an opioid agonist layer coating the sequestering polymer layer, and
   an osmotic pressure regulating agent located immediately beneath the agonist layer;
   wherein administration of the intact form of the composition to the patients once daily for a time period of at least two weeks results in zero release of the antagonist in about 80% of the patients as determined by measuring antagonist concentration in the plasma of the patients.

14. The method of claim 13 wherein the osmotic pressure agent is sodium chloride.

\* \* \* \* \*